(12) United States Patent
Nelson et al.

(10) Patent No.: US 9,279,150 B2
(45) Date of Patent: *Mar. 8, 2016

(54) MUTANT ENDONUCLEASE V ENZYMES AND APPLICATIONS THEREOF

(71) Applicant: General Electric Company, Schenectady, NY (US)

(72) Inventors: John Richard Nelson, Clifton Park, NY (US); Robert Scott Duthie, Schenetady, NY (US); Gregory Andrew Grossman, Halfmoon, NY (US); Anuradha Sekher, Belle Mead, NJ (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 119 days.

This patent is subject to a terminal disclaimer.

(21) Appl. No.: 13/840,062

(22) Filed: Mar. 15, 2013

(65) Prior Publication Data

US 2014/0093878 A1 Apr. 3, 2014

Related U.S. Application Data

(63) Continuation-in-part of application No. 13/330,745, filed on Dec. 20, 2011.

(51) Int. Cl.
| | |
|---|---|
| *C07K 1/00* | (2006.01) |
| *C12Q 1/68* | (2006.01) |
| *C12N 9/22* | (2006.01) |
| *C07K 14/00* | (2006.01) |
| *C12N 9/00* | (2006.01) |

(52) U.S. Cl.
CPC ........... *C12Q 1/6858* (2013.01); *C07K 1/00* (2013.01); *C07K 14/00* (2013.01); *C12N 9/22* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 7,198,894 B2 | 4/2007 | Barany et al. | |
| 7,807,431 B2 | 10/2010 | Barany et al. | |
| 7,960,159 B2 | 6/2011 | Barany et al. | |
| 8,202,972 B2 | 6/2012 | Nelson et al. | |
| 2003/0148283 A1* | 8/2003 | Barany et al. | 435/6 |
| 2004/0067559 A1 | 4/2004 | McCarthy et al. | |
| 2009/0047678 A1 | 2/2009 | Kutyavin | |
| 2010/0055742 A1 | 3/2010 | Nakashima et al. | |
| 2010/0323425 A1 | 12/2010 | Barany et al. | |
| 2011/0171649 A1 | 7/2011 | Kutyavin | |
| 2012/0021461 A1 | 1/2012 | Millar et al. | |

OTHER PUBLICATIONS

Gao et al., "Switching base preferences of mismatch cleavage in endonuclease V: an improved method for scanning point mutations", Nucleic Acids Research, vol. 35, No. 1, 2007, 6 Pages.

Huang et al., "Mutational Analysis of Endonuclease V from *Thermotoga maritima*", Biochemistry, vol. 41, No. 26, 2002, pp. 8342-8350.

Min Yao and Yoke W. Kow, "Interaction of Deoxyinosine 3*-Endonuclease from *Escherichia coli* with DNA Containing Deoxyinosine", The Journal of Biological Chemistiy,vol. 270, No. 48, Issue of Dec. 1, 1995, pp. 28609-28616.

Yao et al., "Purification and Characterization of a Novel Deoxyinosine-specific Enzyme, Deoxyinosine 3' Endonuclease, from *Escherichia coli*" The journal of Biological chemistry, vol. 269, No. 23, Issue of Jun. 10, 1994, pp. pp. 16260-16268.

Yao et al., "Further Characterization of *Escherichia coli* Endonuclease V -Mechanism of Recognition for Deoxyinosine, Deoxyuridine, and Base Mismatches in DNA", The Journal of Biological Chemistry, vol. 272, No. 49, Issue of Dec. 5,1997, pp. 30774-30779.

Feng et al., "Active Site Plasticity of Endonuclease V from *Salmonella typhimurium*", Biochemistry, vol. 44, No. 2, 2005, pp. 675-683.

Feng et al., "Defining Amino Acid Residues Involved in DNA-Protein Interactions and Revelation of 3'-Exonuclease Activity in Endonuclease V", Biochemistry, vol. 44, No. 34, 2005, pp. 11486-11495.

Feng et al., "Catalytic Mechanism of Endonuclease V: A Catalytic and Regulatory Two-Metal Model", Biochemistry, vol. 45, No. 34, 2006, pp. 10251-10259.

Mi et al., "Dissecting endonuclease and exonuclease activities in endonuclease V from *Thermotoga maritima*" Nucleic Acids Research, vol. 39, No. 2, 2010, pp. 536-544.

Moe et al., "Incision at hypoxanthine residues in DNA by a mammalian homologue of the *Escherichia coli* antimutator enzyme endonuclease V", Nucleic Acids Research, 2003, vol. 31, No. 14, pp. 3893-3900.

Huang et al., "Multiple Cleavage Activities of Endonuclease V from *Thermotoga maritima*: Recognition and Strand Nicking Mechanism", Biochemistry-American Chemical Society, vol. 40, Issue 30, Jul. 3, 2001;pp. 8738-8748.

Honghai Gao., "Biochemical Study of Endonuclease V and its Application in Mutation Scanning", Doctorate of philosophy, Clemson University, Jun. 2007, 176 Pages.

A. Joneja, X. Huang, "Linear Nicking Endonuclease-Mediated Strand Displacement DNA Amplification", Anal Biochem, vol. 414, Issue 1, Jul. 1, 2011, pp. 58-69.

"Endonuclease V,T.maritima", Thermo Scientific, 2011, 3 Pages.

\* cited by examiner

*Primary Examiner* — Prabha Chunduru
(74) *Attorney, Agent, or Firm* — Fletcher Yoder, P.C.

(57) ABSTRACT

Provided herein are mutant endonuclease V enzymes that are capable of nicking an inosine-containing DNA sequence. Nucleic acid assays and agents that employ such mutant endonuclease V enzymes to introduce a nick into a target DNA including one or more inosine, and uses a DNA polymerase to generate amplicons of a target DNA are also described.

8 Claims, 21 Drawing Sheets

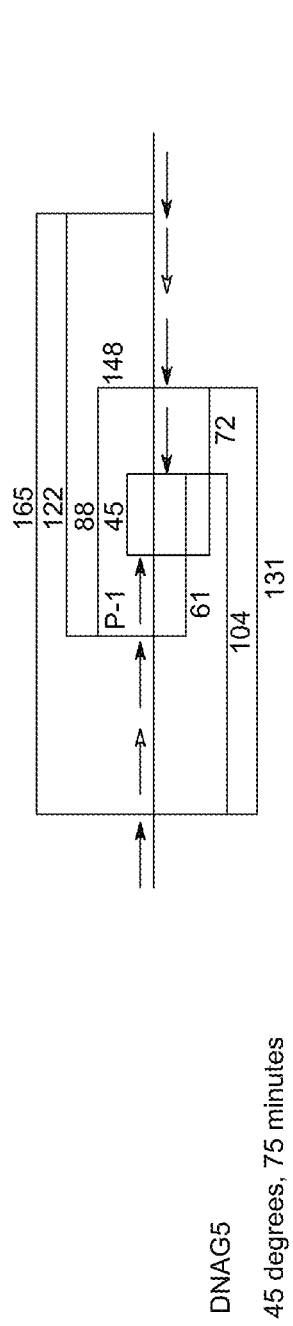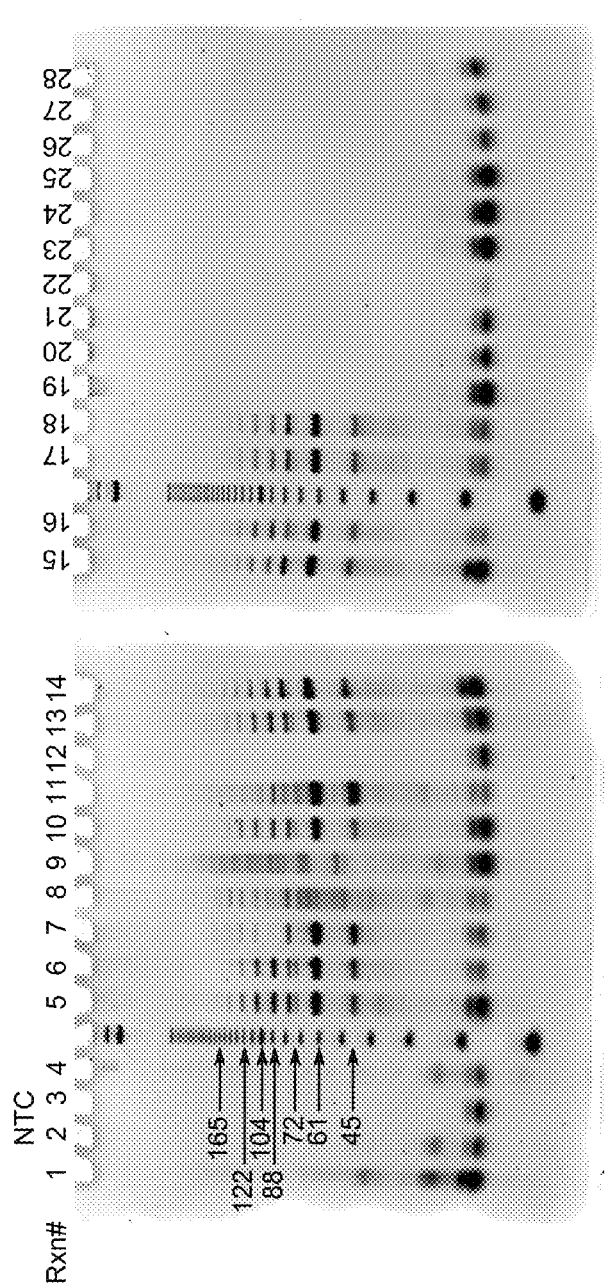
FIG. 5

SEQUENCE LISTING

```
<160> NUMBER OF SEQ ID NOS: 60

<210> SEQ ID NO 1
<211> LENGTH: 225
<212> TYPE: PRT
<213> ORGANISM: Escherichia coli

<400> SEQUENCE: 1

Met Ile Met Asp Leu Ala Ser Leu Arg Ala Gln Gln Ile Glu Leu Ala
1               5                   10                  15

Ser Ser Val Ile Arg Glu Asp Arg Leu Asp Lys Asp Pro Pro Asp Leu
                20                  25                  30

Ile Ala Gly Ala Asp Val Gly Phe Glu Gln Gly Gly Glu Val Thr Arg
            35                  40                  45

Ala Ala Met Val Leu Leu Lys Tyr Pro Ser Leu Glu Leu Val Glu Tyr
        50                  55                  60

Lys Val Ala Arg Ile Ala Thr Thr Met Pro Tyr Ile Pro Gly Phe Leu
65                  70                  75                  80

Ser Phe Arg Glu Tyr Pro Ala Leu Leu Ala Ala Trp Glu Met Leu Ser
                85                  90                  95
```

```
Gln Lys Pro Asp Leu Val Phe Val Asp Gly His Gly Ile Ser His Pro
            100                 105                 110
Arg Arg Leu Gly Val Ala Ser His Phe Gly Leu Leu Val Asp Val Pro
            115                 120                 125
Thr Ile Gly Val Ala Lys Lys Arg Leu Cys Gly Lys Phe Glu Pro Leu
            130                 135                 140
Ser Ser Glu Pro Gly Ala Leu Ala Pro Leu Met Asp Lys Gly Glu Gln
145                 150                 155                 160
Leu Ala Trp Val Trp Arg Ser Lys Ala Arg Cys Asn Pro Leu Phe Ile
                165                 170                 175
Ala Thr Gly His Arg Val Ser Val Asp Ser Ala Leu Ala Trp Val Gln
            180                 185                 190
Arg Cys Met Lys Gly Tyr Arg Leu Pro Glu Pro Thr Arg Trp Ala Asp
            195                 200                 205
Ala Val Ala Ser Glu Arg Pro Ala Phe Val Arg Tyr Thr Ala Asn Gln
            210                 215                 220
Pro
225

<210> SEQ ID NO 2
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide: GE E.Coli Endonuclease V Y73A

<400> SEQUENCE: 2

Met Ile Met Asp Leu Ala Ser Leu Arg Ala Gln Gln Ile Glu Leu Ala
1               5                   10                  15
Ser Ser Val Ile Arg Glu Asp Arg Leu Asp Lys Asp Pro Pro Asp Leu
            20                  25                  30
Ile Ala Gly Ala Asp Val Gly Phe Glu Gln Gly Gly Glu Val Thr Arg
            35                  40                  45
Ala Ala Met Val Leu Leu Lys Tyr Pro Ser Leu Glu Leu Val Glu Tyr
50                  55                  60
Lys Val Ala Arg Ile Ala Thr Thr Met Pro Ala Ile Pro Gly Phe Leu
65                  70                  75                  80
Ser Phe Arg Glu Tyr Pro Ala Leu Leu Ala Ala Trp Glu Met Leu Ser
            85                  90                  95
Gln Lys Pro Asp Leu Val Phe Val Asp Gly His Gly Ile Ser His Pro
            100                 105                 110
Arg Arg Leu Gly Val Ala Ser His Phe Gly Leu Leu Val Asp Val Pro
            115                 120                 125
Thr Ile Gly Val Ala Lys Lys Arg Leu Cys Gly Lys Phe Glu Pro Leu
            130                 135                 140
Ser Ser Glu Pro Gly Ala Leu Ala Pro Leu Met Asp Lys Gly Glu Gln
145                 150                 155                 160
Leu Ala Trp Val Trp Arg Ser Lys Ala Arg Cys Asn Pro Leu Phe Ile
                165                 170                 175
Ala Thr Gly His Arg Val Ser Val Asp Ser Ala Leu Ala Trp Val Gln
            180                 185                 190
Arg Cys Met Lys Gly Tyr Arg Leu Pro Glu Pro Thr Arg Trp Ala Asp
            195                 200                 205
```

Ala Val Ala Ser Glu Arg Pro Ala Phe Val Arg Tyr Thr Ala Asn Gln
    210                 215                 220

Pro Leu Glu
225

<210> SEQ ID NO 3
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide: GE Afu Endonuclease V

<400> SEQUENCE: 3

Met Leu Gln Met Asn Leu Glu Glu Leu Arg Arg Ile Gln Glu Glu Met
1               5                   10                  15

Ser Arg Ser Val Val Leu Glu Asp Leu Ile Pro Leu Glu Glu Leu Glu
            20                  25                  30

Tyr Val Val Gly Val Asp Gln Ala Phe Ile Ser Asp Glu Val Val Ser
        35                  40                  45

Cys Ala Val Lys Leu Thr Phe Pro Glu Leu Glu Val Val Asp Lys Ala
    50                  55                  60

Val Arg Val Glu Lys Val Thr Phe Pro Ala Ile Pro Thr Phe Leu Met
65                  70                  75                  80

Phe Arg Glu Gly Glu Pro Ala Val Asn Ala Val Lys Gly Leu Val Asp
                85                  90                  95

Asp Arg Ala Ala Ile Met Val Asp Gly Ser Gly Ile Ala His Pro Arg
            100                 105                 110

Arg Cys Gly Leu Ala Thr Tyr Ile Ala Leu Lys Leu Arg Lys Pro Thr
        115                 120                 125

Val Gly Ile Thr Lys Lys Arg Leu Phe Gly Glu Met Val Glu Val Glu
    130                 135                 140

Asp Gly Leu Trp Arg Leu Leu Asp Gly Ser Glu Thr Ile Gly Tyr Ala
145                 150                 155                 160

Leu Lys Ser Cys Arg Arg Cys Lys Pro Ile Phe Ile Ser Pro Gly Ser
                165                 170                 175

Tyr Ile Ser Pro Asp Ser Ala Leu Glu Leu Thr Arg Lys Cys Leu Lys
            180                 185                 190

Gly Tyr Lys Leu Pro Glu Pro Ile Arg Ile Ala Asp Lys Leu Thr Lys
        195                 200                 205

Glu Val Lys Arg Glu Leu Thr Pro Thr Ser Lys Leu Lys
    210                 215                 220

<210> SEQ ID NO 4
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide: Ban 1 Template

<400> SEQUENCE: 4
caattgtaat ttctgtacgt ctcttatcat tgaagcgctc ttttacttct gttaattctt    60
cacgaataat ctcaaga                                                    77

<210> SEQ ID NO 5
<211> LENGTH: 16
<212> TYPE: DNA
<213> ORGANISM: Artificial Sequence

```
<220> FEATURE:
<223> OTHER INFORMATION: Description of Artificial Sequence: Synthetic
      primer: P-1
<220> FEATURE:
<221> NAME/KEY: misc_feature
<222> LOCATION: (15)..(15)
<223> OTHER INFORMATION: n is an Inosine

<400> SEQUENCE: 5
tcttgagatt attcnt                                                          16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: P2-1
<220> FEATURE:
<221> NAME/KEY: misc_feature
<222> LOCATION: (15)..(15)
<223> OTHER INFORMATION: n is an Inosine

<400> SEQUENCE: 6
caattgtaat ttctnt                                                          16

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      primer: P3
<220> FEATURE:
<221> NAME/KEY: modified_base
<222> LOCATION: (51)..(51)
<223> OTHER INFORMATION: Dideoxycytosine

<400> SEQUENCE: 7
aaattaatac gactcactat agggtgaaga attaacagaa gtaaaagagc c                   51

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      primer: P-3 Mismatched

<400> SEQUENCE: 8
aaattaatac gactcactat agggttgaag aattaacaga agtaaaagag a                   51

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      primer: P-3 No ddc

<400> SEQUENCE: 9
aaattaatac gactcactat agggtgaaga attaacagaa g                              41

<210> SEQ ID NO 10
<211> LENGTH: 51
<212> TYPE: DNA
<213> ORGANISM: Artificial Sequence
```

```
-continued

<220> FEATURE:
<223> OTHER INFORMATION: Description of Artificial Sequence: Synthetic
      primer: P-3 SD Mod
<220> FEATURE:
<221> NAME/KEY: modified_base
<222> LOCATION: (51)..(51)
<223> OTHER INFORMATION: Dideoxycytosine

<400> SEQUENCE: 10
aaattaatac gactcactat agggttgaag aattaacaga agtaaaagag c              51

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: Primer 1354
<220> FEATURE:
<221> NAME/KEY: misc_feature
<222> LOCATION: (15)..(15)
<223> OTHER INFORMATION: n is an Inosine

<400> SEQUENCE: 11
tcgctgaatt aaaanc                                                      16

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer: Primer 1333
<220> FEATURE:
<221> NAME/KEY: misc_feature
<222> LOCATION: (17)..(17)
<223> OTHER INFORMATION: n is an Inosine

<400> SEQUENCE: 12
atcaagattt aatgaant                                                    18

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: Primer 1498
<220> FEATURE:
<221> NAME/KEY: misc_feature
<222> LOCATION: (15)..(15)
<223> OTHER INFORMATION: n is an Inosine

<400> SEQUENCE: 13
tgttctggaa tcaant                                                      16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: Primer 1517
<220> FEATURE:
<221> NAME/KEY: misc_feature
<222> LOCATION: (15)..(15)
<223> OTHER INFORMATION: n is an Inosine

<400> SEQUENCE: 14
aacgtaatgg cgatnt                                                      16
```

```
<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: Primer 1275
<220> FEATURE:
<221> NAME/KEY: misc_feature
<222> LOCATION: (15)..(15)
<223> OTHER INFORMATION: n is an Inosine

<400> SEQUENCE: 15
ttagatatgc gtctnc                                                     16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: Primer 1294
<220> FEATURE:
<221> NAME/KEY: misc_feature
<222> LOCATION: (15)..(15)
<223> OTHER INFORMATION: n is an Inosine

<400> SEQUENCE: 16
gcttaacagg attana                                                     16

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer: Primer 1313
<220> FEATURE:
<221> NAME/KEY: misc_feature
<222> LOCATION: (17)..(17)
<223> OTHER INFORMATION: n is an Inosine

<400> SEQUENCE: 17
cgaaaaaatt gaacaana                                                   18

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: Primer 1378
<220> FEATURE:
<221> NAME/KEY: misc_feature
<222> LOCATION: (15)..(15)
<223> OTHER INFORMATION: n is an Inosine

<400> SEQUENCE: 18
cagatgaaga aaagnt                                                     16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: Primer 1482
<220> FEATURE:
<221> NAME/KEY: misc_feature
<222> LOCATION: (15)..(15)
<223> OTHER INFORMATION: n is an Inosine
```

```
<400> SEQUENCE: 19
cttcatcttc aatana                                                    16

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer: Primer 1534
<220> FEATURE:
<221> NAME/KEY: misc_feature
<222> LOCATION: (17)..(17)
<223> OTHER INFORMATION: n is an Inosine

<400> SEQUENCE: 20
aatataacca ttatgant                                                  18

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      primer: Primer 1560
<220> FEATURE:
<221> NAME/KEY: misc_feature
<222> LOCATION: (14)..(14)
<223> OTHER INFORMATION: n is an Inosine

<400> SEQUENCE: 21
tacgtagaag ctgnc                                                     15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      primer: Primer 1579
<220> FEATURE:
<221> NAME/KEY: misc_feature
<222> LOCATION: (14)..(14)
<223> OTHER INFORMATION: n is an Inosine

<400> SEQUENCE: 22
accacggttc tgtnt                                                     15

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer: cP-3 3' Quencher
<220> FEATURE:
<221> NAME/KEY: modified_base
<222> LOCATION: (24)..(24)
<223> OTHER INFORMATION: Cojugated to Iowa Black

<400> SEQUENCE: 23
ccctatagtg agtcgtatta attt                                           24

<210> SEQ ID NO 24
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer: Fluorescent Primer 1
<220> FEATURE:
<221> NAME/KEY: modified_base
<222> LOCATION: (1)..(1)
<223> OTHER INFORMATION: Conjugated to FAM
<220> FEATURE:
<221> NAME/KEY: misc_feature
<222> LOCATION: (9)..(9)
<223> OTHER INFORMATION: n is an Inosine

<400> SEQUENCE: 24
ggtcgactna ggaggatccc cgggtac                                              27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer: Fluorescent Primer 2
<220> FEATURE:
<221> NAME/KEY: modified_base
<222> LOCATION: (1)..(1)
<223> OTHER INFORMATION: Cojugated to HEX

<400> SEQUENCE: 25
ccggggatcc tcctcagtcg acctgca                                              27

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer: endo V us

<400> SEQUENCE: 26
gagatataca tatggatctc gcg                                                  23

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer: endoV int ds

<400> SEQUENCE: 27
gaatcgccgg catggtggtg gcgatgcg                                             28

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      primer: endoV int us

<400> SEQUENCE: 28
accatgccgg cgattccagg ttttctttcc ttc                                       33

<210> SEQ ID NO 29
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer: endo V ds

<400> SEQUENCE: 29
tggtgctcga ggggctgatt tgatg                                          25

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer: DNA-G-Long-3'

<400> SEQUENCE: 30
gatattcatc aatcggagta cgttttc                                        27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer: DNA-G-5'

<400> SEQUENCE: 31
acaatcaaca acaagcacga attcgag                                        27

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer: 7290R
<220> FEATURE:
<221> NAME/KEY: misc_feature
<222> LOCATION: (19)..(19)
<223> OTHER INFORMATION: n is an Inosine

<400> SEQUENCE: 32
agttcttctt tcgtccccnt                                                20

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      primer: 7270R
<220> FEATURE:
<221> NAME/KEY: misc_feature
<222> LOCATION: (15)..(16)
<223> OTHER INFORMATION: n is an Inosine

<400> SEQUENCE: 33
caggctgaca tcacnnt                                                   17

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer: 7253R
```

<220> FEATURE:
<221> NAME/KEY: misc_feature
<222> LOCATION: (18)..(18)
<223> OTHER INFORMATION: n is an Inosine

<400> SEQUENCE: 34
tcagttgttc acccagcna                                                    19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer: 7234R
<220> FEATURE:
<221> NAME/KEY: misc_feature
<222> LOCATION: (18)..(18)
<223> OTHER INFORMATION: n is an Inosine

<400> SEQUENCE: 35
gcggagacgg gcaatcant                                                    19

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      primer: 7215R
<220> FEATURE:
<221> NAME/KEY: misc_feature
<222> LOCATION: (15)..(16)
<223> OTHER INFORMATION: n is an Inosine

<400> SEQUENCE: 36
tcatctttcg tcatnna                                                      17

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer: 7194R
<220> FEATURE:
<221> NAME/KEY: misc_feature
<222> LOCATION: (17)..(18)
<223> OTHER INFORMATION: n is an Inosine

<400> SEQUENCE: 37
tccacagaga aacaatnnc                                                    19

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      primer: 7062F
<220> FEATURE:
<221> NAME/KEY: misc_feature
<222> LOCATION: (15)..(16)
<223> OTHER INFORMATION: n is an Inosine

<400> SEQUENCE: 38
accaccggcg atccnnc                                                      17

```
<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer: 7079F
<220> FEATURE:
<221> NAME/KEY: misc_feature
<222> LOCATION: (16)..(16)
<223> OTHER INFORMATION: n is an Inosine

<400> SEQUENCE: 39
gcgtgagttc accatna                                                    17

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer: 7096F
<220> FEATURE:
<221> NAME/KEY: misc_feature
<222> LOCATION: (17)..(17)
<223> OTHER INFORMATION: n is an Inosine

<400> SEQUENCE: 40
ttcagtcagc accgctna                                                   18

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      primer: 7111F
<220> FEATURE:
<221> NAME/KEY: misc_feature
<222> LOCATION: (15)..(15)
<223> OTHER INFORMATION: n is an Inosine

<400> SEQUENCE: 41
tgatgctgct ggctna                                                     16

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      primer: 7127F
<220> FEATURE:
<221> NAME/KEY: misc_feature
<222> LOCATION: (16)..(16)
<223> OTHER INFORMATION: n is an Inosine

<400> SEQUENCE: 42
ccctgatgag ttcgtnt                                                    17

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      primer: 7144F
<220> FEATURE:
<221> NAME/KEY: misc_feature
<222> LOCATION: (14)..(14)
<223> OTHER INFORMATION: n is an Inosine
```

```
<400> SEQUENCE: 43
ccgtacaact ggcnt                                                        15

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer: T7-7158F-misA

<400> SEQUENCE: 44
atgactggtg gacagcaaat gggtaaatta atacgactca ctatagggtt                  50

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide: Quencher Oligo
<220> FEATURE:
<221> NAME/KEY: modified_base
<222> LOCATION: (24)..(24)
<223> OTHER INFORMATION: Conjugated to Iowa Black

<400> SEQUENCE: 45
ccctatagtg agtcgtatta attt                                              24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide: Dye Oligo
<220> FEATURE:
<221> NAME/KEY: modified_base
<222> LOCATION: (6)..(6)
<223> OTHER INFORMATION: Internal TAMRA NHS ester

<400> SEQUENCE: 46
acccatttgc tgtccaccag ttac                                              24

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic
      primer: F. Primer 40FGI
<220> FEATURE:
<221> NAME/KEY: misc_feature
<222> LOCATION: (32)..(32)
<223> OTHER INFORMATION: n is an Inosine

<400> SEQUENCE: 47
gttttcccag tcacgacgtt gtaaaacgac gncc                                   34

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer: R.Primer 40RGI
```

<400> SEQUENCE: 48
tcaaagaagt attgctacaa cgg　　　　　　　　　　　　　　　　　　　　　　　23

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic
      primer: F.Primer 40FGG

<400> SEQUENCE: 49
gttttcccag tcacgacgtt gtaaaacgac ggcc　　　　　　　　　　　　　　　　34

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer: R.Primer 40RGG

<400> SEQUENCE: 50
tcaaagaagt attgctacaa cgg　　　　　　　　　　　　　　　　　　　　　　　23

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      primer: Tban-1 forward primer
<220> FEATURE:
<221> NAME/KEY: misc_feature
<222> LOCATION: (32)..(32)
<223> OTHER INFORMATION: n is an Inosine

<400> SEQUENCE: 51
gcagatgaag aaaaggttct tgagattatt cnt　　　　　　　　　　　　　　　　　33

<210> SEQ ID NO 52
<211> LENGTH: 51
<212> TYPE: DNA
<213> ORGANISM: Artificial Sequence
<220> FEATURE:
<223> OTHER INFORMATION: Description of Artificial Sequence: Synthetic
      primer: Dye-P-3
<220> FEATURE:
<221> NAME/KEY: modified_base
<222> LOCATION: (1)..(1)
<223> OTHER INFORMATION: Conjugated to TAMRA dye
<220> FEATURE:
<221> NAME/KEY: modified_base
<222> LOCATION: (51)..(51)
<223> OTHER INFORMATION: Dideoxycytosine

<400> SEQUENCE: 52
aaattaatac gactcactat agggttgaag aattaacaga agtaaaagag c　　　　　　51

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer: 7114F -continued

```
<220> FEATURE:
<221> NAME/KEY: misc_feature
<222> LOCATION: (18)..(18)
<223> OTHER INFORMATION: n is an Inosine

<400> SEQUENCE: 53
tgctgctggc tgaccctna                                               19

<210> SEQ ID NO 54
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide: Tban-1 DNA template

<400> SEQUENCE: 54
caatagactc cataccacca attgtaattt ctgtacgtct cttatcattg aagcgctctt    60
ttacttctgt taattcttca cgaataatct caagaacctt ttcttcatct gc          112

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      Polynucleotide: Tban-1 reverse template
<220> FEATURE:
<221> NAME/KEY: misc_feature
<222> LOCATION: (33)..(33)
<223> OTHER INFORMATION: n is an Inosine

<400> SEQUENCE: 55
caatagactc cataccacca attgtaattt ctnt                               34

<210> SEQ ID NO 56
<211> LENGTH: 221
<212> TYPE: PRT
<213> ORGANISM: Archaeoglobus fulgidus

<400> SEQUENCE: 56

Met Leu Gln Met Asn Leu Glu Glu Leu Arg Arg Ile Gln Glu Glu Met
1               5                   10                  15

Ser Arg Ser Val Val Leu Glu Asp Leu Ile Pro Leu Glu Glu Leu Glu
            20                  25                  30

Tyr Val Val Gly Val Asp Gln Ala Phe Ile Ser Asp Glu Val Val Ser
        35                  40                  45

Cys Ala Val Lys Leu Thr Phe Pro Glu Leu Glu Val Val Asp Lys Ala
    50                  55                  60

Val Arg Val Glu Lys Val Thr Phe Pro Tyr Ile Pro Thr Phe Leu Met
65                  70                  75                  80

Phe Arg Glu Gly Glu Pro Ala Val Asn Ala Val Lys Gly Leu Val Asp
                85                  90                  95

Asp Arg Ala Ala Ile Met Val Asp Gly Ser Gly Ile Ala His Pro Arg
            100                 105                 110

Arg Cys Gly Leu Ala Thr Tyr Ile Ala Leu Lys Leu Arg Lys Pro Thr
        115                 120                 125

Val Gly Ile Thr Lys Lys Arg Leu Phe Gly Glu Met Val Glu Val Glu
    130                 135                 140

Asp Gly Leu Trp Arg Leu Leu Asp Gly Ser Glu Thr Ile Gly Tyr Ala
145                 150                 155                 160
```

```
Leu Lys Ser Cys Arg Arg Cys Lys Pro Ile Phe Ile Ser Pro Gly Ser
                165                 170                 175

Tyr Ile Ser Pro Asp Ser Ala Leu Glu Leu Thr Arg Lys Cys Leu Lys
            180                 185                 190

Gly Tyr Lys Leu Pro Glu Pro Ile Arg Ile Ala Asp Lys Leu Thr Lys
        195                 200                 205

Glu Val Lys Arg Glu Leu Thr Pro Thr Ser Lys Leu Lys
210                 215                 220
```

<210> SEQ ID NO 57
<211> LENGTH: 225
<212> TYPE: PRT
<213> ORGANISM: Termotoga maritima

<400> SEQUENCE: 57

```
Met Asp Tyr Arg Gln Leu His Arg Trp Asp Leu Pro Pro Glu Glu Ala
1               5                   10                  15

Ile Lys Val Gln Asn Glu Leu Arg Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Leu Glu Tyr Pro Ser Phe
50                  55                  60

Lys Ile Leu Glu Val Val Ser Glu Arg Gly Glu Ile Thr Phe Pro Tyr
65                  70                  75                  80

Ile Pro Gly Leu Leu Ala Phe Arg Glu Gly Pro Leu Phe Leu Lys Ala
            85                  90                  95

Trp Glu Lys Leu Arg Thr Lys Pro Asp Val Val Phe Asp Gly Gln
            100                 105                 110

Gly Leu Ala His Pro Arg Lys Leu Gly Ile Ala Ser His Met Gly Leu
            115                 120                 125

Phe Ile Glu Ile Pro Thr Ile Gly Val Ala Lys Ser Arg Leu Tyr Gly
130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
        195                 200                 205

Pro Thr Arg Leu Ala His Ile Tyr Thr Gln Arg Leu Lys Lys Gly Leu
210                 215                 220

Phe
225
```

<210> SEQ ID NO 58
<211> LENGTH: 225
<212> TYPE: PRT
<213> ORGANISM: Artificial Sequence
<220> FEATURE:
<223> OTHER INFORMATION: Y80A mutant of Tma Endonuclease V

<400> SEQUENCE: 58

```
Met Asp Tyr Arg Gln Leu His Arg Trp Asp Leu Pro Pro Glu Glu Ala
1               5                   10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
    50                  55                  60

Lys Ile Leu Glu Val Val Ser Glu Arg Gly Glu Ile Thr Phe Pro Ala
65                  70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Asp Val Val Phe Asp Gly Gln
            100                 105                 110

Gly Leu Ala His Pro Arg Lys Leu Gly Ile Ala Ser His Met Gly Leu
        115                 120                 125

Phe Ile Glu Ile Pro Thr Ile Gly Val Ala Lys Ser Arg Leu Tyr Gly
    130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
        195                 200                 205

Pro Thr Arg Leu Ala His Ile Tyr Thr Gln Arg Leu Lys Lys Gly Leu
    210                 215                 220

Phe
225
```

<210> SEQ ID NO 59
<211> LENGTH: 678
<212> TYPE: DNA
<213> ORGANISM: Escherichia coli
<220> FEATURE:
<221> NAME/KEY: misc_feature
<222> LOCATION: (283)..(285)
<223> OTHER INFORMATION: n is a, c, g, or t

<400> SEQUENCE: 59

```
gtgattatgg atctcgcgtc attacgcgct caacaaatcg aactggcttc ttctgtgatc    60
cgcgaggatc gactcgataa agatccaccg gatctgatcg ccggagccga tgtcgggttt   120
gagcagggcg gagaagtgac gcgagcggcg atggtgctgc tgaaatatcc ctcgcttgag   180
ctggtcgagt ataaagttgc cgcatcgcc accaccatgc cttacattcc aggttttctt   240
tccttccgcg aatatcctgc gctgctggca gcgtgggaga tgnnntcgca aaagccggat   300
ttagtgtttg tcgatggtca tgggatctcg catcctcgcc gtcttggcgt cgccagccat   360
tttggcttat tggtggatgt gccgaccatt ggcgtggcga aaaacggct ctgcggtaaa   420
tcgaaccgc tctccagcga accgggcgcg ctggccccac tgatggataa aggcgagcag   480
ctggcctggg tctggcgcag caaagcgcgc tgtaacccgt tgtttatcgc taccggccat   540
cgggtcagcg tggacagcgc gctggcgtgg gtacaacgct gcatgaaagg ctatcgtctg   600
```

```
ccggagccaa cgcgctgggc ggacgcggtg gcctcggaac gtccggcgtt cgtgcgctat    660
acagcaaatc agccctaa                                                  678

<210> SEQ ID NO 60
<211> LENGTH: 666
<212> TYPE: DNA
<213> ORGANISM: Archaeoglobus fulgidus
<220> FEATURE:
<221> NAME/KEY: misc_feature
<222> LOCATION: (220)..(222)
<223> OTHER INFORMATION: n is a, c, g, or t

<400> SEQUENCE: 60
gtgcttcaaa tgaatctcga agagctgagg aggatacagg aggagatgtc cagaagtgtg     60
gttctcgaag acttaatccc tcttgaagag cttgagtacg ttgtgggtgt tgatcaggcc    120
tttatcagcg atgaggttgt ctcatgtgcg gtcaagctga cctttccgga actggaggtt    180
gttgataaag ctgtgagggt tgagaaggtc actttccccn nnatcccccac ctttctcatg    240 ttcagggagg gagagcctgc agttaatgcg gtcaaagggc ttgtggatga cagagcggca    300
atcatggttg atgggagcgg aattgcccat ccgagaaggt gcgggcttgc aacatacatc    360
gccctaaagc tgagaaagcc gactgtgggg ataacaaaga aaaggctttt tggtgagatg    420
gtagaggtgg aagatgggct ttggaggctt ttagatggaa gtgaaaccat aggctacgcc    480
cttaaaagct gcaggaggtg caaaccaatc ttcatctcac cggggagtta catatctcct    540
gactcagcct tggagctgac gagaaagtgc cttaaaggct acaagcttcc tgagccgata    600
agaatcgccg acaaacttac caaggaggtt aagagggagt tgactccaac ctcaaagctt    660
aaataa                                                               666
```

MUTANT ENDONUCLEASE V ENZYMES AND APPLICATIONS THEREOF

CROSS REFERENCE TO RELATED APPLICATIONS

This application is a continuation-in-part of U.S. patent application Ser. No. 13/330,745, filed on Dec. 20, 2011, which is a divisional of U.S. patent application Ser. No. 11/621,703, filed on Jan. 10, 2007, U.S. Pat. No. 8,202,972 B2, both entitled ISOTHERMAL DNA AMPLIFICATION.

FIELD OF INVENTION

The present invention generally relates to endonuclease V mutant enzymes that are capable of introducing a nick in a DNA sequence comprising an inosine residue that is base-paired with a cytosine residue and their use in nucleic acid assays that include nicking of DNA sequences containing inosine nucleotides. It further relates to improved DNA amplification methods wherein a nick is introduced in a double stranded, target DNA by an endonuclease V mutant followed by amplification of the target DNA. Kits comprising such engineered endonuclease V are also disclosed.

BACKGROUND

DNA amplification is a process of copying a single or double-stranded target DNA to generate multiple copies of the target DNA. Since DNA strands are antiparallel and complementary, each strand may serve as a template (template strand) for the production of an opposite strand (complementary strand) by a DNA polymerase. The template strand is preserved as a whole or as a truncated portion and the complementary strand is assembled from nucleoside triphosphates. A variety of techniques are currently available for efficient amplification of nucleic acids such as polymerase chain reaction (PCR), ligase chain reaction (LCR), self-sustained sequence replication (3SR), nucleic acid sequence based amplification (NASBA), strand displacement amplification (SDA), multiple displacement amplification (MDA), or rolling circle amplification (RCA). Many of these techniques generate a large number of amplified products in a short span of time. For example, in a polymerase chain reaction (PCR), a target DNA, a pair of primers and a DNA polymerase are combined and subjected to repeated temperature changes that permit melting, annealing, and elongation steps to result in an exponential amplification of the starting target DNA. However, in PCR, the melting or denaturation step typically occurs at a high temperature limiting the choice of polymerases to thermophilic polymerases.

DNA amplification often suffers from high background signals, which are generated by non-specific amplification reactions yielding undesired/false amplification products. For example, non-specific amplification may result from various primer gymnastics such as nucleic acid template-independent primer-primer interactions. Primers may form primer-dimer structures by intra- or inter-strand primer annealing (intra molecular or inter molecular hybridizations), and may get amplified, and may sometimes predominate, inhibit, or mask the amplification of a target DNA sequence. Such non-specific, background amplification reactions become even more problematic where the target nucleic acid to be amplified is available only in limited quantities (e.g., whole-genome amplification from a single DNA molecule). Efficient DNA amplification techniques are needed, if they are to be used for critical applications such as diagnostic applications, wherein a false-positive amplification may likely result in a wrong diagnosis.

Endonuclease V (also referred as endo V or deoxyinosine 3" endonuclease) is a DNA repair enzyme that recognizes DNA containing deoxyinosine (a deamination product of deoxyadenosine, also referred as inosine) residues. Endonuclease V primarily cleaves the second or third phosphodiester bond 3' to an inosine residue in the same strand leaving a nick with a 3'-hydroxyl and a 5'-phosphate. Endonuclease V was first described in *Escherichia coli* (*E. coli*). Apart from inosine residues, *E. coli* endonuclease V also recognizes, to a lesser degree, otherwise modified bases such as abasic sites (AP sites) or urea, base mismatches, insertion/deletion mismatches, hairpin or unpaired loops, flaps and pseudo-Y structures. One or more embodiments of the present invention are directed towards engineered endonuclease V enzymes (mutant endonuclease V) and their use in nucleic acid assays such as strand displacement DNA amplification reactions, wherein the selective nicking capability of mutant endonuclease V is employed to develop an improved method of DNA amplification.

BRIEF DESCRIPTION

One or more embodiments of the present invention are directed to methods, agents, and kits for producing amplification products (i.e., amplicons) from a target DNA using an endonuclease V and an inosine-containing primer. In some embodiments, the methods comprise the steps of (a) providing a target DNA; (b) annealing at least one inosine-containing primer to the target DNA to create a target DNA:primer hybrid; (c) nicking the inosine-containing primer in the target DNA:primer hybrid with an endonuclease at a residue 3' to the inosine residue; and (d) extending the nicked inosine-containing primer via a nucleic acid amplification to produce at least one amplicon complementary to at least one portion of the target DNA.

In some embodiments, a method of producing at least one amplicon based on a target DNA is provided, wherein the method includes (a) providing a target DNA; (b) annealing at least one inosine-containing primer to the target DNA to produce a target DNA:primer hybrid; (c) extending the primer strand via a nucleic acid amplification reaction to produce a complementary strand to at least one portion of the target DNA and to generate a nicking site in the extended primer strand at a residue 3' to the inosine residue; (d) nicking the extended primer strand at the nicking site to generate an initiation site in the primer strand for a subsequent nucleic acid amplification reaction; and (e) repeating steps (c) and (d) employing a strand displacement nucleic acid polymerase for the nucleic acid amplification reaction to produce the at least one amplicon based on the target DNA.

In some embodiments, a method of producing at least one amplicon based on a target DNA is provided, wherein the method comprises: (a) providing the target DNA; (b) providing a DNA amplification reaction mixture comprising at least one inosine-containing primer, at least one 5'→3' exonuclease-deficient DNA polymerase having strand displacement activity, at least one nuclease that is capable of nicking a DNA at a residue 3' to an inosine residue, and dNTP mixture; and (c) amplifying at least one portion of the target DNA using the DNA amplification reaction mixture of step (b) to produce the at least one amplicon.

In some embodiments, amplicon production kits are provided that comprises at least one inosine-containing primer, at least one exonuclease-deficient DNA polymerase with strand displacement activity and at least one nuclease that is capable of nicking DNA at a residue 3' to an inosine residue.

In some embodiments, mutant endonuclease V enzymes are provided. In some embodiments, the amino acid sequence of the mutant endonuclease V comprises a modified sequence of SEQ ID NO: 1, wherein the modification is a replacement of a Tyrosine residue at the $75^{th}$ position of the SEQ ID NO: 1 with an Alanine residue. In some embodiments, a mutant *E. coli* endonulcase V comprising the amino acid sequence of SEQ ID NO: 2, or its conservative variants are provided. In some other embodiments, a mutant *Archaeoglobus fulgidus* (*A. fulgidus* or Afu), comprising the amino acid sequence of SEQ ID NO: 3, or its conservative variants are provided. The amino acid sequence of the mutant *Archaeoglobus fulgidus* endonuclease V is a modified sequence of SEQ ID NO: 56, wherein the modification is a replacement of a Tyrosine residue at the $74^{th}$ position of the SEQ ID NO: 56 with an Alanine residue.

In some embodiments, a nucleic acid assay is disclosed that includes providing a target DNA, a DNA polymerase and a mutant endonuclease V that is capable of nicking an inosine-containing strand of a double stranded DNA at a residue 3' to the inosine residue when the inosine residue is base-paired with a cytosine residue. A double stranded DNA is then generated from the target DNA, wherein the double stranded DNA comprises an inosine residue base-paired with a cytosine residue. The inosine-containing strand of the double stranded is subsequently nicked employing the mutant endonuclease V to generate a nicked DNA. The nucleic assay then includes conducting a DNA polymerase reaction on the nicked DNA employing the DNA polymerase.

DRAWINGS

These and other features, aspects and advantages of the present invention will become better understood when the following detailed description is read with reference to the accompanying figures.

FIG. 1 shows a general scheme for inosine-based amplicon production.

FIG. 2 depicts several nucleic acid synthesis schemes that employ an endonuclease V presented as a single series. The synthesis schemes shown in FIG. 2 provide methods for generating plus strands from a target DNA using a forward primer (hereinafter referred as "Ping" product); generating minus strands using a reverse primer (hereinafter referred as "Pong" product); addition of a promoter to the DNA product using an extender template; and generating RNA products using an RNA polymerase capable of initiating synthesis at the promoter that was added with the extender template.

FIG. 5 depicts amplicon production using multiple sets of nested primers in several different reaction mixtures as described in Example 4.

FIG. 6A shows a gel with the DNA products and FIG. 6B shows a gel with the RNA products.

Figure 12:
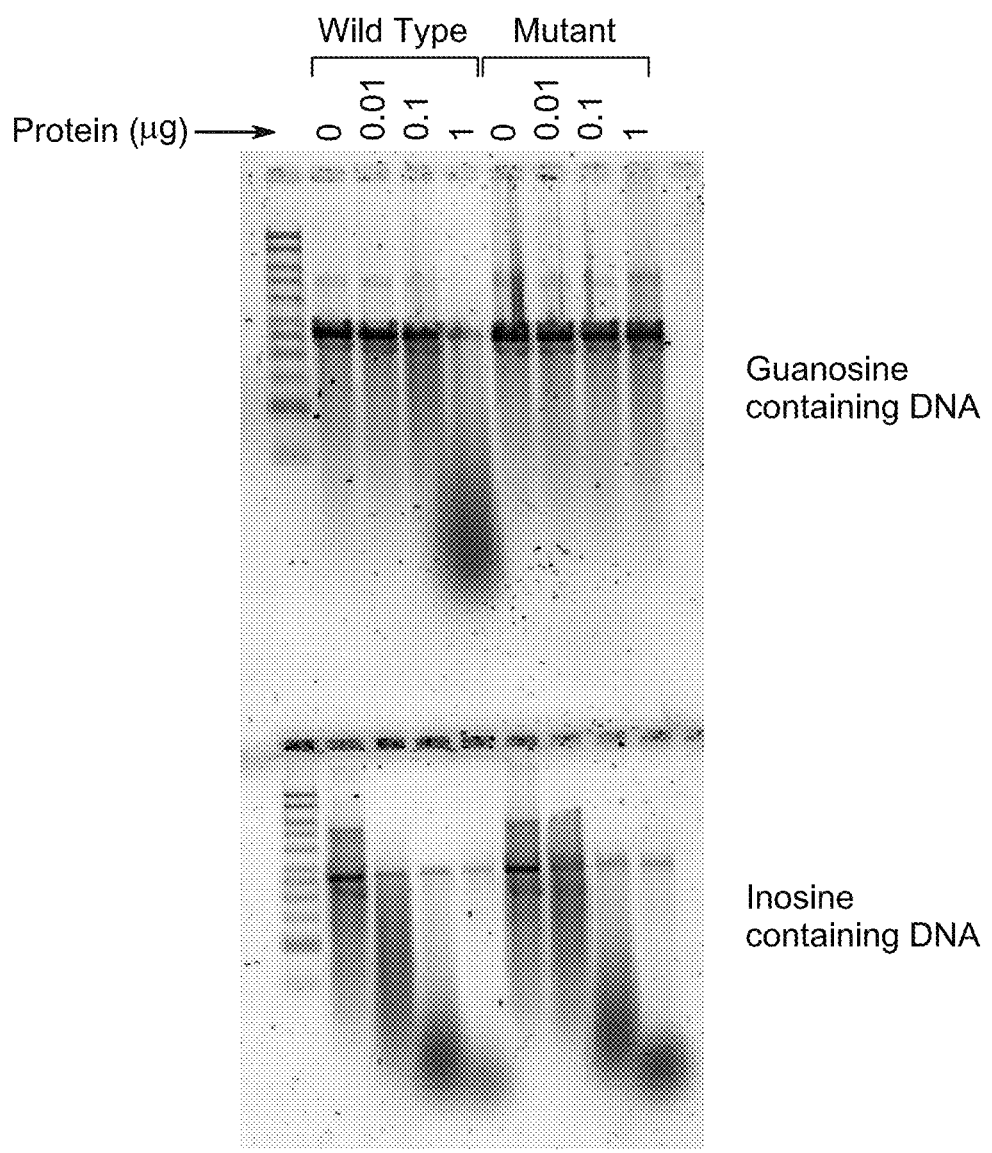

FIG. 12 demonstrates that both WT and mutant endonuclease V nucleases act on inosine-containing DNA but substantially not on the guanine-containing DNA as described in Example 13.

Figure 13:
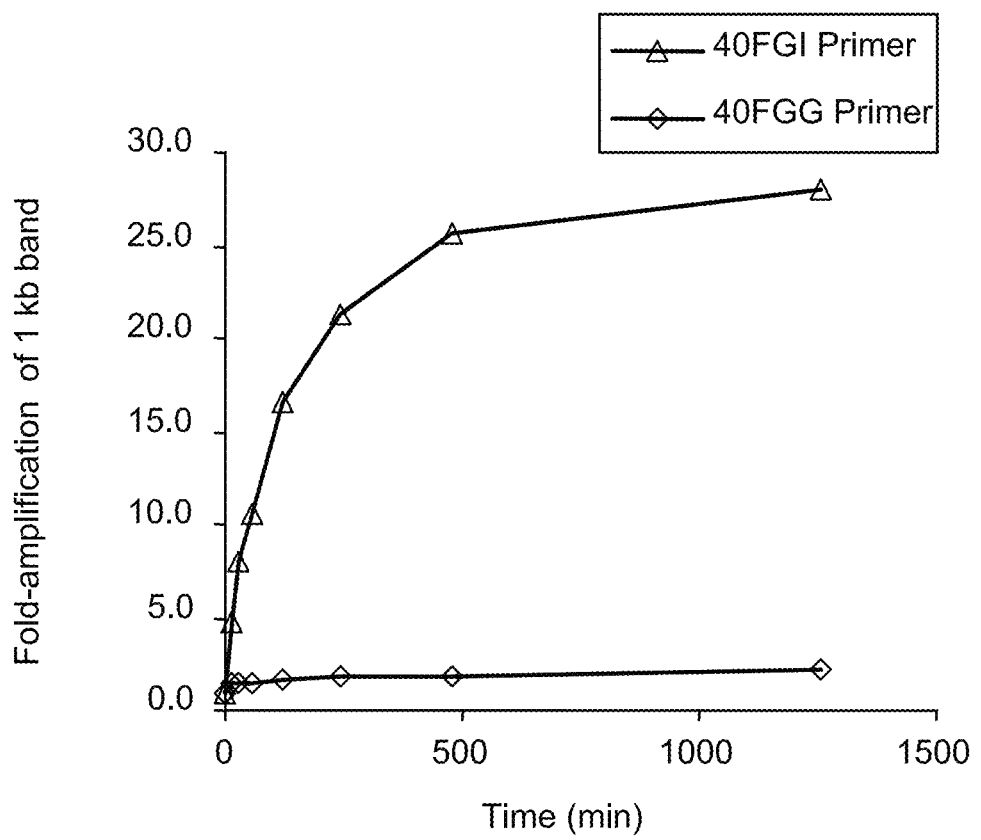

FIG. 13 demonstrates that the nuclease/polymerase combination (Y75A mutant *E. coli* endonuclease V and exo 9-) Bst polymerase) generates amplicon DNA from inosine-containing DNA but not on the guanine-containing DNA as described in the Example 14.

Figure 14:
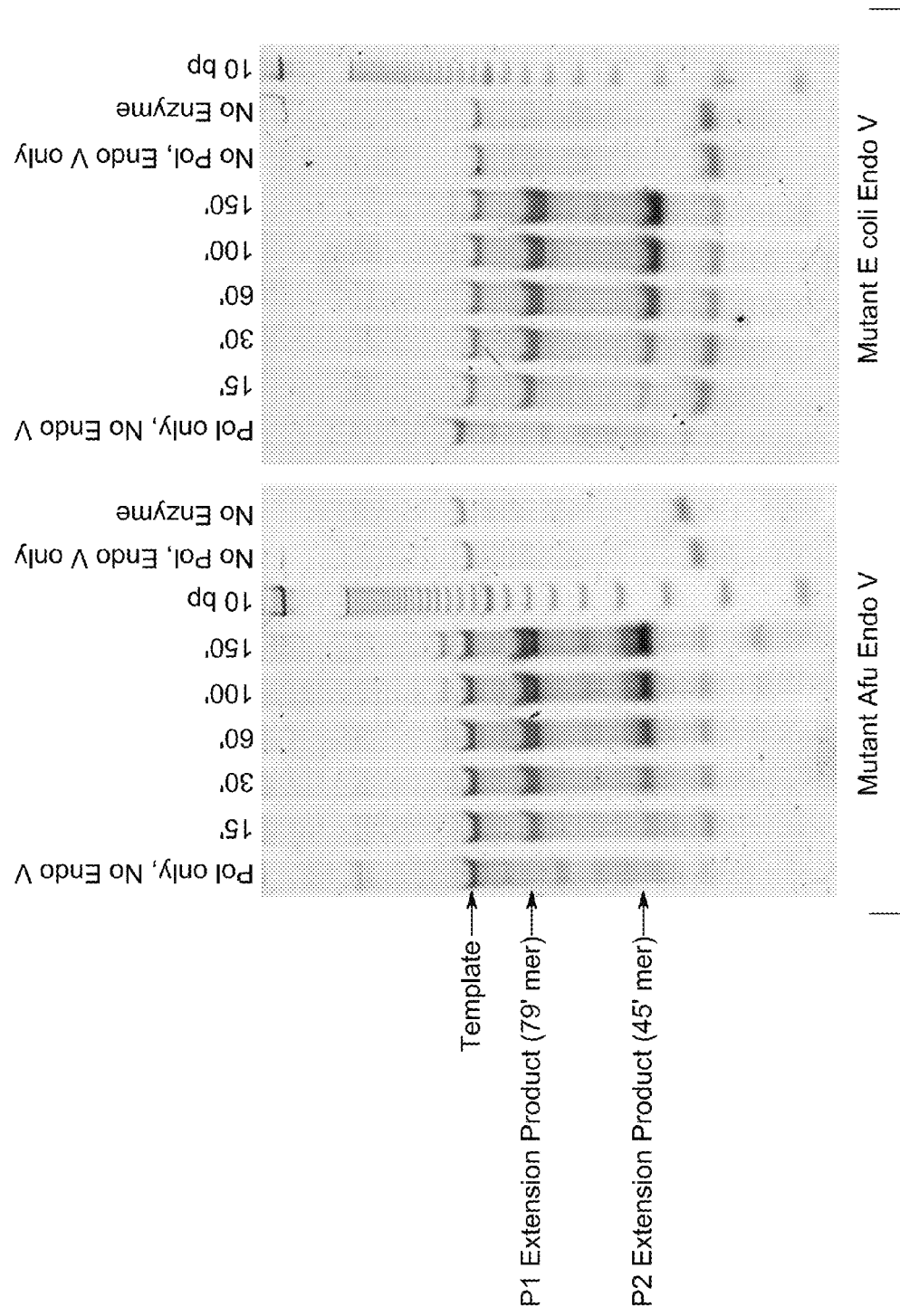

FIG. 14 depicts the results of a series of experiments that demonstrate the ability of the Y74A mutant *A. fulgidus* (Aft) endonuclease V (SEQ ID NO: 3, wherein the Tyrosine residue at the $74^{th}$ position of WT Afu endo V is replaced with an Alanine residue) and the Y75A mutant *E. coli* endonuclease V (SEQ ID NO: 2, wherein a Tyrosine residue at the $75^{th}$ position of WT *E. coli* endo V (SEQ ID No: 1) is replaced with an Alanine residue) to function with polymerase to generate amplicon from a target DNA as described in Example 15.

Figure 15:
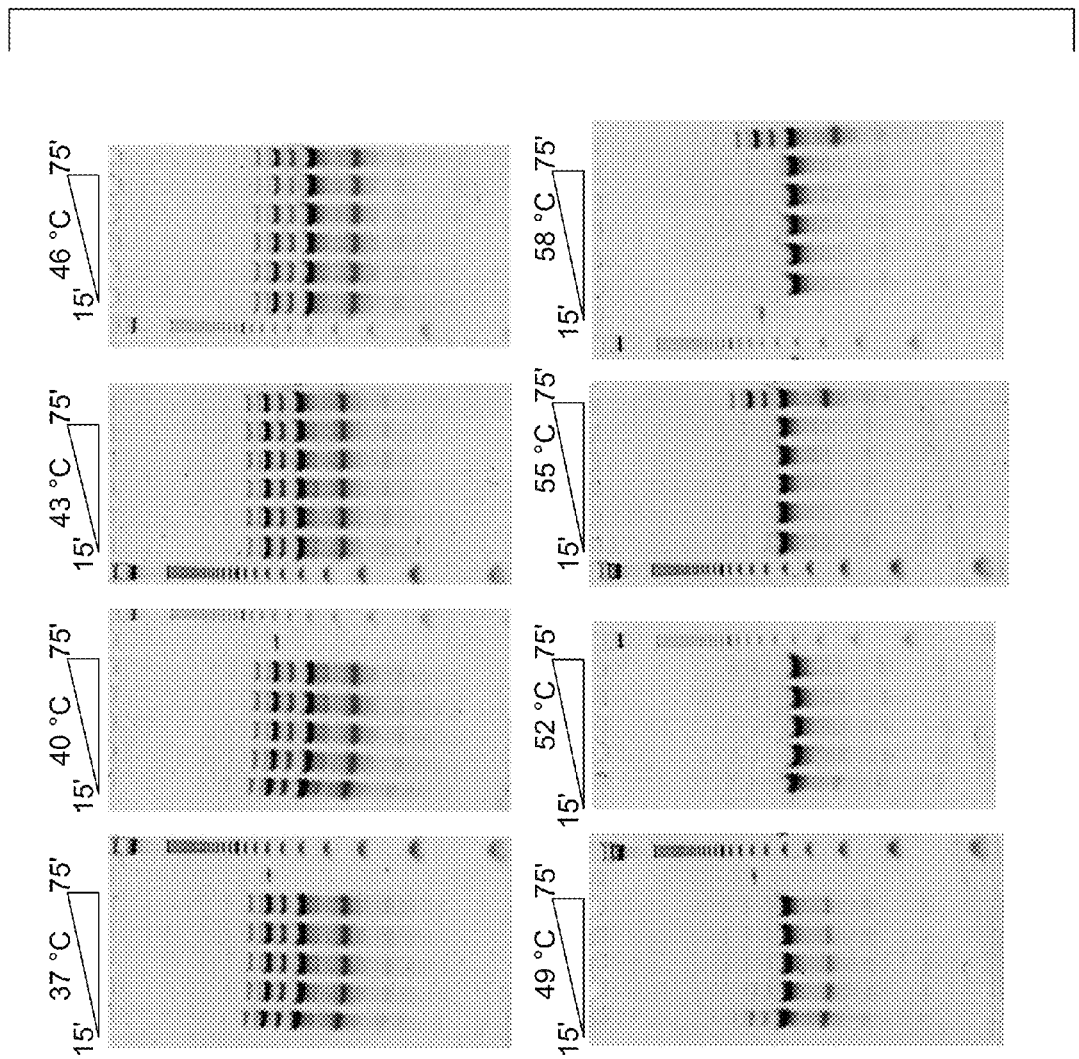

FIG. 15 shows the thermal stability of the Y75A mutant *E. coli* endonuclease V (SEQ ID NO:2) at a variety of temperatures as described in Example 16.

Figure 16:
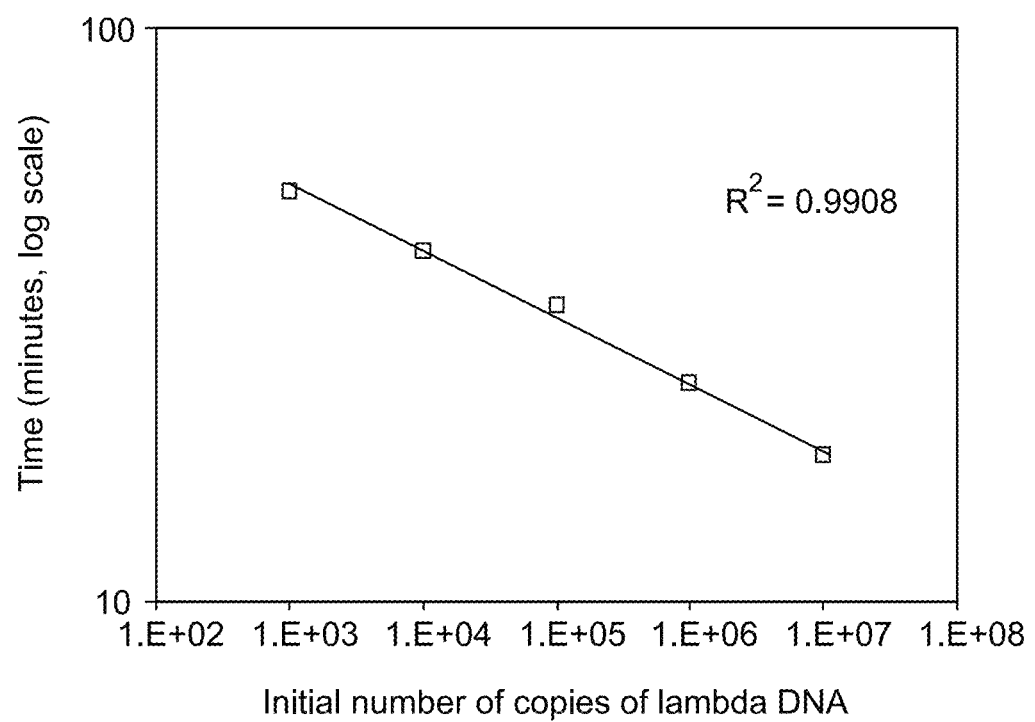

FIG. 16 shows the results of real-time DNA amplification as described in Example 17.

Figure 17:
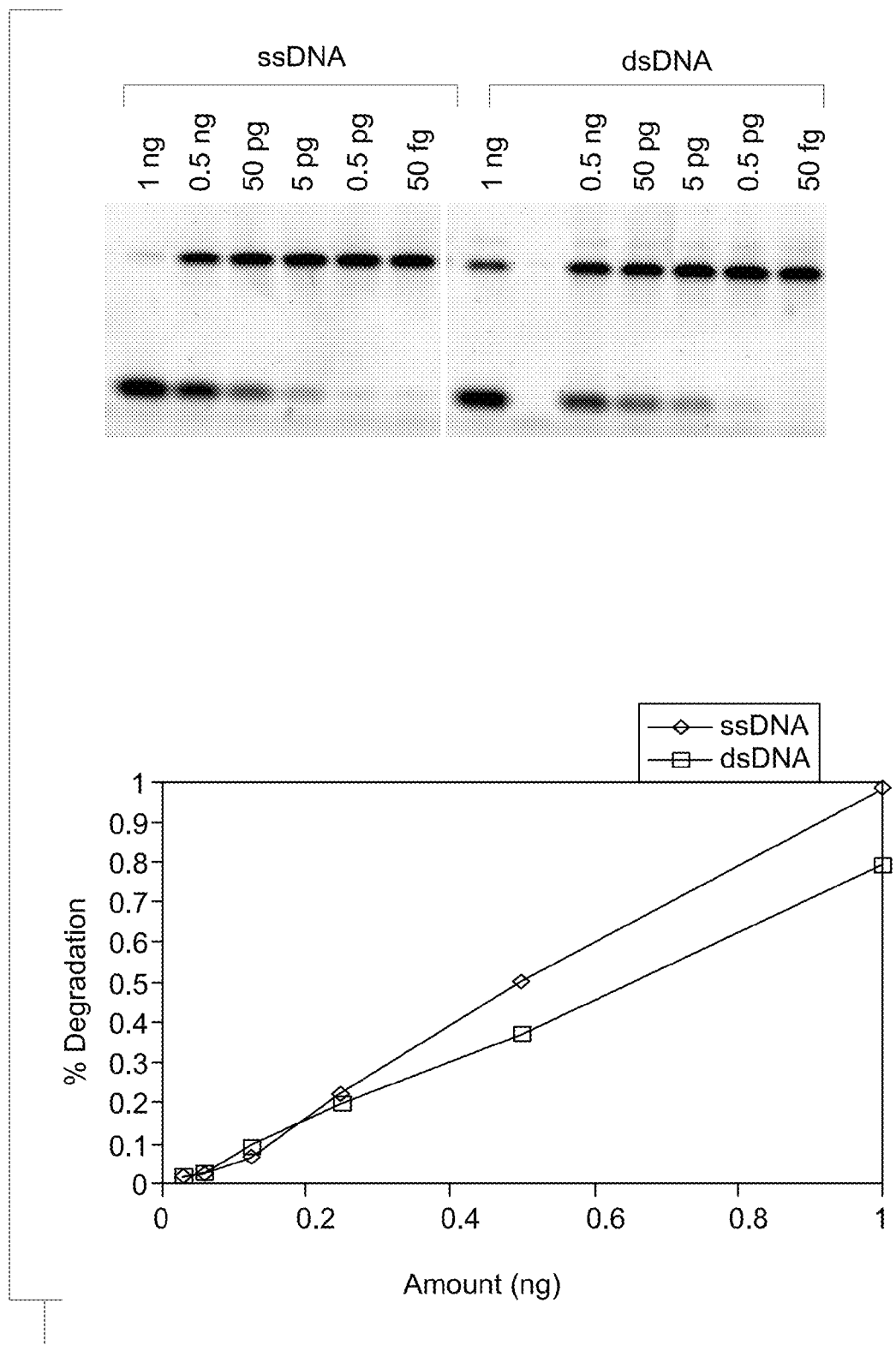

FIG. 17 shows the Y80A mutant Tma endonuclease V (SEQ ID NO: 58) activity on single stranded DNA and double stranded DNA as described in Example 18.

Figure 18:
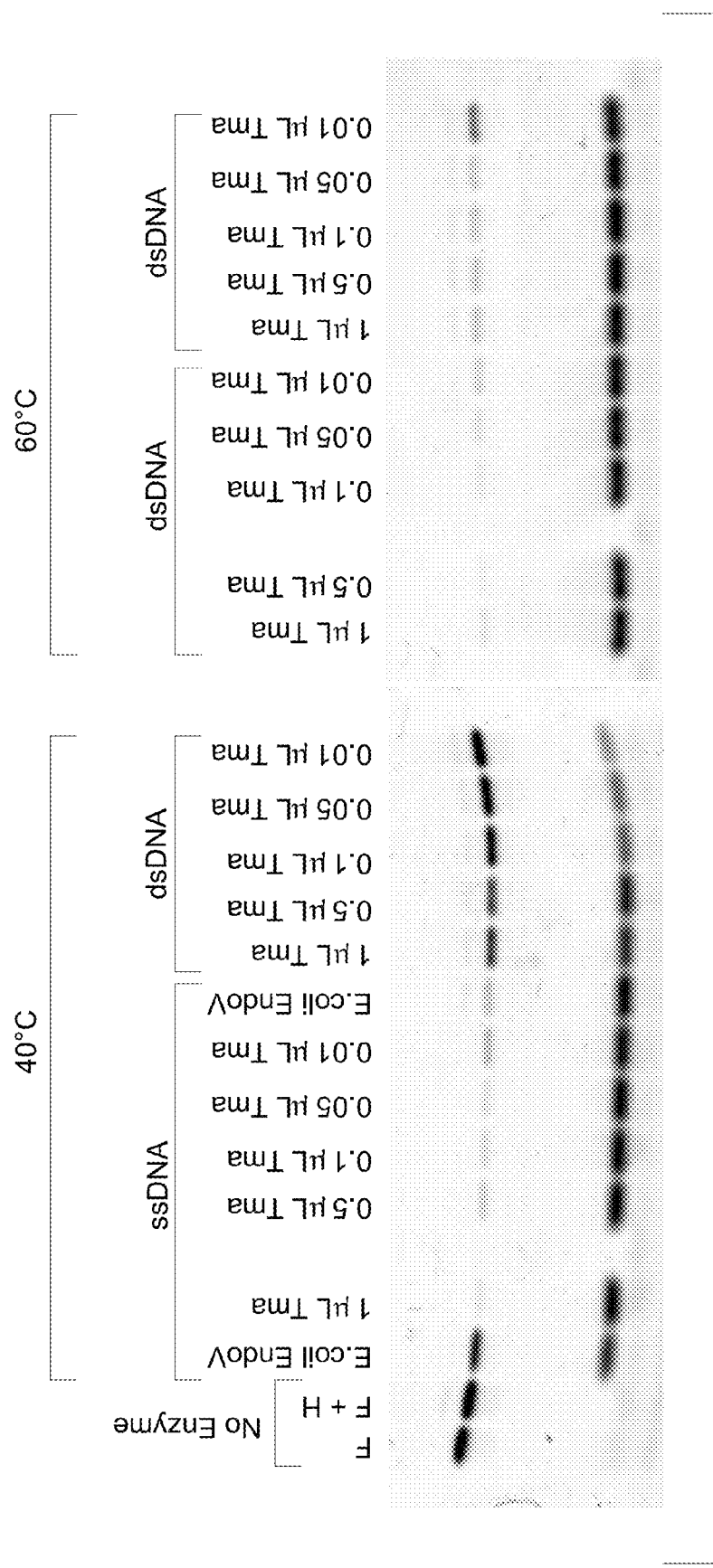

FIG. 18 shows the nicking efficiency of Tma endonuclease V on double stranded DNA and single stranded DNA at 45 C and 60 C as described in Example 19.

Figure 19:
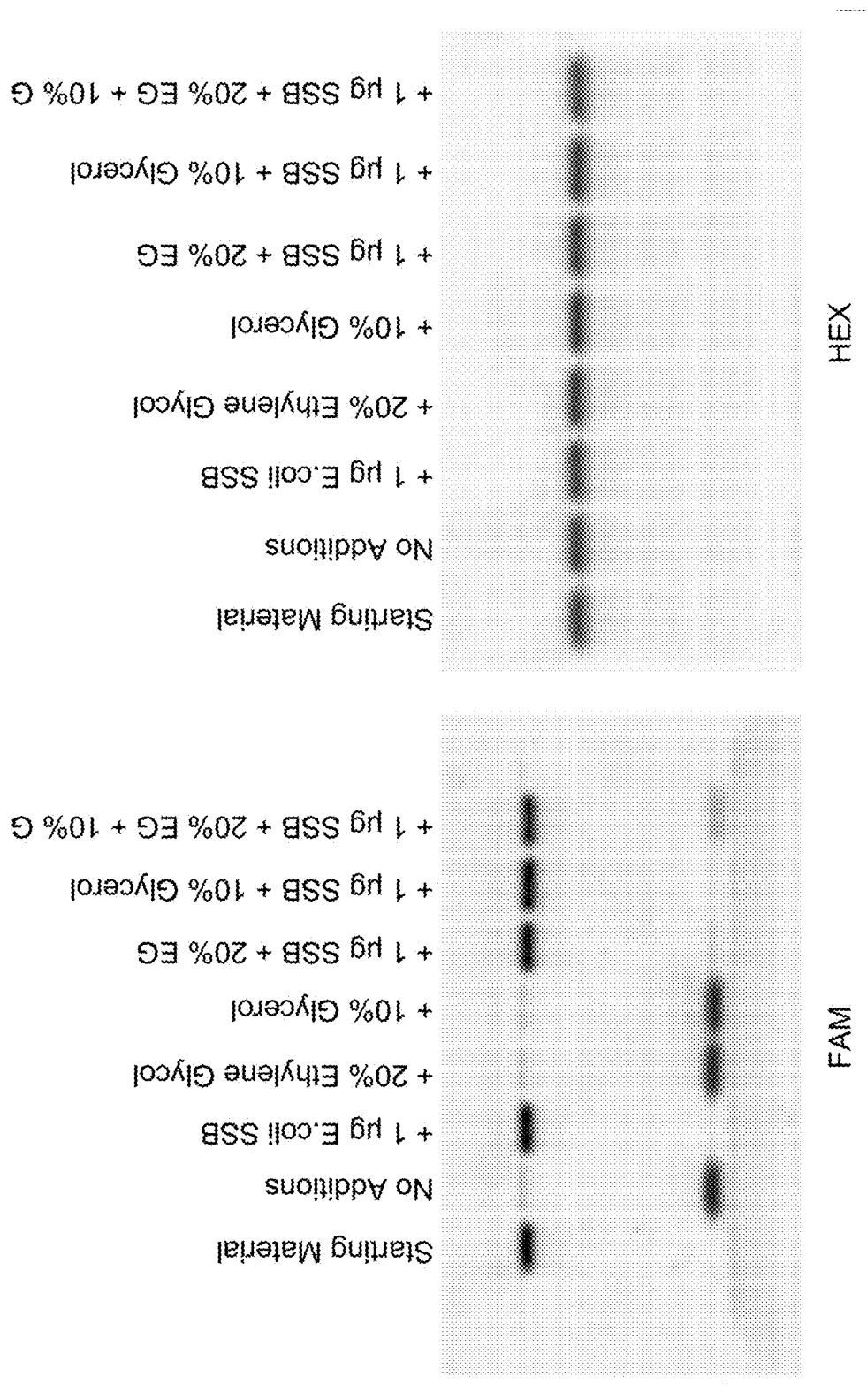

FIG. 19 shows the nicking efficiency of Tma endonuclease V on double stranded DNA at 60° C. as described in Example 20.

Figure 20:
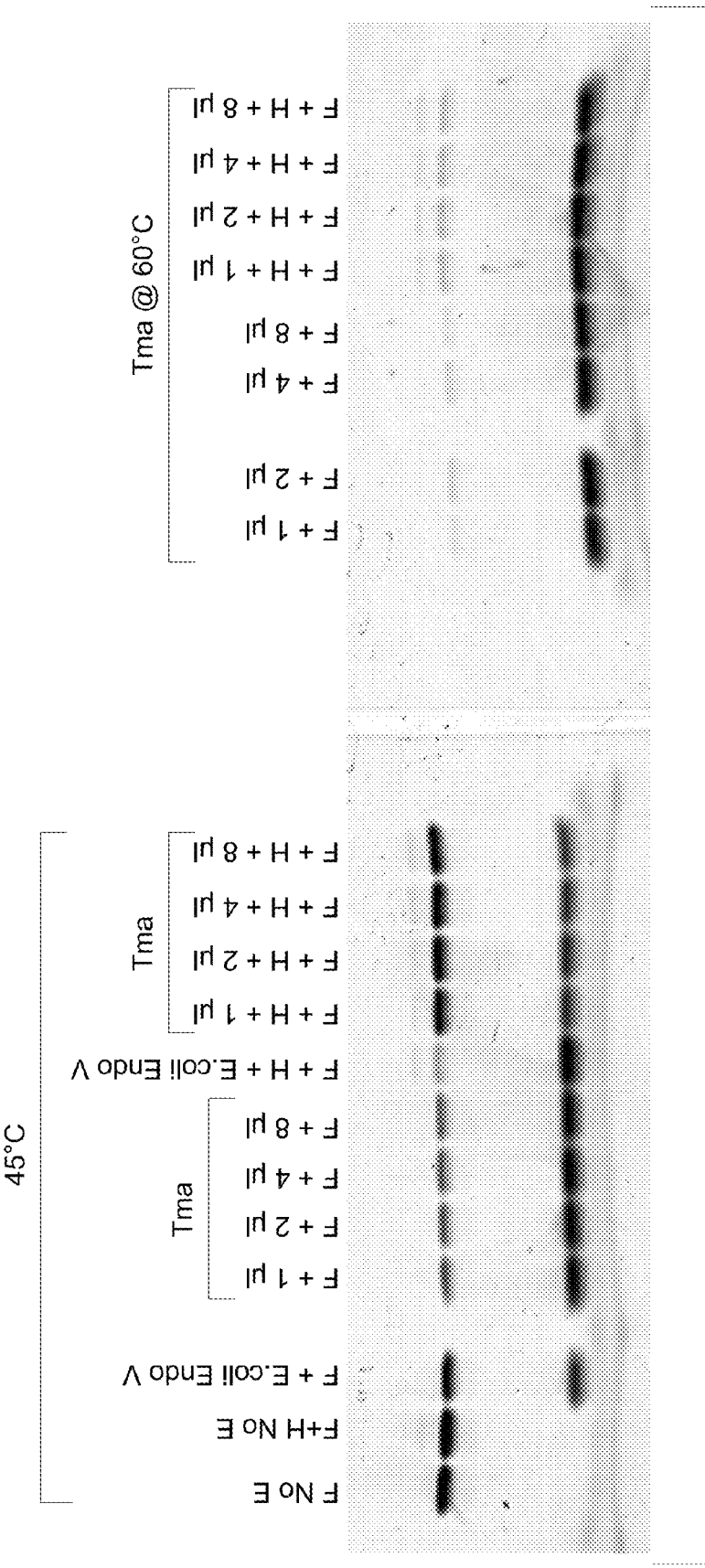

FIG. 20 shows the nicking efficiencies of Y75A mutant *E. coli* endonuclease V (SEQ ID NO: 2) and Y80A mutant *Termotoga maritima* (Tma) endonuclease V (SEQ ID NO: 58) as described in Example 21.

Figure 21:
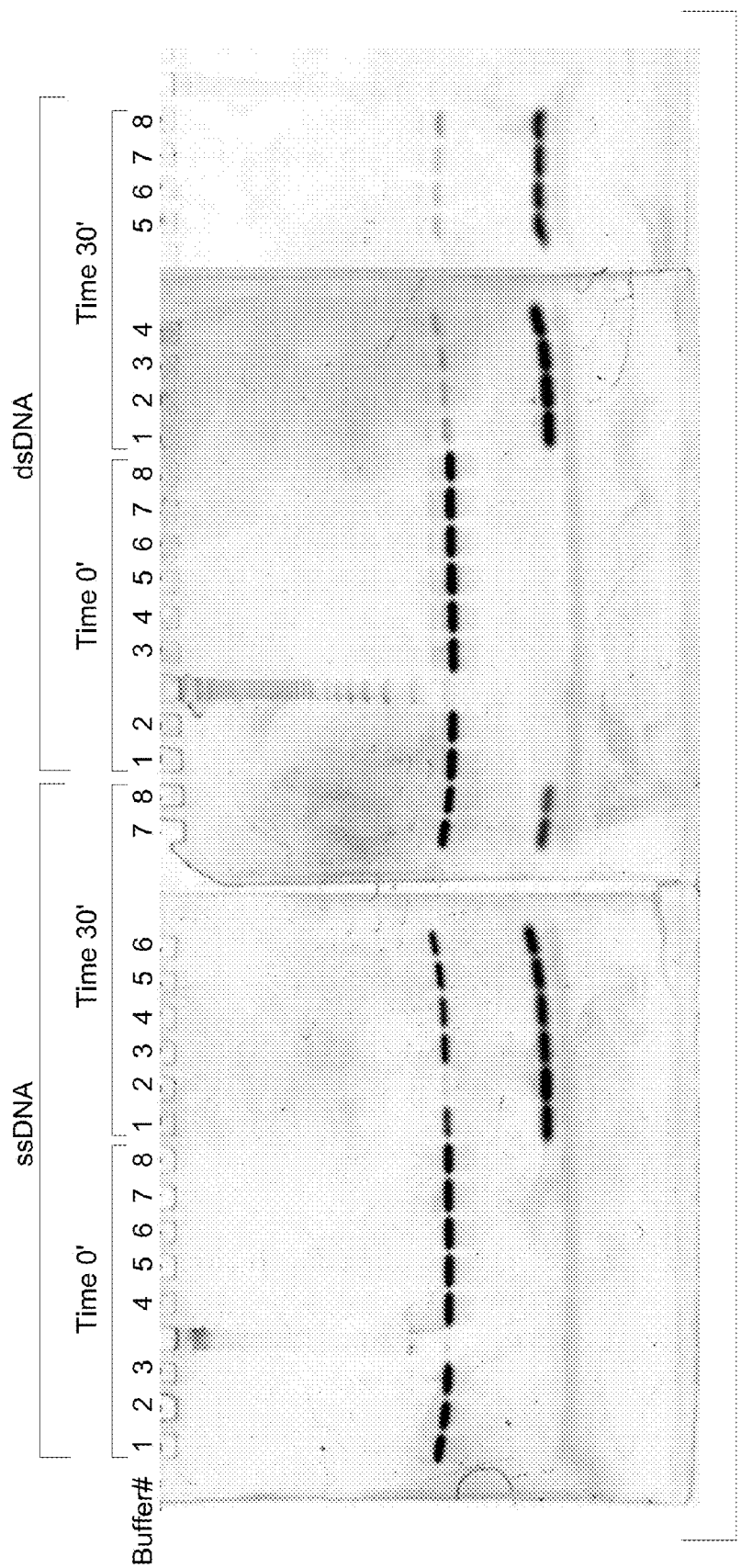

FIG. 21 shows the nicking efficiencies of Y75A mutant *E. coli* endonuclease V (SEQ ID NO: 2) on single stranded DNA and double stranded DNA in various buffers as described in Example 22.

DETAILED DESCRIPTION

The following detailed description is exemplary and not intended to limit the invention of the application and uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Where necessary, ranges have been supplied, and those ranges are inclusive of all sub-ranges there between. To more clearly and concisely describe and point out the subject matter of the claimed invention, the following definitions are provided for specific terms, which are used in the following description and the appended claims.

As used herein, the term "biological sample" refers to a sample obtained from a biological subject. It includes samples obtained in vivo or in vitro. Biological sample includes, but are not limited to, body fluid (e.g., blood, blood plasma, serum, or urine), organs, tissues, fractions and sections (e.g., sectional portions of an organ or tissue) and cells isolated from a biological subject or from a particular region (e.g., a region containing diseased cells) of a biological subject. The biological sample contains or is suspected to contain a target nucleic acid. The biological sample may be of eukaryotic origin, prokaryotic origin, viral origin or bacteriophage origin. Biological sample may be obtained from an insect, a protozoa, a bird, a fish, a reptile, a mammal (e.g., rat, mouse, cow, dog, guinea pig, or rabbit), or a primate (e.g., chimpanzee or human). Biological samples may be dispersed in solution or may be immobilized on a solid support, such as in blots, assays, arrays, glass slides, microtiter, or ELISA plates.

As used herein, the term "target DNA" refers to a DNA sequence of natural or synthetic origin that may be synthesized or amplified using one of more of the methods of the present invention. The term "target DNA template" refers to a portion of the target DNA that may be used by a DNA polymerase to produce one or more amplicons.

As used herein, the term "complementary", when used to describe a first nucleic acid/oligonucleotide sequence in relation to a second nucleic acid/oligonucleotide sequence, refers to the ability of a polynucleotide or oligonucleotide comprising the first nucleic acid/oligonucleotide sequence to hybridize (e.g., to form a duplex structure) under certain hybridization conditions with an oligonucleotide or polynucleotide comprising the second nucleic acid/oligonucleotide sequence. Hybridization occurs via base pairing of nucleotides (complementary nucleotides). Base pairing of the nucleotides may occur via Watson-Crick base pairing, non-Watson-Crick base pairing or base pairing formed by non-natural/modified nucleotides. For example, an adenine (A) base in an adenosine is capable of base paring with a thymine (T) base in a thymidine; and a guanine (G) base in a guanosine is capable of base pairing with a cytosine (C) base in a cytidine via Watson-Crick hydrogen bonding. Thus A is considered to be complementary to T, and G is considered to be complimentary to C. If a nucleotide at a certain position of a first oligonucleotide strand is capable of hydrogen bonding with a nucleotide at a corresponding position of a second oligonucleotide strand, then the two oligonucleotide strands are considered to be complementary to each other at that position. Two oligonucleotide strands are considered complementary to each other as a whole when a sufficient number of corresponding positions in each of the two oligonucleotides have nucleotides that hydrogen bond with each other.

As used herein, the term "dNTP mixture" refers to a mixture of deoxynucleotide triphosphates that act as precursors required by a DNA polymerase for DNA synthesis. Each of the deoxynucleotide triphosphates in a dNTP mixture comprises a deoxyribose sugar, an organic base, and a phosphate in a triphosphate form. A dNTP mixture may include each of the naturally occurring deoxynucleotide triphosphate (e.g., dATP, dTTP, dGTP, dCTP or dUTP). In some embodiments, each of the naturally occurring deoxynucleotide triphosphates may be replaced or supplemented with a synthetic analog; provided however that inosine base may not replace or supplement guanosine base (G) in a dNTP mixture. Each of deoxynucleotide triphosphate in dNTP may be present in the reaction mixture at a final concentration of 10 μM to 20,000 μM, 100 μM to 1000 μM, or 200 μM to 300 μM.

As used herein, the term "inosine" or "inosine residue" refers to a 2'-deoxyribonucleoside or 2'-ribonucleoside residue wherein the nucleobase is a hypoxanthine. Xanthine structures are alternate structures to inosine residues, resulting from deamination of guanine. The inosine residue is capable of base pairing with a thymine, a cytidine or a uridine residue. The term "inosine analog" refers to a 2'-deoxyribonucleoside or 2'-ribonucleoside wherein the nucleobase includes a modified base such as xanthine, uridine, oxanine (oxanosine), other O-1 purine analogs, N-6-hydroxylaminopurine, nebularine, 7-deaza hypoxanthine, other 7-deazapurines, and 2-methyl purines. The term "inosine-containing primer" refers to a primer sequence including at least one inosine residue. In some embodiments, the inosine-containing primer may comprise an inosine analog, including xanthine. A nucleic acid sequence containing inosine or inosine analogue residue as referred herein are recognized and cleaved by an endonuclease V.

As used herein, the term "amplicon" refers to nucleic acid amplification products that result from the amplification of a target nucleic acid. Amplicons may comprise a mixture of amplification products (i.e., a mixed amplicon population), several dominant species of amplification products (i.e., multiple, discrete amplicons), or a single dominant species of amplification product. A single species of amplicon may be isolated from a mixed population of amplicons using art-recognized techniques, such as affinity purification or electrophoresis. An amplicon may comprise single-stranded or double-stranded DNA, DNA:RNA hybrids, or RNA depending on the reaction scheme used. An amplicon may be largely single-stranded or partially double-stranded or completely double-stranded DNA, DNA:RNA hybrids, or RNA.

As used herein, the term "primer", or "primer sequence" refers to a short linear oligonucleotide that hybridizes to a target nucleic acid sequence (e.g., a target DNA template to be amplified) to prime a nucleic acid synthesis reaction. The primer may be a RNA oligonucleotide, a DNA oligonucleotide, or a chimeric sequence. The primer may contain natural, synthetic, or modified nucleotides. For example, the primer may comprise naturally occurring nucleotides (G, A, C or T nucleotides) or their analogues. Suitable primers may also include at least one inosine residue (e.g., inosine-containing primer) positioned near the 3' terminal end of the primer (e.g., as penultimate nucleotide at the 3' end of a primer sequence). Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long. In some embodiments the primer ranges in length from 5 nucleotides to 25 nucleotides. As used herein the term "forward primer" refers to a primer that anneals to a first strand of the target DNA and the term "reverse primer" refers to a primer that anneals to a complimentary, second strand of the target DNA. Together a forward primer and a reverse primer are generally oriented on the target DNA sequence in a manner analogous to PCR primers, such that a DNA polymerase can initiate the DNA synthesis resulting in replication of both the strands.

As used herein, the term "melting temperature" of a primer refers to the temperature at which 50% of primer in a primer-DNA hybrid dissociates into free primer and DNA. The melting temperature of a primer increases with its length. The melting temperature of a primer also depends on its nucleotide composition. Thus primers with many G and C nucleotides will melt at a higher temperature than ones that only have A and T nucleotides. High melting temperatures (e.g., above 65° C.) and very high melting temperatures (e.g., above 80° C.), may be disfavored because some DNA polymerases denature and lose activity at such high temperatures. Because ionic strength also affects the melting temperature of a primer, all melting temperature values provided herein are determined at a pH of 7.7 with 5 mM $MgCl_2$ and 50 mM NaCl.

As used herein, the term "reducing agent" refers to agent that has capability to reduce disulfides to mercaptans. Suitable reducing agents may contain thiol groups such as dithiothreitol (DTT), 2-mercaptoethanol (βME), and 2-mercaptoethylamine (MEA). Alternatively, reducing agents may contain phosphines and their derivatives, for example, Tris (carboxyethyl) phosphine (TCEP).

As used herein, the term "single strand DNA binding protein", abbreviated as "SSB", refers to proteins that bind non-covalently to single stranded DNA with a higher affinity than to double stranded DNA. Suitable examples of single strand binding proteins include, but are not limited to, *E. coli* SSB, T4 gene 32 protein, T7 gene 2.5 protein, Ncp7, recA, or combinations thereof.

As used herein, the term "vector" refers to any autonomously replicating or integrating agent, including but not limited to, plasmids, cosmids, and viruses (including phage). The vector comprises a nucleic acid sequence to which one or more additional nucleic acid sequence of interest may be included. The vector may be an expression vector by which the amino acid sequences corresponding to the nucleic acid sequences of interest may be expressed in a suitable host. Vectors may be used both to amplify and to express DNA (e.g., genomic or cDNA) or RNA.

As used herein, the term "transformed cell" refers a cell into which (or a predecessor or an ancestor of which) a nucleic acid sequence encoding a polypeptide of interest has been introduced, by means of, for example, recombinant DNA techniques or viruses.

A "purified" or "isolated" polypeptide or polynucleotide is one that is substantially free of the materials with which it is generally associated in nature. By substantially free is meant at least 50%, preferably at least 70%, more preferably at least 80%, even more preferably at least 90% free of the materials with which it is associated in nature.

The term "conservative variants", as used herein, applies to both amino acid and nucleic acid sequences. With respect to particular nucleic acid sequences, the term "conservative variants" refers to those nucleic acids that encode identical or similar amino acid sequences (i.e., amino acid sequences that have similar physico-chemical properties) and include degenerate sequences. For example, the codons GCA, GCC, GCG, and GCU all encode alanine. Thus, at every amino acid position where an alanine is specified, any of these codons may be used interchangeably in constructing a corresponding nucleotide sequence. Such nucleic acid variants are conservative variants, since they encode the same protein (assuming that is the only alternation in the sequence). One skilled in the art recognizes that each codon in a nucleic acid, except for AUG (sole codon for methionine) and UGG (tryptophan), may be modified conservatively to yield a functionally identical peptide or protein molecule. As to amino acid sequences, one skilled in the art will recognize that alteration of a polypeptide or protein sequence via substitutions, deletions, or additions of a single amino acid or a small number (typically less than about ten) of amino acids may be a "conservative variant" if the physico-chemical properties of the altered polypeptide or protein sequence is similar to the original. In some cases, the alteration may be a substitution of one amino acid with a chemically similar amino acid. Examples of conservative variants include, but not limited to, the substitution of one hydrophobic residue (e.g., isoleucine, valine, leucine or methionine) for one another; or the substitution of one polar residue for another (e.g., the substitution of arginine for lysine, glutamic for aspartic acid, or glutamine for asparagine) and the like. Genetically encoded amino acids generally may be divided into four families: (1) acidic: aspartate, glutamate; (2) basic: lysine, arginine, histidine; (3) nonpolar: alanine, valine, leucine, isoleucine, proline, phenylalanine, methionine, tryptophan; and (4) uncharged polar: glycine, asparagine, glutamine, cysteine, serine, threonine, tyrosine.

The term "mutant endonuclease" or "engineered endonuclease" as used herein refers to an endonuclease enzyme that is generated by genetic engineering or protein engineering, wherein one more amino acid residues are altered from the wild type endonuclease. The alteration may include a substitution, a deletion or an insertion one or more amino acid residues. Throughout the specification and claims, the substitution of an amino acid at one particular location in the protein sequence is referred using a notation "(amino acid residue in wild type enzyme)(location of the amino acid in wild type enzyme)(amino acid residue in engineered enzyme)". For example, a notation Y75A refers to a substitution of a Tyrosine (Y) residue at the $75^{th}$ position of the wild type enzyme by an Alanine (A) residue (in mutant/engineered enzyme)

One or more embodiments of the present invention provide compositions, methods and kits for various nucleic acid assays, wherein an endonuclease that is capable of nicking an inosine-containing strand of a double-stranded nucleic acid at a location 3' to the inosine residue is employed. In some embodiments, the endonuclease is a genetically engineered endonuclease.

For nucleic acid assays, samples suspected or known to contain a particular target nucleic acid sequence may be obtained from a variety of sources. The sample may be, for example, a biological sample, a food, an agricultural sample, or an environmental sample. Samples may also be derived from a variety of biological subjects. The biological subject may be of prokaryotic or eukaryotic origin and includes viruses. The sample may be derived from a biological tissue or a body fluid or an exudate (e.g., blood, plasma, serum or urine, milk, cerebrospinal fluid, pleural fluid, lymph, tears, sputum, saliva, stool, lung aspirates, throat or genital swabs, and the like), whole cells, cell fractions, or cultures.

The target nucleic acid for a nucleic acid assay may be dispersed in solution or immobilized on a solid support (such as blots, arrays, microtiter, or well plates). A sample may be pretreated to make the target nucleic acid available for hybridization. For example, when a target nucleic acid is in a double stranded form, it may be denatured to generate a single stranded form of the target DNA. The target double stranded DNA may be thermally denatured, chemically denatured, or both thermally and chemically denatured. In some embodiments, the double stranded DNA is chemically denatured using a denaturant (e.g., glycerol, ethylene glycol, formamide, or a combination thereof) that reduces the melting temperature of double stranded DNA. In certain embodiments, the denaturant reduces the melting temperature by 5° C. to 6° C. for every 10% (vol./vol.) of the denaturant added to the reaction mixture. The denaturant or combination of denaturants may comprise 1%, 5%, 10% (vol./vol.), 15% (vol./vol.), 20% (vol./vol.), or 25% (vol./vol.) of reaction mixture. In certain embodiments, the denaturant comprises ethylene glycol. In alternative embodiments, the denaturant is a combination of glycerol (e.g., 10%) and ethylene glycol (e.g., 6% to 7%). Salts that reduce hybridization stringency may be included in the reaction buffers at low concentrations to chemically denature the target DNA is at low temperatures. In embodiments where the target DNA is thermally denatured the denaturing step comprises thermally denaturing the target DNA (e.g., by heating the target DNA at 95° C.).

In some embodiments, a DNA amplification method is provided, wherein a target DNA is hybridized with an inosine-containing primer followed by amplification of the target DNA using a DNA polymerase (e.g., a strand displacement polymerase or a reverse transcriptase), deoxyribonucleotides (dNTPs) and an endonuclease. The dNTPs provides a combination of deoxyribonucleotides required by a DNA polymerase for DNA synthesis. DNA polymerases use dNTP mixture to add nucleotides to the 3' end of a primer based on a template strand of DNA in a complementary fashion, creating a new DNA strand complementary to the target DNA template. The dNTP mixture may include each of the naturally occurring deoxynucleotide bases (i.e., adenine (A), guanine (G), cytosine (C), and Thymine (T)). In some embodiments, each of the naturally occurring deoxynucleotides may be replaced or supplemented with a synthetic analog; provided however that deoxyinosinetriphosphate may not replace or supplement dGTP in the dNTP mixture. The product of DNA amplification reaction may be single stranded or double-stranded DNA, often extending to the end of the template strand. The inosine nucleotide in the inosine-containing primer may be positioned at least 4 nucleotides, at least 5 nucleotides, or at least 10 nucleotides from the 5' end of the inosine-containing primer. In certain embodiments, the inosine nucleotide may be the penultimate 3' nucleotide of the primer. In alternative embodiments, inosine may be present at both the penultimate 3' residue and ultimate 3' residue. In some embodiments, the inosine-containing primer comprises an inosine analogue.

Figure 1:
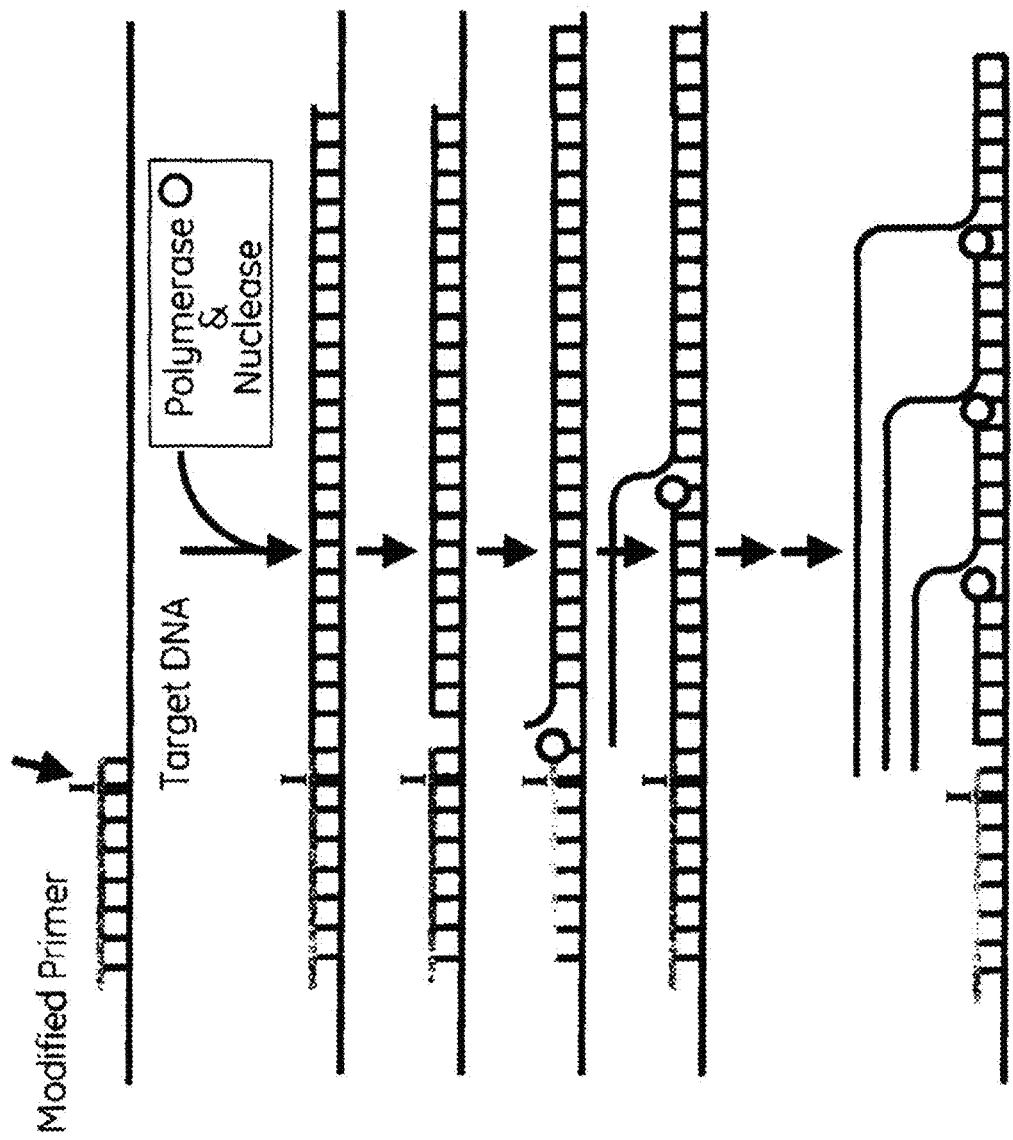

In some embodiments, an endonuclease, in combination with a strand displacing DNA polymerase and an inosine-containing primer is used for amplification of a target DNA (see FIG. 1 for a schematic representation of a nucleic acid amplification). Upon binding of inosine-containing primer to the target DNA, the DNA polymerase (e.g., Phi29 DNA polymerase) extends the inosine-containing primer, generating a double stranded DNA (primer extension product) and thereby creating a nicking site for the endonuclease. The endonuclease nicks the double stranded DNA at this nicking site. Nicking creates a DNA synthesis initiation site for the DNA polymerase. The DNA polymerase binds to this initiation site and further elongates the nicked primer, displacing a single-stranded DNA product while it re-creates the double-stranded primer extension product. The cycle repeats, synthesizing multiple single strands of DNA complementary to the downstream portion of the target DNA template.

The schematic representation of a nucleic acid amplification shown in FIG. 1 may be varied by employing additional primers or other oligonucleotides, additional enzymes, additional nucleotides, stains, dyes, or other labeled components. For example, amplification with a single primer may be used for dideoxy sequencing, producing multiple sequencing products for each molecule of template, and, optionally by the addition of dye-labeled dideoxynucleotide terminators. Labeled probes may be generated from double-stranded cDNA made with a sequence-tagged oligo dT primer from mRNA samples. A single primer may be the complement of the tag sequence, facilitating identification and/or isolation.

In some embodiments, a strand displacement DNA polymerase, an endonuclease V and inosine-containing primers are employed in a DNA amplification reaction. Endonuclease V is a repair enzyme that recognizes DNA containing inosines (or inosine analogues) and hydrolyzes the second or third phosphodiester bonds 3' to the inosine (i.e., specifically nicks a DNA at a position two nucleotides 3' to an inosine nucleotide) leaving a nick with 3'-hydroxyl and 5'-phosphate. When the target DNA is double stranded the nick occurs in the strand comprising the inosine residue. For DNA amplification, the inosine-containing primer hybridizes with the target DNA. Inosine residue in the primer may base pair with a cytidine residue or a thymidine residue in the target DNA, wherein hypoxanthene substitutes for a guanine to complement a cytosine; or substitutes for an adenine to complement a thymine A complimentary strand to the target DNA template is then generated by DNA synthesis thereby generating a double-stranded DNA. Generation of the double stranded DNA in turn generates a nicking site for the endonuclease V. The endonuclease V nicks the inosine-containing strand of this double-stranded DNA. The DNA polymerase repeatedly generates the complementary strand from the nicked position. In each cycle, the strand displacement DNA polymerase employed in these reactions displace the complementary strand that was generated in the previous cycle. The steps of hybridization, elongation, nicking and further elongation may occur substantially simultaneously. Thus, one or more embodiments of the present invention provides methods wherein an inosine residue is introduced into a specific position of a target nucleic acid (via an oligonucleotide primer), followed by repeated generation of complimentary strand of the target nucleic acid using a polymerase and an endonuclease V that nicks the generated double stranded nucleic acid at the inosine-containing strand to initiate a second cycle of complementary strand generation by the polymerase.

In some embodiments, the DNA amplification reaction is performed under isothermal conditions. The reaction temperature during an isothermal amplification reaction condition may range 1° C., 5° C., or 10° C. from a set temperature. In some embodiments, the reaction temperature of DNA amplification is held at 46° C. (±1° C.). Thermally stable endonucleases and thermally DNA polymerases may be used depending upon the reaction temperature of DNA amplification reaction.

Inosine-containing primers may be synthesized using any of the art-recognized synthesis techniques. Amplicons may be generated using a single inosine-containing primer, paired inosine-containing primers, or nested-paired inosine-containing primers. Primer design software such as "autodimer" may be employed to design a single primer or multiple primers capable of annealing to a nucleic acid and facilitating polymerase extension. The inosine-containing primer may be designed in such a way that the melting temperature of the primer is about 45° C. with a salt concentration of about 50 mM. In some embodiments, relatively short primers (e.g., 10-mers to 20-mers; more preferably 14-mers to 18-mers, most preferably 16-mers) may be employed.

In some embodiments, the inosine-containing primer is designed such that the inosine residue is positioned in the primer at a location complementary to a Cytosine base (C) in the target DNA. In some embodiments, the inosine appears as the penultimate 3' base of the primer. Because the reaction conditions (i.e., temperature and ionic strength) affect annealing of primer to target DNA, optimal positioning of the inosine in the primer may be adjusted according to the reaction conditions. In general, the inosine residue is positioned away from the 5' end of the prime such that the primer remains annealed to the target DNA after nicking by the endonuclease (i.e., the length of the nicked primer is sufficient to enable binding to the target DNA under the nucleic acid assay reaction conditions). Accordingly, the segment of the primer 5' of the inosine should have a melting temperature approximately equal to the reaction temperature at the chosen reaction conditions. In some embodiment, the inosine-containing primer may comprise more than one inosine residue or inosine analogues. If there are two template Gs in a row, two inosines may appear in the primer as the both the penultimate 3' and the final residues. In this case, nicking by the endonuclease 2 nucleotides 3' to either inosine residues would have the same effect of creating a nicked DNA strand. In some embodiments, the inosine-containing primer may demonstrate a melting temperature of 25° C. to 70° C., 30° C. to 65° C., or 40° C. to 55° C. in the reaction mixture. In some embodiments, the inosine-containing primer demonstrates a melting temperature of 45° C. in the reaction mixture.

Figure 2:
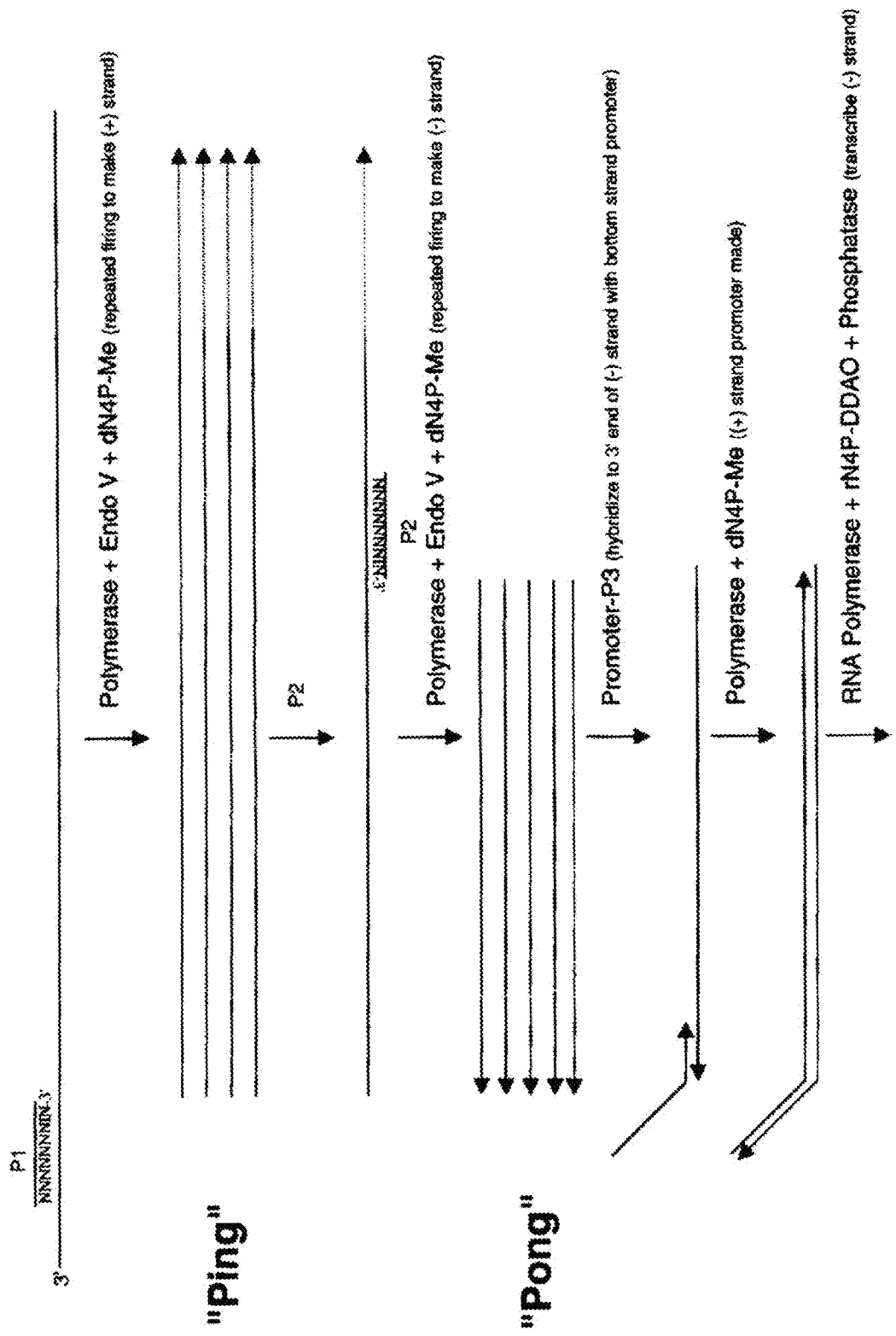
Figure 3:
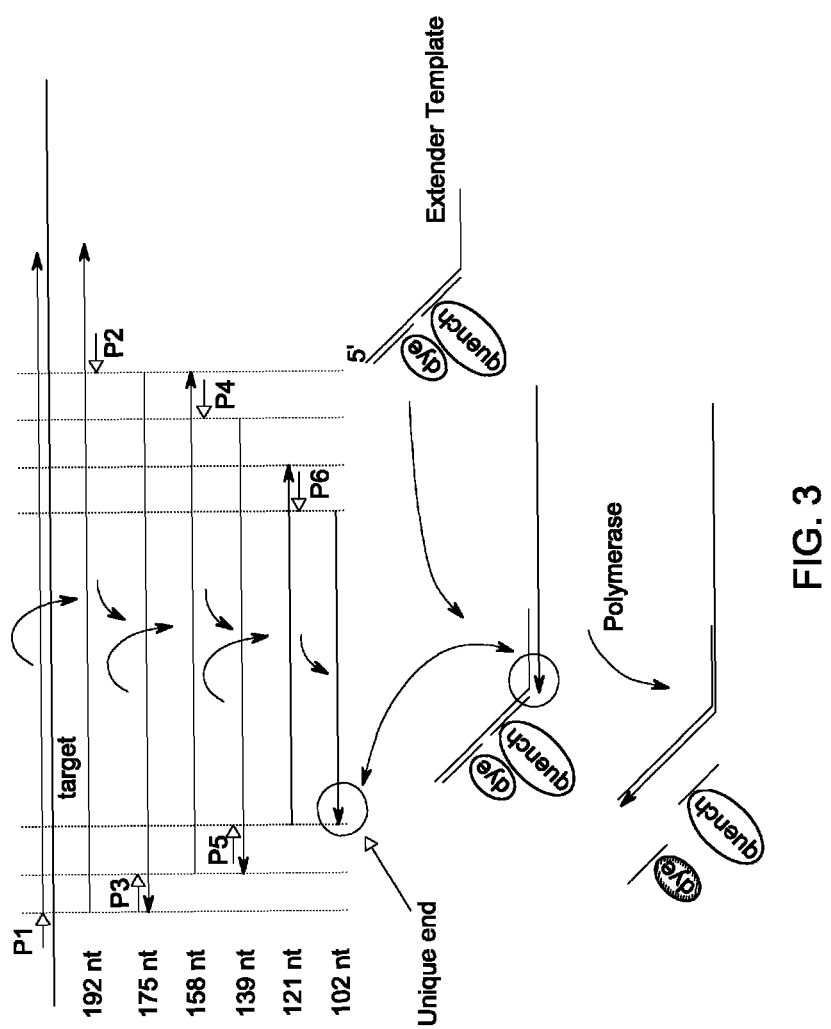
FIG. 3 shows a general scheme for detecting amplicons using paired fluorescent and quenching chromophores attached to oligonucleotides connected by hybridization to an extender template.

With a single, forward primer, the rate of synthesis of complimentary copies of target DNA is relatively constant, resulting in a steady, linear increase in the number of complimentary copies with time. Multiple primers may be included in the reaction mixture in some embodiments to accelerate the amplification process. Embodiments where both the plus and minus strands are generated, paired primers comprising a forward primer and a reverse primer may be included in the reaction mixture. For example, when a reverse primer (a primer that anneals to the generated complementary strand ((+) strand) to further generate a (−) strand in the reverse direction) that anneals to the complementary strand of target DNA at a defined distance from the forward primer is added (see, for example, FIG. 2), amplification process is accelerated. Since the targets for each of these primers would be present in the original template, both strands would be amplified in the two primer scheme (hereinafter referred as "Ping-Pong" reaction, "Ping product" being the amplicon of the forward primer and the "Pong product" being the amplicon of the reverse primer). The inclusion of multiple paired primers may improve the relative percentage of a discrete product in the reaction mixture. The forward and reverse primers may be placed relatively close to each other (i.e., less than about 1 kb apart), minimizing the time required to complete the forward amplicon ((+) strand) to its 5' end as defined by the endonuclease V cleavage site, and thereby reducing the total time required to generate amplicons from the target DNA. The reaction rate reaches a maximum when the amount of nuclease, polymerase, or any other component(s) becomes limiting. Additional pairs of nested primers (see, for example, FIG. 3) may also be used to further increase amplification rates. Nested primers may be designed to bind at or near the 3' end of the previous amplicon so that in a series, each primer in the series will hybridize next to each other on the original target. Where multiple nested primers are used, single stranded DNA binding protein (SSB) at a concentration of 1 ng to 1 µg in a 10 µL, volume may be included in the reaction mixture to increase fidelity and to reduce background.

Amplification with multiple, paired primers facilitates rapid and extensive amplification, which is useful to detect the presence of specific sequences, to quantify the amounts of those sequences present in a sample, or to produce quantities of a sequence for analysis by methods such as electrophoresis for size measurement, restriction enzyme digestion, sequencing, hybridization, or other molecular biological techniques.

In some embodiments, extender templates, which are specific primer sequences (e.g., Ones that generate a promoter sequence or a restriction endonuclease site specific sequence), may be annealed at the 3' end of the amplicon by incorporating in an inosine-containing primer. An extender template may be designed such that it anneals to the 3' end of an amplicon. If the extender template contains two stretches of sequences, one complementary to the amplicon, and one that is not, hybridization will create a 5' overhang of the non-complementary primer sequence. The 3' recessed end of the amplicon can then be further extended by the DNA polymerase. This extension reaction may be employed to incorporate specific DNA sequences at the 3' end of an amplicon.

In some embodiments, the 5' end of the extender template may contain a hairpin loop, with a fluorescent dye and a quencher located on either arm of the stem such that the dye fluorescence is largely quenched by resonance energy transfer. Upon extension of the recessed 3' end of the amplicon by a DNA polymerase, the stem-loop structure gets converted to a double stranded structure and causes the dye and the quencher to be separated further. This eliminates some or all of the fluorescence quenching, and thus generates a detectable signal. This signal may be multiplexed by appropriate sequence selection of the extender templates and the color of the quenched dyes so that 2 or more independent amplification processes may be monitored simultaneously.

In some embodiments the 5' end of the extender template may include the complement of an RNA polymerase promoter sequence. Thus, a double stranded RNA polymerase promoter may be generated by hybridization of extender template to the amplicon followed by extension of the recessed 3' end of the amplicon by the DNA polymerase. If an RNA polymerase is included in the reaction, the amplicon may be then transcribed as a single-stranded RNA polymerase template to generate corresponding RNAs.

The nucleic acids produced by various embodiments of the present methods may be determined qualitatively or quantitatively by any of the existing techniques. For example, for a qualitative or quantitative assay, terminal-phosphate-labeled ribonucleotides may be used in combination with a phosphatase during/after nucleic acid amplification reaction for color generation. In such embodiments, the terminal phosphate may be protected from dephosphorylation by using terminal-phosphate methyl esters of dNTPs or deoxynucleoside tetraphosphates.

Any of the DNA polymerases known in the art may be employed for DNA amplification. DNA polymerases suitable for use in the inventive methods may demonstrate one or more of the following characteristics: strand displacement activity; the ability to initiate strand displacement from a nick; and/or low degradation activity for single stranded DNA. In some embodiments, the DNA polymerase employed may be devoid of one or more exonuclease activity. For example, the DNA polymerase may be a 3'→5' exonuclease-deficient DNA polymerase or the DNA polymerase may lack 5'→3' exonuclease activity. In some embodiments, the DNA polymerase may lack both 3'→5' and 5'→3' activity (i.e., an exo (−) DNA polymerase). Exemplary DNA polymerases useful for the methods include, without limitation, Phi29 DNA polymerase, Klenow, 5'→3' exonuclease-deficient Bst DNA polymerase (the Klenow fragment of Bst DNA polymerase I), 5'→3' exonuclease-deficient delta Tts DNA polymerase (the Klenow fragment of Tts DNA polymerase I), exo (−) Klenow, or exo(−) T7 DNA polymerase (T7 Sequenase).

Any of the art-recognized buffers for nucleic acid synthesis reactions (e.g., Tris buffer, HEPES buffer) that results in a reaction pH between 6 and 9 may be used. In some embodiments, the pH of the nucleic acid amplification reaction is 7.7. In general, buffers that enhance DNA stability (e.g., HEPES) may be preferred in certain amplicon production methods. However, thermo labile buffers such as Tris:Borate, HEPES, and MOPS buffers may be disfavored for some specific amplicon production methods employing thermal denaturation of a target DNA.

Polymerase enzymes typically require divalent cations (e.g., $Mg^{+2}$, $Mn^{+2}$, or combinations thereof) for nucleic acid synthesis. Accordingly, one or more divalent cations may be added to the reaction mixture. For example, $MgCl_2$ may be added to the reaction mixture at a concentration range of 2 mM to 6 mM. Higher concentrations of $MgCl_2$ may be preferred when high concentrations (e.g., greater than 10 pmoles, greater than 20 pmoles, or greater than 30 pmoles) of inosine-containing primer are included in the reaction mixture.

The reaction mixture for nucleic acid assay may further include one or more surfactants (e.g., detergents). Surfactants may be applied to the reaction tube before introducing the first component of the reaction mixture. Alternatively, surfactants may be added to the reaction mixture along with the reaction components. In some embodiments, the surfactant may be a detergent selected from Tween-20, NP-40, Triton-X-100, or combinations thereof. In some embodiments, 0.05% NP-40 and 0.005% Triton X-100 are added to the reaction mixture. In some specific embodiments, the reaction buffer may comprise 25 mM Tris:borate; 5 mM $MgCl_2$; 0.01% Tween; and 20% ethylene glycol.

One or more blocking agents such as an albumin (e.g., BSA or HSA) may be added to the reaction mixture to bind to the surface of the reaction vessel (e.g., plastic microcentrifuge tube or microtiter plate) thereby increasing the relative amount target DNA that is available for reaction with the nucleases or polymerases.

In some other embodiments reaction mixture may include at least one topoisomerase (e.g., a type 1 topoisomerase). In some embodiments, the topoisomerase may be present in the reaction mixture at a final concentration of at least 0.1 ng/μL.

In some embodiments, the reaction mixture may include at least one single stranded DNA binding protein (e.g., E. coli SSB, T4 gene 32 protein (T4 g32p), T7 gene 2.5 protein, Ncp7, recA, or combinations thereof). In some embodiments, at least one single stranded DNA binding protein may be present in the reaction mixture at a final concentration of at least 0.1 ng/μL.

The reaction mixture may include one or more reducing agents (e.g., dithiothreitol (DTT), 2-mercaptoethanol (βME), Tris(carboxyethyl) phosphine (TCEP), or 2-mercaptoethylamine (MEA)) that reduces the oxidation of enzymes in the reaction mix and improves the quality and yield of the amplicons produced.

In some embodiments, a wild type endonuclease V may be employed for nucleic acid assays that involves a nicking of an inosine-containing DNA as described in the inventive methods. Non-limiting examples of wild type enodonuleuse V includes endonuclease V from *Escherichia*, *Archaeoglobulus*, *Thermatoga*, *Salmonella*, *Yersinia* or human. For example, the wild type endonuclease V may be an E. coli endonuclease V (SEQ ID NO: 1), Afu endonuclease V (SEQ ID NO: 56) or a Tma endonuclease V (SEQ ID NO: 57). Aft endonuclease V may be preferred in assays wherein highest level of specificity for inosine-containing strand nicking since Afu endonuclease V is very specific for inosine and does not act on other abasic or hairpin type of structures.

Figure 11A:
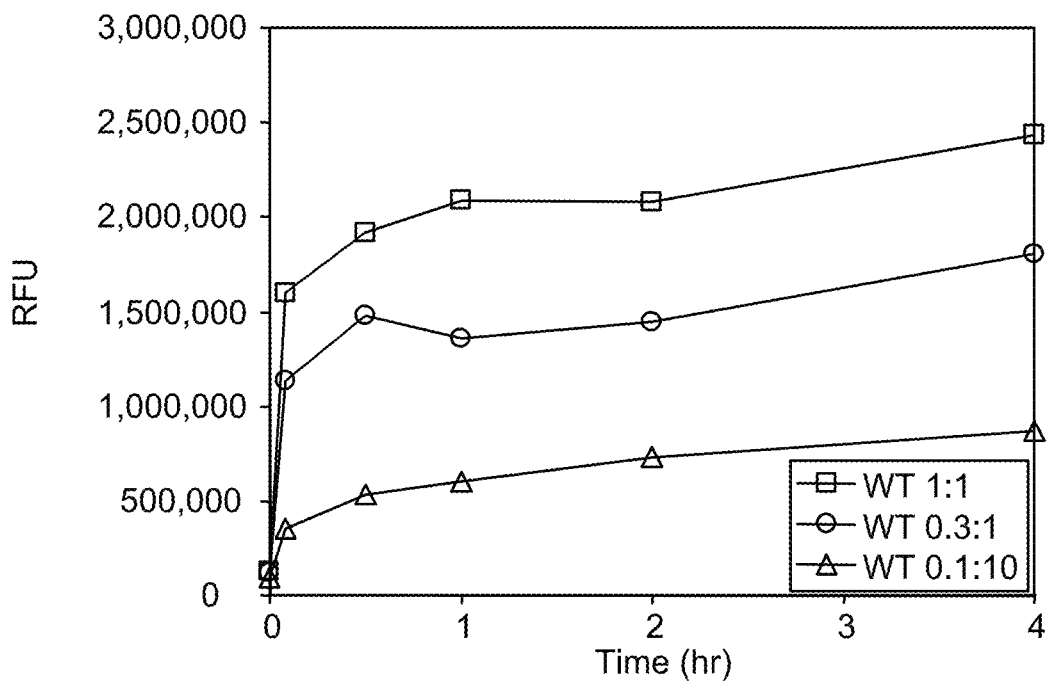
FIG. 11A and FIG. 11B depict the relative activities of the wild-type (WT) endonuclease V to the activity of the mutant endonuclease V as described in Example 12.
Figure 11B:
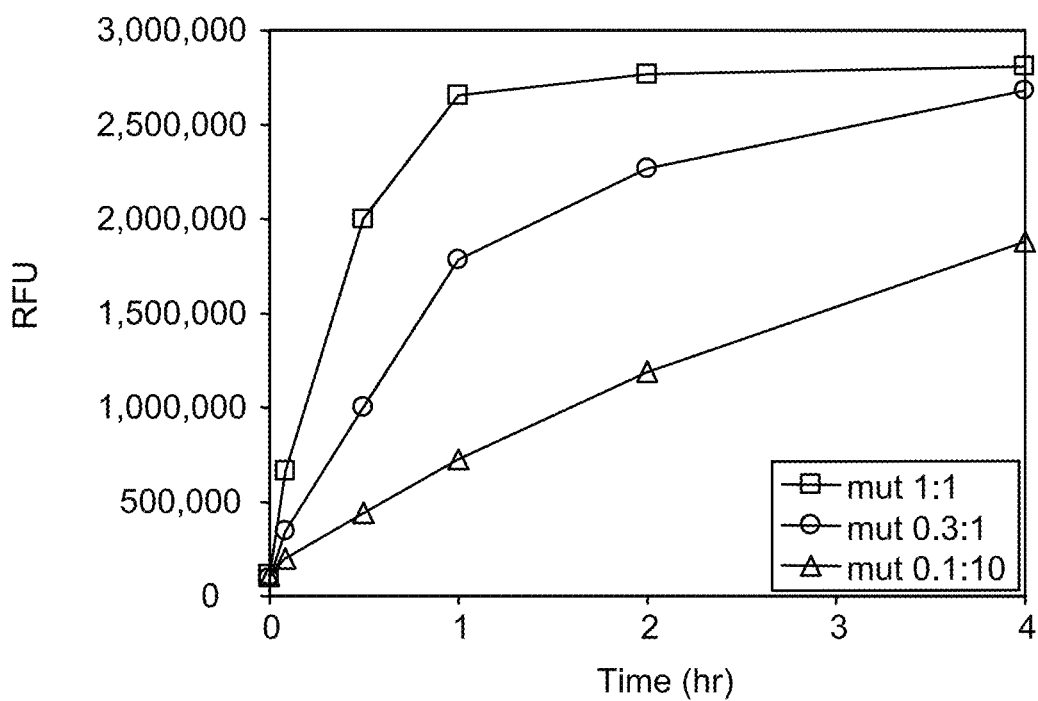

In some embodiments, a mutant endonuclease V is employed to nick the inosine-containing DNA. The mutant endonuclease V may be generated by any of the art-recognized techniques for genetic engineering/protein engineering of proteins including site-directed mutagenesis or artificial gene synthesis. The genetic engineering may include an alteration of one or more amino acid residues of a wild type endonuclease V. The alteration may include substitution, insertion and/or deletion of one or more amino acid residues of the wild type endonuclease V. Mutant endonuclease V may be generated by rational design of protein or by directed evolution. In some embodiments, a rationally designed, mutant endonuclease V enzyme is employed that has increased substrate binding, increased nicking efficiency, increased nicking specificity and/or increased nicking sensitivity. A mutant endonuclease V may also be designed such that the substrate binding is reversible. The mutant endonuclease V enzyme may then support repeated nicking by each enzyme, whereas the corresponding wild type enzyme is capable of only a single round (or a few limited rounds) of nicking (for example, the wild type E. coli endonuclease V remains bound to the DNA after nicking). Such mutant endonuclease V may be used in a reaction mixture in less than stoichiometric quantities to effect a nicking reaction. For example, FIG. 11B demonstrates a repeated nicking of a mutant E. coli endonuclease V enzyme leading to exponential nicking reaction kinetics with time.

In some embodiments, a mutant E. coli endonuclease V is provided. In some embodiments, the mutant E. coli endonuclease is a Y75A mutant E. coli endonuclease V corresponding to SEQ ID NO: 2. This mutant is generated by replacing the Tyrosine (Y) residue at the $75^{th}$ position of a wild type E. coli endonuclease V (SEQ ID NO: 1) with an Alanine (A) residue. In some embodiments, a mutant Afu endonuclease Y74A (SEQ ID NO:3) and/or its conservative variants is employed. The mutant Y74A Afu endonuclease is generated by substituting a Tyrosine (Y) residue at the $75^{th}$ position of a wild type Afu endonuclease V (SEQ ID NO: 56) with an alanine (A) residue.

In some embodiments, conservative variants of the mutant endonuclease V are provided. For example, further alteration of a mutant endonuclease V via substitution, deletion, and/or addition of a single amino acid or a small number (typically less than about ten) of amino acids may be a "conservative variant" if the physico-chemical properties of the altered mutant endonuclease V is similar to the original mutant endonuclease V. In some cases, the alteration may be a substitution of one amino acid with a chemically similar amino acid.

In some embodiments, a heat stable endonuclease V is preferred. For example, in a nucleic acid assay, where thermal denaturation (either partial or full denaturation) of a target DNA is performed, a heat stable endonuclease V or a heat stable endonuclease V mutant may be preferred. In other embodiments where thermal denaturation of a target DNA is not required, a wild type endonuclease V or an endonuclease V mutant (e.g., Y75A mutant *E. coli* endonuclease V) that has maximum enzymatic activity at a relatively low temperature (e.g., 45° C.) may be preferred. For example, Y75A *E. Coli* endonuclease V mutant is inactivated by incubation at 50° C., whereas it retains its enzymatic activity at 37-40° C. Afu endonuclease V (both wild type and Y75A mutant) or Tma endonuclease V (both wild type and Y80A mutant) are generally more thermo stable than the *E. coli* endonuclease V (both wild type and Y75A mutant). In some embodiments where strand displacement DNA synthesis by DNA polymerase may be increased by incubation at an elevated temperature, an endonuclease V which functions at high temperature (e.g., 45-80° C.) may be preferred.

In some embodiments, mutant endonuclease V preferentially nicks the inosine-containing strand of a double stranded DNA at a position 3' to the inosine residue when the inosine residue is paired with a cytosine residue. In some other embodiments, endonuclease V mutant preferentially nicks the inosine-containing strand of a double stranded DNA at a position 3' to the inosine residue when the inosine residue is paired with a thymine residue. The mutant endonuclease V may have a higher efficiency than the wild type endonuclease V to nick the inosine-containing strand of the double stranded DNA when the inosine is paired with cytosine or thymine. Further, a mutant endonuclease V may preferentially nick an inosine-containing strand of a double stranded DNA than an inosine-containing single stranded DNA. For example, Y75A *E. coli* mutant endonuclease V nicks a double stranded DNA comprising an inosine residue better than a single stranded DNA comprising an inosine residue. In contrast, Y80A Tma mutant endonuclease V nicks a single stranded DNA comprising an inosine residue better than a double stranded DNA comprising an inosine residue. Some mutant endonucleases may nick structures other than DNA sequences containing inosine residue while some others may be very specific to inosine-containing DNA sequences. For example, Tma and Aft endonucleases does not nick structures such as flaps and pseudo Y structures. In some embodiments, when there are multiple inosine residues in a double stranded DNA, the endonuclease V mutant may preferentially nick (often 1 or 2 nucleotides 3' to the inosine residue) the inosine residue that is paired with a cytosine residue than the inosine residue that is paired with a thymine residue. In some aspects, the endonuclease V mutant may nick a double stranded DNA containing base pair mismatches. The nicking may happen at the location of the base pair mismatch or at a location 3' to the base pair mismatch that is separated by one or more bases.

In some embodiments, an isolated nucleic acid sequence comprising a sequence that encodes the mutant endonuclease V is also provided. In some embodiments, the isolated nucleic acid comprises a nucleic acid sequence of SEQ ID NO: 59 or of a degenerate variant of SEQ ID NO: 59. The isolated nucleic acid sequence may comprise a sequence that encodes a polypeptide consisting of the amino acid sequence of SEQ ID NO: 2 (Y75A mutant *E. coli* endonuclease V). In some other embodiments, the isolated nucleic acid comprises a nucleic acid sequence of SEQ ID NO: 60 or of a degenerate variant of SEQ ID NO:60. The isolated nucleic acid sequence may comprise a sequence that encodes a polypeptide consisting of the amino acid sequence of SEQ ID NO: 3 (Y75A mutant Afu endonuclease V). The isolated nucleic acid sequence may further be incorporated into a suitable vector, may be delivered to a host cell (for example, via transfection, transduction or transformation) and may be expressed to generate the desired mutant endonuclease V. The expressed mutant endonuclease V may be isolated and purified from the host cell by employing any of the art-recognized techniques for protein isolation and purification.

In some embodiments, a nucleic assay that employs the mutant endonuclease V is provided. The nucleic acid assay may include any assay that involves selective nicking of a double stranded DNA by a mutant endonuclease V at a position 3' to an inosine residue, when the inosine residue is base-paired with a cytosine residue. In some embodiments, the assay includes the steps of (a) providing a double stranded DNA containing an inosine residue paired with a cytosine residue (b) nicking the double stranded DNA at a residue 3' to the inosine residue and (c) performing the nucleic acid assay. The double stranded DNA containing the inosine residue base-paired with a cytosine residue may be generated by hybridizing an appropriately designed inosine-containing primer to a target DNA template, wherein the target DNA template is a single stranded DNA sequence. In some embodiments, the double stranded DNA containing inosine residue paired with cytosine residue is generated in situ by a primer-mediated replication of a target DNA template. The nucleic acid assay may be a nucleic acid amplification reaction, a nucleic acid detection reaction or both. In some embodiments, a nucleic acid amplification is performed by extending the nicked strand (the strand containing the inosine residue) via a nucleic acid extension reaction using a DNA polymerase and dNTPs. The assay may be performed by using any mutant endonuclease V from any source that is capable of nicking an inosine-containing strand of a double stranded DNA wherein the inosine reside is base-paired with a cytosine residue. In some embodiments, the DNA polymerase employed may be devoid of one or more exonuclease activity. For example, the DNA polymerase may be a 3'→5' exonuclease-deficient DNA polymerase or the DNA polymerase may lack 5'→3' exonuclease activity (proofreading activity). In some embodiments, the DNA polymerase may lack both 3'→5' and 5'→3' activity (i.e., an exo (−) DNA polymerase). In some embodiments, a strand displacement DNA polymerase is used for the nucleic acid extension reaction. Exemplary DNA polymerases useful for the methods include, without limitation, Bst DNA polymerase, delta Tts DNA polymerase, Klenow, 5'→3' exonuclease-deficient Bst DNA polymerase, 5'→3' exonuclease-deficient delta Tts DNA polymerase, exo (−) Klenow, exo (−) Bst DNA polymerase or exo (−) delta Tts DNA polymerase. In some embodiments, the nucleic acid extension reaction is performed under isothermal conditions.

The nucleic acid amplification methods described herein may be used to amplify genomes or fragments of genome for subsequent SNP analysis. It could also be used to generate antisense probe from mRNA using an oligo (dT) primer containing an inosine residue near the end. Combined with Phi29 DNA polymerase the DNA amplification methods may be employed to amplify extremely large pieces of DNA. The methods may also be used for linear amplification of one strand or exponential amplification of both strands of a target DNA.

In some embodiments, the nucleic acid assay that employs the mutant endonuclease V comprises a single tube DNA amplification and sequencing. Single tube DNA amplification and sequencing may use a combination of plasmid amplification and cycle sequencing. For example, a DNA polymerase such as Phi29 DNA polymerase, random hexamers and dNTP's may be employed for amplification of a plasmid. A thermally stable sequencing DNA polymerase (which does not work well at 30° C.), 3' charged dye labeled terminators (which are not incorporated by phi29 DNA polymerase), and a sequencing primer which is thiophosphorylated at the 3' end to prevent degradation by the phi29 DNA polymerase may be included during the amplification reaction. After a short period at 30° C. to allow the plasmid to be amplified, the temperature of the reaction mixture may be raised and cycled from 95 to 60° C. The 3' charged terminators are important for allowing the use of dGTP in the sequencing reaction, as they prevent secondary structures during electrophoresis. In this reaction, the amplification components do not affect the sequencing reaction (the phi29 DNA polymearase is heat inactivated and the hexamers do not bind at temperatures over 45° C.) and the sequencing components do not affect the amplification reaction (the DNA polymerase is inactive at low temperatures and the terminators are not incorporated by the phi29 DNA polymerase). However, under such reaction conditions, the sequencing primer may get extended during the amplification reaction. To avoid such sequencing primer extension reaction, the mutant endonuclease V may be used in such single tube DNA amplification and sequencing reactions. For example, the sequencing primer may be designed to comprise an inosine residue located near to its 3' end (e.g., at about 3 nucleotides from its 3' end), and a thiophosphate bond on its 3' terminal base. Due to the thiophosphate bond on its 3' terminal end, the primer will not get degraded during the amplification reaction. Further, if the primer is getting extended during the amplification reaction, the mutant endonuclease V would nick the extended primer back to original size thus making it available for subsequent sequencing reaction. A thermo labile mutant endonuclease V may be selected for the reaction such that the endonuclease V gets inactivated during the first cycle along with the phi29 DNA polymerase. Once these enzymes are inactivated, subsequent sequencing reaction may be conducted in the same tube.

The mutant endonuclease V enzymes described herein may also be other nucleic acid assays. For example, they may be used to remove primers after PCR or other types of amplification that contains such primers. They may be employed to clip a DNA sequence that is attached to a surface by a segment of DNA containing an inosine residue. Further, they may be used to amplify one strand of a PCR product that contains an inosine residue in one of its primers. Other applications of such mutant endonuclease V enzymes include, but not limited to, to degrade DNA that was produced in a reaction containing d-inosine-triphosphate and to degrade PCR primers after a PCR reaction, in which the primers used for PCR contained inosine replacing the guanosine.

In some embodiments, a kit for nucleic assay comprising an endonuclease V is provided. The endonuclease V may be a wild type endonuclease or a mutant endonuclease V. In some other embodiments, a kit comprising a genetically engineered, mutant endonuclease V is provided. The mutant endonuclease V may be a protein the sequence of which consists of, SEQ ID NO: 2, SEQ ID NO: 3, or conservative variants thereof. In some embodiments, the mutant endonuclease may be a Y75A mutant E. coli endonuclease V, or a Y75A mutant Afu endonuclease V.

In some embodiments, an amplicon production kit is provided that comprises at least one inosine-containing primer, at least one DNA polymerase and at least one nuclease that is capable of nicking DNA at a residue 3' to an inosine residue. The DNA polymerase may be an exonuclease-deficient DNA polymerase. In some embodiments, the DNA polymerase may be an exonuclease-deficient DNA polymerase with strand displacement activity. In some embodiments, the nuclease that is capable of nicking DNA at a residue 3' to an inosine residue may be an endonuclease V. In some embodiments, the kit comprises a mutant endonuclease V, the sequence of which consists of, SEQ ID NO: 2, SEQ ID NO: 3, or conservative variants thereof. The mutant endonuclease may be a Y75A mutant E. coli endonuclease V, or a Y75A mutant Aft endonuclease V.

The amplicon production kit may further comprise a chemical denaturant (e.g., glycerol, ethylene glycol, or formamide) and may further include a surfactant (e.g., Tween-20, NP-40, Triton-X-100, or a combination thereof). The amplicon production kit may further include one or more divalent cations (e.g., $Mn^{2+}$, $Mg^{2+}$, or a combination thereof), which may be present in the buffer at a final concentration of 2 mM to 6 mM. The amplicon production kit may further comprise a reducing agent (e.g., DTT, βME, MEA, or TCEP) and/or at least one single stranded DNA binding protein (e.g., E. coli SSB, T4 gene 32 protein, T7 gene 2.5 protein, Ncp7, recA, or combinations thereof). In some embodiments, the amplicon production kit may further comprise at least one at least one blocking agent comprising albumin and/or at least one topoisomerase.

Practice of the invention will be still more fully understood from the following examples, which are presented herein for illustration only and should not be construed as limiting the scope of the present invention as defined by the appended claims. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min,": minutes and "h.": hours.

Commercially available stock buffers used in Examples are shown in Tables 1-3 below. ThermoFidelase was obtained from Fidelity Systems, Gaithersburg, Md.; T7, DEPC water, and NaCl were obtained from Ambion; dNTPs were obtained from GE Healthcare; Tris-HCl and Tween 20 were obtained from Sigma Aldrich. Volumes shown in the following Tables are in microliters unless otherwise indicated

TABLE 1

10X Sequenase Buffer

| Reagent | Volume | Concentration |
| --- | --- | --- |
| 1M Tris-HCl, pH 7.6 | 800 µL | 400 mM |
| 1M $MgCl_2$ | 400 µL | 200 mM |
| 5M NaCl | 200 µL | 500 mM |
| 100 mM dATP | 50 µL | 2.5 mM |
| 100 mM dCTP | 50 µL | 2.5 mM |
| 100 mM dGTP | 50 µL | 2.5 mM |
| 100 mM dTTP | 50 µL | 2.5 mM |
| Tween 20 | 2 µL | 0.1% |
| 1M DTT | 20 µL | 10 mM |
| DEPC Water | 378 µL | |
| Total Vol. | 2000 µL | |

TABLE 2

10X Klenow Buffer

| Reagent | Volume | Concentration |
| --- | --- | --- |
| 1M Tris-HCl, pH 7.6 | 1000 µL | 0.5M |
| 1M $MgCl_2$ | 200 µL | 0.1M |
| 100 mM dATP | 50 µL | 2.5 mM |
| 100 mM dCTP | 50 µL | 2.5 mM |
| 100 mM dGTP | 50 µL | 2.5 mM |
| 100 mM dTTP | 50 µL | 2.5 mM |

TABLE 2-continued

| 10X Klenow Buffer | | |
|---|---|---|
| Reagent | Volume | Concentration |
| Tween 20 | 2 μL | 0.1% |
| 1M DTT | 20 μL | 10 mM |
| DEPC Water | 578 μL | |
| Total Volume | 2000 μL | |

TABLE 3

| 10X Endonuclease V Buffer |
|---|
| 100 mM Tris-Borate pH 8 |
| 0.1% Tween 20 |
| 30 mM MgCl$_2$ |
| 2.5 mM each dNTP |
| 10 mM DTT |

Table 4 provides the sequences of wild type endonucleases, mutant endonuclease V enzymes, template DNAs, and various primers that are used in the examples. *Bacillus cereus* strain ATCC 15816 DNA gyrase subunit A gene used as a template is identified as DNAG5 in the following examples.

TABLE 4

Sequences of wild type endonucleases, mutnat endonucleases, template DNAs, and various primers

| | Ref. No. | Sequence (N-term-C-term; 5'→3') | Length |
|---|---|---|---|
| WT *E. coli* endonuclease V | SEQ ID NO: 1 | MIMDLASLRAQQIELASSVIREDRLDKD PPDLIAGADVGFEQGGEVTRAAMVLLK YPSLELVEYKVARIATTMPYIPGFLSFRE YPALLAAWEMLSQKPDLVFVDGHGISH PRRLGVASHFGLLVDVPTIGVAKKRLCG KFEPLSSEPGALAPLMDKGEQLAWVWR SKARCNPLFIATGHRVSVDSALAWVQR CMKGYRLPEPTRWADAVASERPAFVRY TANQP | 223 |
| Y75A mutant *E. coli* endonuclease V | SEQ ID NO: 2 | MIMDLASLRAQQIELASSVIREDRLDKD PPDLIAGADVGFEQGGEVTRAAMVLLK YPSLELVEYKVARIATTMPAIPGFLSFRE YPALLAAWEMLSQKPDLVFVDGHGISH PRRLGVASHFGLLVDVPTIGVAKKRLCG KFEPLSSEPGALAPLMDKGEQLAWVWR SKARCNPLFIATGHRVSVDSALAWVQR CMKGYRLPEPTRWADAVASERPAFVRY TANQPLE | 225 |
| Y74A mutant Afu endonuclease V | SEQ ID NO: 3 | MLQMNLEELRRIQEEMSRSVVLEDLIPL EELEYVVGVDQAFISDEVVSCAVKLTFP ELEVVDKAVRVEKVTFPAIPTFLMFREG EPAVNAVKGLVDDRAAIMVDGSGIAHP RRCGLATYIALKLRKPTVGITKKRLFGE MVEVEDGLWRLLDGSETIGYALKSCRR CKPIFISPGSYISPDSALELTRKCLKGYKL PEPIRIADKLTKEVKRELTPTSKLK | 221 |
| Ban 1 Template | SEQ ID NO: 4 | CAATTGTAATTTCTGTACGTCTCTTATC ATTGAAGCGCTCTTTTACTTCTGTTAAT TCTTCACGAATAATCTCAAGA | 77 |
| P-1 | SEQ ID NO: 5 | TCTTGAGATTATTCIT | 15 |
| P2-1 | SEQ ID NO: 6 | CAATTGTAATTTCTIT | 15 |
| P3 | SEQ ID NO: 7 | AAATTAATACGACTCACTATAGGGTGA AGAATTAACAGAAGTAAAAGAGCddC | 51 |
| P-3 Mismatched | SEQ ID NO: 8 | AAATTAATACGACTCACTATAGGGTTG AAGAATTAACAGAAGTAAAAGAGA | 51 |
| P-3 NO ddC | SEQ ID NO: 9 | AAATTAATACGACTCACTATAGGGTGA AGAATTAACAGAAG | 41 |
| P-3SD Mod | SEQ ID NO: 10 | AAATTAATACGACTCACTATAGGGTTG AAGAATTAACAGAAGTAAAAGAGddC | 51 |
| Primer 1354 | SEQ ID NO: 11 | TCGCTGAATTAAAAIC | 16 |
| Primer 1333 | SEQ ID NO: 12 | ATCAAGATTTAATGAAIT | 18 |

TABLE 4-continued

Sequences of wild type endonucleases, mutnat endonucleases, template DNAs, and various primers

| | Ref. No. | Sequence (N-term-C-term; 5'→3') | Length |
|---|---|---|---|
| Primer 1498 | SEQ ID NO: 13 | TGTTCTGGAATCAAIT | 16 |
| Primer 1517 | SEQ ID NO: 14 | AACGTAATGGCGATIT | 16 |
| Primer 1275 | SEQ ID NO: 15 | TTAGATATGCGTCTIC | 16 |
| Primer 1294 | SEQ ID NO: 16 | GCTTAACAGGATTAIA | 16 |
| Primer 1313 | SEQ ID NO: 17 | CGAAAAAATTGAACAAIA | 18 |
| Primer 1378 | SEQ ID NO: 18 | CAGATGAAGAAAAGIT | 16 |
| Primer 1482 | SEQ ID NO: 19 | CTTCATCTTCAATAIA | 16 |
| Primer 1534 | SEQ ID NO: 20 | AATATAACCATTATGAIT | 18 |
| Primer 1560 | SEQ ID NO: 21 | TACGTAGAAGCTGIC | 15 |
| Primer 1579 | SEQ ID NO: 22 | ACCACGGTTCTGTIT | 15 |
| cP-3 3' Quencher | SEQ ID NO.: 23 | CCCTATAGTGAGTCGTATTAATTT-IowaBlack | 24 |
| Fluorescent Primer 1 | SEQ ID NO: 24 | FAM-GGTCGACTIAGGAGGATCCCCGGGTAC | 27 |
| Fluorescent Primer 2 | SEQ ID NO: 25 | HEX-CCGGGGATCCTCCTCAGTCGACCTGCA | 27 |
| endoV us | SEQ ID NO: 26 | GAGATATACATATGGATCTCGCG | 23 |
| endoV int ds | SEQ ID NO: 27 | GAATCGCCGGCATGGTGGTGGCGATGCG | 28 |
| endoV int us | SEQ ID NO: 28 | ACCATGCCGGCGATTCCAGGTTTTCTTTCCTTC | 33 |
| endoV ds | SEQ ID NO: 29 | TGGTGCTCGAGGGGCTGATTTGATG | 25 |
| DNA-G-Long-3' | SEQ ID NO: 30 | GATATTCATCAATCGGAGTACGTTTTC | 27 |
| DNA-G-5' | SEQ ID NO: 31 | ACAATCAACAACAAGCACGAATTCGAG | 27 |
| 7290R | SEQ ID NO: 32 | AGTTCTTCTTTCGTCCCCIT | 20 |
| 7270R | SEQ ID NO: 33 | CAGGCTGACATCACIIT | 17 |
| 7253R | SEQ ID NO.: 34 | TCAGTTGTTCACCCAGCIA | 19 |
| 7234R | SEQ ID NO: 35 | GCGGAGACGGGCAATCAIT | 19 |
| 7215R | SEQ ID NO: 36 | TCATCTTTCGTCATIIA | 17 |
| 7194R | SEQ ID NO.: 37 | TCCACAGAGAAACAATIIC | 19 |

TABLE 4-continued

Sequences of wild type endonucleases, mutnat endonucleases, template DNAs, and various primers

| | Ref. No. | Sequence (N-term-C-term; 5'→3') | Length |
|---|---|---|---|
| 7062F | SEQ ID NO: 38 | ACCACCGGCGATCCIIC | 17 |
| 7079F | SEQ ID NO: 39 | GCGTGAGTTCACCATIA | 17 |
| 7096F | SEQ ID NO: 40 | TTCAGTCAGCACCGCTIA | 18 |
| 7111F | SEQ ID NO: 41 | TGATGCTGCTGGCTIA | 16 |
| 7127F | SEQ ID NO: 42 | CCCTGATGAGTTCGTIT | 17 |
| 7144F | SEQ ID NO: 43 | CCGTACAACTGGCIT | 15 |
| T7-7158F-misA: | SEQ ID NO: 44 | ATGACTGGTGGACAGCAAATGGGTAA ATTAATACGACTCACTATAGGGTT | 50 |
| Quencher-oligo | SEQ ID NO: 45 | CCCTATAGTGAGTCGTATTAATTT-3iaBrqsP | 24 |
| Dye-oligo | SEQ ID NO: 46 | ACCCAT/i6-TAMN/TTGCTGTCCACCAGTTAC | |
| F. primer 40FGI | SEQ ID NO: 47 | GTTTTCCCAGTCACGACGTTGTAAAACGACGICC | 34 |
| R. primer 40RGI | SEQ ID NO: 48 | TCAAAGAAGTATTGCTACAACGG | 23 |
| F. primer: 40FGG | SEQ ID NO: 49 | GTTTTCCCAGTCACGACGTTGTAAAACGACGGCC | 34 |
| R. primer 40RGG | SEQ ID NO: 50 | TCAAAGAAGTATTGCTACAACGG | 23 |
| Tban-1 forward primer: | SEQ ID NO: 51 | GCAGATGAAGAAAAGGTTCTTGAGAT TATTCIT | 33 |
| Dye-P-3 | SEQ ID NO: 52 | 5'-TAMRA Dye-AAATTAATACGACTCACTATAGGGTTG AAGAATTAACAGAAGTAAAAGAGddC-3' | 51 |
| Wild Type Afu endonuclease V | SEQ ID NO: 56 | MLQMNLEELRRIQEEMSRSVVLEDLIPL EELEYVVGVDQAFISDEVVSCAVKLTFP ELEVVDKAVRVEKVTFPYIPTFLMFREG EPAVNAVKGLVDDRAAIMVDGSGIAHP RRCGLATYIALKLRKPTVGITKKRLFGE MVEVEDGLWRLLDGSETIGYALKSCRR CKPIFISPGSYISPDSALELTRKCLKGYKL PEPIRIADKLTKEVKRELTPTSKLK | 221 |
| Wild Type Tma endonuclease V | SEQ ID NO: 57 | Y80Y | 225 |
| Y80A mutant Tma endonuclease V | SEQ ID NO: 58 | MDYRQLHRWDLPPEEAIKVQNELRKKI KLTPYEGEPEYVAGVDLSFPGKEEGLAV IVVLEYPSFKILEVVSERGEITFPAIPGLL AFREGPLFLKAWEKLRTKPDVVVFDGQ GLAHPRKLGIASHMGLFIEIPTIGVAKSR LYGTFKMPEDKRCSWSYLYDGEEIIGCV IRTKEGSAPIFVSPGHLMDVESSKRLIKA FTLPGRRIPEPTRLAHIYTQRLKKGLF | 225 |
| Y75A mutant E.coli endonuclease V | SEQ ID NO: 59 | GTGATTATGGATCTCGCGTCATTACGC GCTCAACAAATCGAACTGGCTTCTTCT GTGATCCGCGAGGATCGACTCGATAA AGATCCACCGGATCTGATCGCCGGAGC CGATGTCGGGTTTGAGCAGGGCGGAG AAGTGACGCGAGCGGCGATGGTGCTG | 678 |

TABLE 4-continued

Sequences of wild type endonucleases, mutnat endonucleases, template DNAs, and various primers

| | Ref. No. | Sequence (N-term-C-term; 5'→3') | Length |
|---|---|---|---|
| | | CTGAAATATCCCTCGCTTGAGCTGGTC<br>GAGTATAAAGTTGCCCGCATCGCCACC<br>ACCATGCCTTACATTCCAGGTTTTCTTT<br>CCTTCCGCGAATATCCTGCGCTGCTGG<br>CAGCGTGGGAGATGNNNTCGCAAAAG<br>CCGGATTTAGTGTTTGTCGATGGTCAT<br>GGGATCTCGCATCCTCGCCGTCTTGGC<br>GTCGCCAGCCATTTTGGCTTATTGGTG<br>GATGTGCCGACCATTGGCGTGGCGAA<br>AAAACGGCTCTGCGGTAAATTCGAACC<br>GCTCTCCAGCGAACCGGGCGCGCTGGC<br>CCCACTGATGGATAAAGGCGAGCAGC<br>TGGCCTGGGTCTGGCGCAGCAAAGCG<br>CGCTGTAACCCGTTGTTTATCGCTACC<br>GGCCATCGGGTCAGCGTGGACAGCGC<br>GCTGGCGTGGGTACAACGCTGCATGA<br>AAAGGCTATCGTCTGCCGGAGCCAACGC<br>GCTGGGCGGACGCGGTGGCCTCGGAA<br>CGTCCGGCGTTCGTGCGCTATACAGCA<br>AATCAGCCCTAA | |
| Y74A mutant<br>Afu<br>endonuclease V | SEQ ID<br>NO: 60 | GTGCTTCAAATGAATCTCGAAGAGCTG<br>AGGAGGATACAGGAGGAGATGTCCAG<br>AAGTGTGGTTCTCGAAGACTTAATCCC<br>TCTTGAAGAGCTTGAGTACGTTGTGGG<br>TGTTGATCAGGCCTTTATCAGCGATGA<br>GGTTGTCTCATGTGCGGTCAAGCTGAC<br>CTTTCCGGAACTGGAGGTTGTTGATAA<br>AGCTGTGAGGGTTGAGAAGGTCACTTT<br>CCCCNNNATCCCCACCTTTCTCATGTT<br>CAGGGAGGGAGAGCCTGCAGTTAATG<br>CGGTCAAAGGGCTTGTGGATGACAGA<br>GCGGCAATCATGGTTGATGGGAGCGG<br>AATTGCCCATCCGAGAAGGTGCGGGCT<br>TGCAACATACATCGCCCTAAAGCTGAG<br>AAAGCCGACTGTGGGGATAACAAAGA<br>AAAGGCTTTTTGGTGAGATGGTAGAGG<br>TGGAAGATGGGCTTTGGAGGCTTTTAG<br>ATGGAAGTGAAACCATAGGCTACGCC<br>CTTAAAAGCTGCAGGAGGTGCAAACC<br>AATCTTCATCTCACCGGGGAGTTACAT<br>ATCTCCTGACTCAGCCTTGGAGCTGAC<br>GAGAAAGTGCCTTAAAGGCTACAAGC<br>TTCCTGAGCCGATAAGAATCGCCGACA<br>AACTTACCAAGGAGGTTAAGAGGGAG<br>TTGACTCCAACCTCAAAGCTTAAATAA | 666 |

Amplicons may be visualized and/or quantified using any of art-recognized techniques (e.g., electrophoresis to separate species in a sample and observe using an intercalating dye such as ethidium bromide, acridine orange, or proflavine). Amplicon production may also be tracked using optical methods (e.g., ABI Series 7500 Real-Time PCR machine) and an intercalating dye (e.g., SYBR Green I). The amplicons produced in the following examples were visualized using electrophoresis or optical techniques.

Example 1

Preparation of a PCR Product from the *B. cereus* Genomic DNA that is Used as Template for Amplification Reactions (Hereinafter, this PCR Product is Referred as "DNAG5")

*Bacillus cereus* (*B. Cereus*) strain 15816 from American Type Culture Collection (ATCC, Manassas, Va.) was grown according to the supplier's recommendations. A lyophilized culture of *B. cereus* was re-suspended in 400 μL of Nutrient Broth then transferred to 5.6 mL of Nutrient Broth and incubated overnight at 30° C. with shaking. The Genomic DNA (gDNA) was isolated from the overnight liquid culture using MasterPure™ Gram Positive DNA Purification Kit (Epicentre® Biotechnologies, #GP1-60303) according to the manufacturer's instructions.

4×1.0 mL of overnight culture was pelleted by centrifugation in separate 1.5 mL tubes. Each pellet was resuspended in 100 μL TE Buffer by vortexing vigorously and added to separate 0.65 ml tubes. The 1.5 mL tubes were rinsed with 50 μL each TE Buffer and the wash were combined with the appropriate 100 μL of resuspended pellet. 1 μL of Ready-Lyse Lysozyme was added to each resuspended pellet, mixed, and incubated at 37° C. for 60 minutes. 150 μL Gram Positive Lysis Solution & 1 μL Proteinase K was added to each tube and mixed. Samples were incubated at 70° C. for 15 minutes, vortexing every 5 minutes. The samples were then cooled to 37° C. for 5 minutes and then placed on ice for 5 minutes. 175 μL MPC Protein Precipitation Reagent was added to each tube. The debris was pelleted at high speed in a microfuge for 10 minutes. Supernatant was transferred to a clean 1.5 mL tube and the pellet was discarded. 1 μL RNase A (5 μg/μL) was added to each tube and incubated 30 minutes at 37° C. 500 μL 2-propanol was added to each tube and inverted 35 times to mix. The tubes were centrifuged 10 minutes at high speed in a microfuge to pellet the DNA. Each pellet was rinsed with 70% ethanol, dried, and resuspended in 35 μL TE buffer. 1 μL from each preparation was run on a 1% agarose gel.

Figure 4:
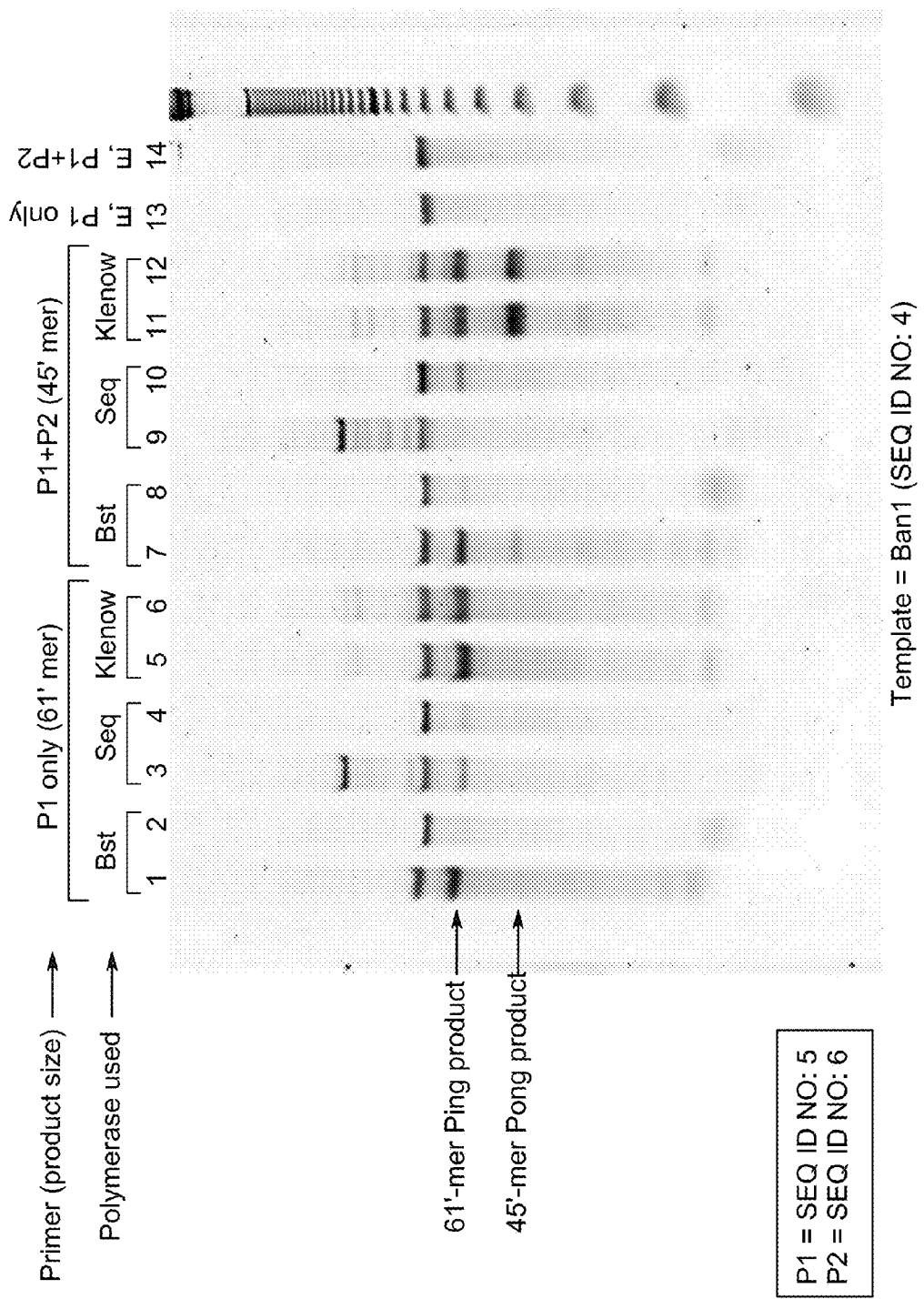
FIG. 4 depicts the use of a variety of polymerases to produce amplicons from a target DNA ("Ban 1"), in which a single primer (expected product of 61 nucleotides) or multiple primers (forward and reverse, with expected products of 61 nucleotides (61'-mer) and 45 nucleotides (45'-mer)) were employed as described in the Example 2.

(Invitrogen), 7M-urea gel. The results are shown in FIG. 4, wherein the 61'-mer and 45'-mer depicts the expected products. The "Ping product" was generated in almost all reactions. A small amount of both "Ping product" and the "Pong product" was generated by Bst polymerase, whereas a large amount of both "Ping product" and the "Pong product" was generated by exo (−) Klenow. Columns 13 and 14 in Table 5 represent the polymerase extension of only primers.

TABLE 5

| Reagent/ID | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 10X Endonuclease V Buffer | 1 | | 1 | | 1 | | 1 | | 1 | | 1 | | 1 | 1 |
| 10X TP Buffer | | 1 | | | | | | 1 | | | | | 0.5 | 0.5 |
| 10X T7 Buffer | | | | 1 | | | | | | 1 | | | 0.5 | 0.5 |
| 10X Klenow Buffer | | | | | | 1 | | | | | | 1 | | 0.5 |
| Ban 1 Template | 0.5 | 0.5 | 0.5 | 0.5 | 0.5 | 0.5 | 0.5 | 0.5 | 0.5 | 0.5 | 0.5 | 0.5 | 0.5 | 0.5 |
| P-1 | 0.5 | 0.5 | 0.5 | 0.5 | 0.5 | 0.5 | 0.5 | 0.5 | 0.5 | 0.5 | 0.5 | 0.5 | 2 | 2 |
| P2-1 | | | | | | | 0.5 | 0.5 | 0.5 | 0.5 | 0.5 | 0.5 | | |
| T4 g32p | 0.5 | 0.5 | 0.5 | 0.5 | 0.5 | 0.5 | 0.5 | 0.5 | 0.5 | 0.5 | 0.5 | | | |
| Ethylene Glycol | 2 | 2 | 2 | 2 | 2 | 2 | 2 | 2 | 2 | 2 | 2 | 2 | | |
| Bst | 0.5 | 0.5 | | | | | 0.5 | 0.5 | | | | | 0.5 | 0.5 |
| T7 | | | 0.5 | 0.5 | | | | | 0.5 | 0.5 | | | 5 | 5 |
| Klenow | | | | | 0.5 | 0.5 | | | | | 0.5 | 0.5 | 10 | 10 |
| Endonuclease V | 0.5 | 0.5 | 0.5 | 0.5 | 0.5 | 0.5 | 0.5 | 0.5 | 0.5 | 0.5 | 0.5 | 0.5 | | |
| Water | 4.5 | 4.5 | 4.5 | 4.5 | 4.5 | 4.5 | 4 | 4 | 4 | 4 | 4 | 4 | | |
| Total Volume | 10 | 10 | 10 | 10 | 10 | 10 | 10 | 10 | 10 | 10 | 10 | 10 | | |

Approximately 100 ng of *B. cereus* gDNA was amplified in four separate reactions using PuReTaq Ready-To-Go PCR Beads (GE Healthcare) and 5 μM of each primer, DNA-G-Long-3' (SEQ ID NO:30) and DNA-G-5' (SEQ ID NO:31). Thermal cycling conditions were: (1) 95° C. for 5 minutes; (2) 95° C. for 30 seconds; (3) 50° C. for 30 seconds; (4) 72° C. for 1 minute. Steps 2-4 were repeated 31 times and the products were held at +4° C.

One-tenth of each completed reaction was analyzed by electrophoresis using a 1% agarose gel. A 2181 base pair product was generated and used as the target DNA. Following analysis, the four amplification reactions were pooled and diluted in TE Buffer±0.01% Tween 20 prior to use.

Example 2

DNA Amplification Employing Various Polymerases, Single Primer and Two Primers

Exo (−) T7 DNA polymerase (Sequenase), exo(−) Bst polymerase (Bst large fragment) and exo (−) Klenow fragment were compared according to the reaction scheme presented below in Table 5 (volumes are indicated in microliters). P-1 corresponds to SEQ ID NO: 5 and P2-1 corresponds to SEQ ID NO: 6. Reactions 1, 2, 7, and 8 containing the exo (−) Bst polymerase were incubated at 43° C. for 3 hours. The remaining reactions containing exo (−) Klenow or T7 Sequenase were incubated at 37° C. for 3 hours. Following storage at −20° C., the reactions were run on a 15% acrylamide Example 3

Multiple Sets of Primers and Single Strand Binding Protein 4, 6, and 12 mixes of primers were combined as shown below in Tables 6-13. The primer mixes were prepared so that one addition would add 10 pmol [final concentration] of each oligos to the reaction mixture.

12 Mix:

TABLE 6

| Oligo |
|---|
| P-1 |
| P2-1 |
| 1275 |
| 1294 |
| 1313 |
| 1333 |
| 1378 |
| 1482 |
| 1517 |
| 1534 |
| 1560 |
| 1579 |

6 Mix:

TABLE 7

| Oligo |
| --- |
| P-1 |
| P2-1 |
| 1333 |
| 1378 |
| 1482 |
| 1517 |

4 Mix:

TABLE 8

| Oligo |
| --- |
| P-1 |
| P2-1 |
| 1378 |
| 1482 |

Internal 4 Mix: The term "internal" represents that these primers were internal to the other primers used in other reactions:

TABLE 9

| Oligo |
| --- |
| 1354 (645 pmol/uL) |
| 1333 (681 pmol/uL) |
| 1498 (732 pmol/uL) |
| 1517 (671 pmol/uL) |

Reaction Scheme: DNAG5 was diluted 1:100 in TE buffer. 10× HEMT buffer includes 100 mM HEPES (pH 8), 1 mM EDTA, 0.1% Tween 20, and 30 mM MgCl$_2$.

TABLE 10

| Component | \multicolumn{12}{c}{ID} |
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| DNAG5 1:100 | − | − | − | − | − | − | − | + | + | + | + | + |
| 12 mix | + | − | − | − | − | − | − | + | − | − | − | − |
| 6 mix | − | + | − | − | − | − | − | − | + | − | − | − |
| 4 mix | − | − | + | − | − | + | + | − | − | + | − | − |
| Internal 4 Mix | − | − | − | + | + | + | + | − | − | − | + | + |
| SSB, 1 μg/uL | + | − | − | + | − | + | − | + | − | − | + | − |
| SSB, 10 ng/uL | − | + | + | − | + | − | + | − | + | + | − | + |
| 1354 (10 pmol/uL) | − | − | − | − | − | − | − | − | − | − | − | − |
| 1333 (10 pmol/uL) | − | − | − | − | − | − | − | − | − | − | − | − |
| 1498 (10 pmol/uL) | − | − | − | − | − | − | − | − | − | − | − | − |
| 1517 (10 pmol/uL) | − | − | − | − | − | − | − | − | − | − | − | − |

TABLE 10-continued

| Component | \multicolumn{12}{c}{ID} |
| --- | --- | --- | --- | --- | --- | --- | --- | --- | --- | --- | --- | --- |
|  | 13 | 14 | 15 | 16 | 17 | 18 | 19 | 20 | 21 | 22 | 23 | 24 |
| DNAG5 1:100 | + | + | + | + | + | + | − | − | − | − | − | − |
| B. cereus gDNA (100 ng/uL) | − | − | − | − | − | − | + | + | + | + | + | + |
| 12 mix | − | − | − | − | − | − | + | − | − | − | − | − |
| 6 mix | + | + | − | − | − | − | − | + | − | − | − | − |
| 4 mix | − | − | + | + | − | − | − | − | + | − | + | + |
| Internal 4 Mix | − | − | − | − | + | + | − | − | − | + | + | + |
| SSB, 1 μg/uL | + | + | − | − | + | + | − | − | − | − | − | + |
| SSB, 10 ng/uL | − | + | + | + | − | − | + | + | + | + | + | − |
| 1354 (10 pmol/uL) | + | − | + | − | − | − | − | − | − | − | − | − |
| 1333 (10 pmol/uL) | + | − | − | + | − | − | − | − | − | − | − | − |
| 1498 (10 pmol/uL) | − | + | + | − | − | − | − | − | − | − | − | − |
| 1517 (10 pmol/uL) | − | + | − | − | − | − | − | − | − | − | − | − |

Bulk Denaturation Mixes: Volumes shown in Tables are in microliters unless otherwise indicated.

TABLE 11

| Component/ID | A (X5) | B (X5) | C (X15) | D (X13) |
| --- | --- | --- | --- | --- |
| 10X HEMT Buffer | 5 | 5 | 15 | 13 |
| 12 mix | 2.5 | — | — | — |
| 6 mix | — | 2.5 | — | — |
| 4 mix | — | — | 7.5 | — |
| Internal 4 Mix | — | — | — | 6.5 |
| Water | 10 | 10 | 7.5 | 7.5 |
| Total Volume | 17.5 | 17.5 | 30 | 26 |

3.5 μL of 'A' were added to each of 1, 8, and 19; 3.5 μL, of 'B' were added to each of 2, 9, and 20; 2.0 μL, of 'C' were added to each of 3, 6, 7, 10, 13, 14, 15, 16, 17, 18, 21, 23, and 24; and 2.0 μL, of 'D' were added to each of 4, 5, 6, 7, 11, 12, 17, 18, 22, 23, and 24.

Denaturations:

TABLE 12

| Component | \multicolumn{12}{c}{ID} |
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| DNAG5 1:100 | — | — | — | — | — | — | — | 1 | 1 | 1 | 1 | 1 |
| Bulk Denaturation Mix A | 3.5 | — | — | — | — | — | — | 3.5 | — | — | — | — |
| Bulk Denaturation Mix B | — | 3.5 | — | — | — | — | — | — | 3.5 | — | — | — |
| Bulk Denaturation Mix C | — | — | 2 | — | — | 2 | 2 | — | — | 2 | — | — |
| Bulk Denaturation Mix D | — | — | — | 2 | 2 | 2 | 2 | — | — | — | 2 | 2 |
| 1354 (10 pmol/uL) | — | — | — | — | — | — | — | — | — | — | — | — |
| 1333 (10 pmol/uL) | — | — | — | — | — | — | — | — | — | — | — | — |
| 1498 (10 pmol/uL) | — | — | — | — | — | — | — | — | — | — | — | — |
| 1517 (10 pmol/uL) | — | — | — | — | — | — | — | — | — | — | — | — |
| Water | 1.5 | 1.5 | 3 | 3 | 3 | 1 | 1 | 0.5 | 0.5 | 2 | 2 | 2 |
| Total Vol. | 5 | 5 | 5 | 5 | 5 | 5 | 5 | 5 | 5 | 5 | 5 | 5 |

TABLE 12-continued

| Component | ID | | | | | | | | | | | |
|---|---|---|---|---|---|---|---|---|---|---|---|---|
| | 13 | 14 | 15 | 16 | 17 | 18 | 19 | 20 | 21 | 22 | 23 | 24 |
| DNAG5 1:100 | 1 | 1 | 1 | 1 | 1 | 1 | — | — | — | — | — | — |
| B. cereus gDNA (100 ng/uL) | — | — | — | — | — | — | 1 | 1 | 1 | 1 | 1 | 1 |
| Bulk Denaturation Mix A | — | — | — | — | — | — | 3.5 | — | — | — | — | — |
| Bulk Denaturation Mix B | 2 | 2 | — | — | — | — | — | 3.5 | — | — | — | — |
| Bulk Denaturation Mix C | — | — | 2 | 2 | 2 | 2 | — | — | 2 | — | 2 | 2 |
| Bulk Denaturation Mix D | — | 1 | — | — | 2 | 2 | — | — | — | 2 | 2 | 2 |
| 1354 (10 pmol/uL) | 1 | — | 1 | — | — | — | — | — | — | — | — | — |
| 1333 (10 pmol/uL) | 1 | — | — | 1 | — | — | — | — | — | — | — | — |
| 1498 (10 pmol/uL) | — | 1 | 1 | — | — | — | — | — | — | — | — | — |
| 1517 (10 pmol/uL) | — | — | — | 1 | — | — | — | — | — | — | — | — |
| Water | 5 | 5 | — | — | — | — | 0.5 | 0.5 | 2 | 2 | — | — |
| Total Vol. | 5 | 5 | 5 | 5 | 5 | 5 | 5 | 5 | 5 | 5 | 5 | 5 |

Bulk Enzyme Mixes: 10 Rxn Buffer used in Table 13 includes 100 mM HEPES, 30 mM MgCl$_2$, 0.1% Tween 20, 2.5 mM each dNTP, and 10 mM TCEP.

TABLE 13

| Component/ID | 1X | Y(X10) | Z(X18) |
|---|---|---|---|
| 10X Reaction Buffer) | 1 | 10 | 18 |
| 100% Ethylene Glycol | 1 | 10 | 18 |
| E coli SSB, 1 µg/uL | 1 | 10 | — |
| E coli SSB, 10 ng/uL | — | — | 18 |
| ΔTts (20 U/) | 1 | 10 | 18 |
| Endonuclease V (40 pmol/) | 0.075 | 0.75 | 1.35 |
| Water | 0.925 | 9.25 | 16.65 |
| Total Volume | 5 | 50 | 90 |

5 µL, of component "X" were added to each of reaction mixes 1, 4, 6, 8, 11, 17, 18, and 24; 5 µL, of "Z" were added to each of 2, 3, 5, 7, 9, 10, 12, 13, 15, 16, 19, 20, 21, 22, and 23. All reaction mixtures were incubated at 45° C. for 75 minutes and a 1/10th aliquot was analyzed on a 10% TB Urea gel, in which each of the oligo mixtures generated product of the expected sizes. None of the reactions performed on genomic DNA yielded expected products. One of the 4-primer mixes did not work when the 1 microgram of SSB was added, but did give the expected products when 1 ng of SSB was added on the PCR product template (DNAG5).

Example 4

Isothermal Amplification Using Internal 6 Oligo Mix (Amplicon Production Using Multiple Sets of Nested Primers)

Selected oligos were removed from the 6 oligo mix to determine which oligo or oligos caused the doublet band between 70 and 80 bases. Also, variations of divalent cation and single strand binding protein concentrations were tested. None of the tested variations altered the doublet band, and one remaining possibility is that it may be caused by incomplete denaturation during electrophoresis.

Oligo Mixes:

TABLE 14

| Oligo | A OM | B OM |
|---|---|---|
| P-1 (972 pmol/uL) | 1.03 µL | — |
| P2-1 (335 pmol/uL) | 2.99 µL | 2.99 µL |
| 1333 (681 pmol/uL) | 1.47 µL | 1.47 µL |
| 1378 (645 pmol/uL) | 1.55 µL | 1.55 µL |
| 1482 (661 pmol/uL) | — | 1.51 µL |
| 1517 (671 pmol/uL) | 1.49 µL | 1.49 µL |
| TE + 0.01% Tween 20 | 41.47 µL | 40.99 µL |
| Total Volume | 50 µL | 50 µL |

Reaction Scheme: Rxn Buffer A (10× reaction buffer) used in Table 15 includes 100 mM HEPES, 30 mM MgCl$_2$, 0.1% Tween 20, 2.5 mM each dNTP, and 10 mM TCEP. 10 Rxn Buffer B used in Table 15 includes 100 mM HEPES, 60 mM MgCl$_2$, 0.1% Tween 20, 2.5 mM each dNTP, and 10 mM TCEP.

TABLE 15

| Component | ID | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| DNAG5 1:10 | − | − | − | − | + | + | + | + | − | − | − | − | + | + |
| DNAG5 1:100 | − | − | − | − | − | − | − | − | + | + | + | + | − | − |
| 12 Mix | + | − | − | − | + | − | − | − | + | + | − | − | + | + |
| 6 Mix | − | + | − | − | − | + | − | − | − | − | + | + | − | − |
| A OM | − | − | + | − | − | − | + | − | − | − | − | − | − | − |
| B OM | − | − | − | + | − | − | − | + | − | − | − | − | − | − |
| Rxn Buffer A (3 mM) | − | − | − | − | − | − | − | − | − | − | + | + | − | − |
| Rxn Buffer B (6 mM) | + | + | + | + | + | + | + | + | + | + | − | − | + | + |
| 30 mM Mg | − | − | − | − | − | − | − | − | − | − | − | − | + | − |

TABLE 15-continued

| Component | 15 | 16 | 17 | 18 | 19 | 20 | 21 | 22 | 23* | 24* | 25* | 26* | 27* | 28* |
|---|---|---|---|---|---|---|---|---|---|---|---|---|---|---|
| 60 mM Mg | − | − | − | − | − | − | − | − | − | − | − | − | − | + |
| 90 mM Mg | − | − | − | − | − | − | − | − | − | − | − | − | − | − |
| SSB, 1 ng/Rxn | − | − | − | − | − | − | − | + | − | + | − | − | − | − |
| SSB, 1 µg/Rxn | + | + | + | + | + | + | + | + | − | + | − | + | + | + |

| Component | 15 | 16 | 17 | 18 | 19 | 20 | 21 | 22 | 23* | 24* | 25* | 26* | 27* | 28* |
|---|---|---|---|---|---|---|---|---|---|---|---|---|---|---|
| DNAG5 1:10 | + | + | + | + | − | − | − | − | − | − | − | − | − | − |
| DNAG5 1:100 | − | − | − | − | − | − | − | − | − | − | − | − | − | − |
| B. cereus gDNA 100 ng/Rxn | + | − | − | − | + | + | + | + | − | − | − | − | − | − |
| 12 Mix | − | − | − | − | + | − | − | + | + | + | − | − | − | − |
| 6 Mix | − | + | + | + | − | + | − | − | − | − | − | + | + | + |
| A OM | − | − | − | − | − | − | + | − | − | − | − | − | − | − |
| B OM | − | − | − | − | − | − | − | + | − | − | − | − | − | − |
| Rxn Buffer A (3 mM) | + | − | − | − | − | − | − | − | − | − | − | − | − | − |
| Rxn Buffer B (6 mM) | − | + | + | + | + | + | + | + | + | + | + | + | + | + |
| 30 mM Mg | − | + | − | − | − | − | − | + | − | + | − | + | − | − |
| 60 mM Mg | + | − | + | − | − | − | − | − | + | − | + | − | + | − |
| 90 mM Mg | − | − | − | + | − | − | − | − | − | − | + | − | − | + |
| SSB, 1 ng/rxn | + | − | − | − | − | − | − | − | − | − | − | − | − | − |
| SSB, 1 µg/uL | − | + | + | + | + | + | + | + | + | + | + | + | + | + |

*Extra MgCl₂ added to the reaction mixture to understand if increased Mg²⁺ improves the reaction.

No Template Control Denaturations: 10×HE Buffer includes 100 mM HEPES (pH*) and 1 mM EDTA.

TABLE 16

| Component/ID | 1 | 2 | 3 | 4 | 23 |
|---|---|---|---|---|---|
| 10x HE Buffer | 1 µL | 1 µL | 1 µL | 1 µL | 1 µL |
| DNAG5 1:10 | — | — | — | — | — |
| DNAG5 1:100 | — | — | — | — | — |
| 12 Mix | 0.5 µL | — | — | — | 0.5 µL |
| 6 Mix | — | 0.5 µL | — | — | — |
| A OM | — | — | 0.5 µL | — | — |
| B OM | — | — | — | 0.5 µL | — |
| 30 mM MgCl₂ | — | — | — | — | 1 µL |
| 60 mM MgCl₂ | — | — | — | — | — |
| 90 mM MgCl₂ | — | — | — | — | — |
| Water | 2.5 µL | 2.5 µL | 2.5 µL | 2.5 µL | 1.5 µL |
| Total Volume | 4 µL | 4 µL | 4 µL | 4 µL | 4 µL |

| Component/ID | 24 | 25 | 26 | 27 | 28 |
|---|---|---|---|---|---|
| 10X HE Buffer | 1 µL | 1 µL | 1 µL | 1 µL | 1 µL |
| DNAG5 1:10 | — | — | — | — | — |
| DNAG5 1:100 | — | — | — | — | — |
| 12 Mix | 0.5 µL | 0.5 µL | — | — | — |
| 6 Mix | — | — | 0.5 µL | 0.5 µL | 0.5 µL |
| A OM | — | — | — | — | — |
| B OM | — | — | — | — | — |
| 30 mM MgCl₂ | — | — | 1 µL | — | — |
| 60 mM MgCl₂ | 1 µL | — | — | 1 µL | — |

Bulk Denaturation Mixes:

TABLE 17

| Component/ID | A (X6) | B (X6) | C (X3) | D (X3) |
|---|---|---|---|---|
| 10X HE Buffer | 6 µL | 6 µL | 3 µL | 3 µL |
| DNAG5 1:10 | 6 µL | 6 µL | — | — |
| DNAG5 1:100 | — | — | 3 µL | 3 µL |
| 12 Mix | 3 µL | — | 1.5 µL | — |
| 3 Mix | — | 3 µL | — | 1.5 µL |
| OM A | — | — | — | — |
| OM B | — | — | — | — |
| Water | 9 µL | 9 µL | 4.5 µL | 4.5 µL |
| Total Volume | 24 µL | 24 µL | 12 µL | 12 µL |

4 µL "A" in each of 5, 13, 14, and 15
4 µL "B" in each of 6, 16, 17, and 18
4 µL "C" in each of 9 and 10
4 µL "D" in each of 11 and 12

Denaturations:

TABLE 18

| Component | 7 | 8 | 19 | 20 | 21 | 22 |
|---|---|---|---|---|---|---|
| 10X HE Buffer | 1 µL | 1 µL | 1 µL | 1 µL | 1 µL | 1 µL |
| DNAG5 1:10 | 1 µL | 1 µL | — | — | — | — |
| DNAG5 1:100 | — | — | — | — | — | — |
| B. cereus gDNA 100 ng/uL | — | — | 1 µL | 1 µL | 1 µL | 1 µL |
| 12 Mix | — | — | 0.5 µL | — | — | — |
| 3 Mix | — | — | — | 0.5 µL | — | — |
| OM A | 0.5 µL | — | — | — | 0.5 µL | — |
| OM B | — | 0.5 µL | — | — | — | 0.5 µL |
| 30 mM MgCl₂ | — | — | — | — | — | — |

TABLE 18-continued

| Component | 7 | 8 | 19 | 20 | 21 | 22 |
|---|---|---|---|---|---|---|
| 60 mM MgCl$_2$ | — | — | — | — | — | — |
| 90 mM MgCl$_2$ | — | — | — | — | — | — |
| Water | 1.5 μL | 1.5 μL | 1.5 μL | 1.5 μL | 1.5 μL | 1.5 μL |
| Total Volume | 4 μL | 4 μL | 4 μL | 4 μL | 4 μL | 4 μL |

Bulk Enzyme Mixes:

TABLE 19

| Component/ID | V (X2) | W (X2) | X (X2) | Y (X8) | Z (X21) |
|---|---|---|---|---|---|
| 10X Rxn Buffer A (3 mM) | 2 μL | 2 μL | — | — | — |
| 10X Rxn Buffer B (6 mM) | — | — | 2 μL | 8 μL | 21 μL |
| 100% Ethylene Glycol | 2 μL | 2 μL | 2 μL | 8 μL | 21 μL |
| E. coli SSB (1 ng/uL) | 2 μL | — | 2 μL | — | — |
| E. coli SSB (1 μg/uL) | — | 2 μL | — | 8 μL | 21 μL |
| ΔTts (20 U/uL) | 2 μL | 2 μL | 2 μL | 8 μL | 21 μL |
| Endo V (40 pmol/uL) | 0.15 μL | 0.15 μL | 0.15 μL | 0.6 μL | 1.58 μL |
| Water | 3.85 μL | 3.85 μL | 3.85 μL | 7.4 μL | 85.58 μL |
| Total Volume | 12 μL | 12 μL | 12 μL | 40 μL | 126 μL |

6 μL "V" in 11
6 μL "W" in 12
6 μL "X" in 9
5 μL "Y" in 13-18 (Additional amount of MgCl$_2$ added in 1 μL volume, see Table 16)
6 μL "Z" in each of 1-8, 10, and 19-28

All reactions were incubated at 45° C. for 75 minutes and applied to a gel. FIG. 5 demonstrates that Ping-Pong reaction generated the expected products, however, no oligo eliminations removed the unwanted 74 nucleotide product.

Example 5

In Vitro Transcription (IVT)

Bulk Standard Isothermal Amplification Reaction: Template Primer Mix includes 0.08 pmol of SEQ ID NO: 4; 2 pmol of SEQ ID NO: 5; 10 pmol of SEQ ID NO: 6; and 18 pmol of SEQ ID NO: 7.

TABLE 20

| Component | 1X | 3X |
|---|---|---|
| 10X Endonuclease V Buffer | 1 | 3 |
| Template Primer Mix | 0.5 | 1.5 |
| Klenow (10 U/μL) | 0.5 | 1.5 |
| Endonuclease V (8 pmol/μL) | 0.5 | 1.5 |
| ThermoFidelase | 1 | 3 |
| TAP/T4 g32p (0.005 U TAP; 0.2 μg T4g32P) | 0.5 | 1.5 |
| Water | 6 | 18 |
| Total Vol. | 10 | 30 |

3 μL of the 3x bulk reaction were added to 6 μL GLB (gel loading buffer, Ambion) II (Before isothermal amplification). The remaining 3x bulk reaction was incubated at 45° C. for 75 minutes. The reaction was stopped by adding 2.7 μL, 110 mM EDTA. A 1-μL aliquot from the reaction was added to 2 GLB II (After isothermal amplification). Beta-Mercaptoethanol (β-ME) was obtained from Sigma (cat. #104K0161). 1M Tris-HCl, pH 8 was obtained from Ambion (cat. #105R055626A). The rNTP mixtures are shown in Table 21 below and the general reaction mixture for in vitro transcription is shown below in Table 22. For this example, components of MEGAscript T7 Kit (Ambion) were used.

TABLE 21

| Component | Amt |
|---|---|
| 75 mM ATP | 15 μL |
| 75 mM CTP | 15 μL |
| 75 mM GTP | 15 μL |
| 75 mM UTP | 15 μL |
| Total Volume | 60 μL |

TABLE 22

| Component | Amt |
|---|---|
| Water | 3 μL |
| rNTP Mix | 4 μL |
| 10X Buffer | 1 μL |
| Template | 1 μL |
| T7 Enzyme Mix | 1 μL |
| Total Volume | 10 μL |

(1.) 10×IVT Buffer—Tris/MgCl$_2$/DTT

TABLE 23

| Component | 1X |
|---|---|
| Water | 300 μL |
| 1M Tris—HCl, pH 8 | 400 μL |
| 1M DTT | 100 μL |
| 1M MgCl$_2$ | 200 μL |
| Total Volume | 1 ml |

Recipes of salt and magnesium solutions:

TABLE 24

| 185 mM MgCl$_2$ |
|---|
| 10 μL 1M MgCl$_2$ |
| 44 μL Water |
| Total Volume 54 |

TABLE 25

| | |
|---|---|
| 150 mM NaCl | |
| 3 µL 5M NaCl | |
| 97 µL Water | |
| Total Volume | 100 µL |

(2) 10×IVT Buffer—Tris/MgCl$_2$/β-mercaptoethanol

TABLE 26

| Component | 1X |
|---|---|
| Water | 299 µL |
| 1M Tris—HCl, Ph 8 | 400 µL |
| 99% β-ME | 101 µL |
| 1M MgCl$_2$ | 200 µL |
| Total Volume | 1 ml |

(3) 10×IVT Buffer—HEPES/MgCl$_2$/DTT

TABLE 27

| Component | 1X |
|---|---|
| Water | 300 µL |
| 1M HEPES, pH 8 | 400 µL |

TABLE 27-continued

| Component | 1X |
|---|---|
| 1M DTT | 100 µL |
| 1M MgCl$_2$ | 200 µL |
| Total Volume | 1 ml |

(4) 10×IVT Buffer—HEPES/MgCl$_2$/β-ME

TABLE 28

| Component | 1X |
|---|---|
| Water | 299 µL |
| 1M HEPES, pH 8 | 400 µL |
| 99% β-ME | 101 µL |
| 1M MgCl$_2$ | 200 µL |
| Total Volume | 1 ml |

Reaction Scheme: All reactions used 1 µL of the Bulk Standard IA Reaction described previously in table 20 in which the 10× Endonuclease V buffer was 100 mM HEPES, pH=8, 15 mM MgCl$_2$, 0.1% tween-20, 2.5 mM dNTP, 10 mM DTT. This contained additional. MgCl$_2$ addition of 18.5 mM (20 mM [final]) and NaCl addition of 15 mM ([final]). The reaction mixtures used are shown in Table 29.

TABLE 29

| | ID | | | | | | |
|---|---|---|---|---|---|---|---|
| Component | 1 | 2 | 3 | 4 | 5 | 6 | 7 |
| Water | 3 | 1 | 3 | 2 | 3 | 2 | 3 |
| rNTP Mix | 4 | 4 | 4 | 4 | 4 | 4 | 4 |
| 10X IVT Buffer (Ambion) | 1 | 1 | — | — | — | — | — |
| 10X Rxn Buffer A (described above) | — | — | 1 | 1 | — | — | — |
| 10X Rxn Buffer B (described above) | — | — | — | — | 1 | 1 | — |
| 185 mM MgCl$_2$ | — | — | — | 1 | — | 1 | — |
| Glycerol | — | 2 | — | — | — | — | — |
| #1 10× IVT Buffer - Tris/MgCl$_2$/DTT | — | — | — | — | — | — | 1 |
| #2 10× IVT Buffer - Tris/MgCl$_2$/β-ME | — | — | — | — | — | — | — |
| Template | 1 | 1 | 1 | 1 | 1 | 1 | 1 |
| T7 Enzyme Mix (Ambion) | 1 | 1 | 1 | 1 | 1 | 1 | 1 |
| Total Volume | 10 | 10 | 10 | 10 | 10 | 10 | 10 |

| | ID | | | | | | |
|---|---|---|---|---|---|---|---|
| Component | 8 | 9 | 10 | 11 | 12 | 13 | 14 |
| Water | 3 | 3 | 3 | 2 | 2 | 2 | 2 |
| rNTP Mix | 4 | 4 | 4 | 4 | 4 | 4 | 4 |
| 150 mM NaCl | — | — | — | 1 | 1 | 1 | 1 |
| #1 10X IVT Buffer - Tris/MgCl$_2$/DTT | — | — | — | 1 | — | — | — |
| #2 10X IVT Buffer -Tris/MgCl$_2$/β-ME | — | — | — | — | 1 | — | — |
| #3 10X IVT Buffer - HEPES/MgCl$_2$/DTT | — | 1 | — | — | — | 1 | — |
| #4 10X IVT Buffer - HEPES/MgCl$_2$/β-ME | — | — | 1 | — | — | — | 1 |
| Template | — | 1 | 1 | 1 | 1 | 1 | 1 |
| T7 Enzyme Mix | 1 | 1 | 1 | 1 | 1 | 1 | 1 |
| Total Volume | 1 | 10 | 10 | 10 | 10 | 10 | 10 |

Figure 6B:
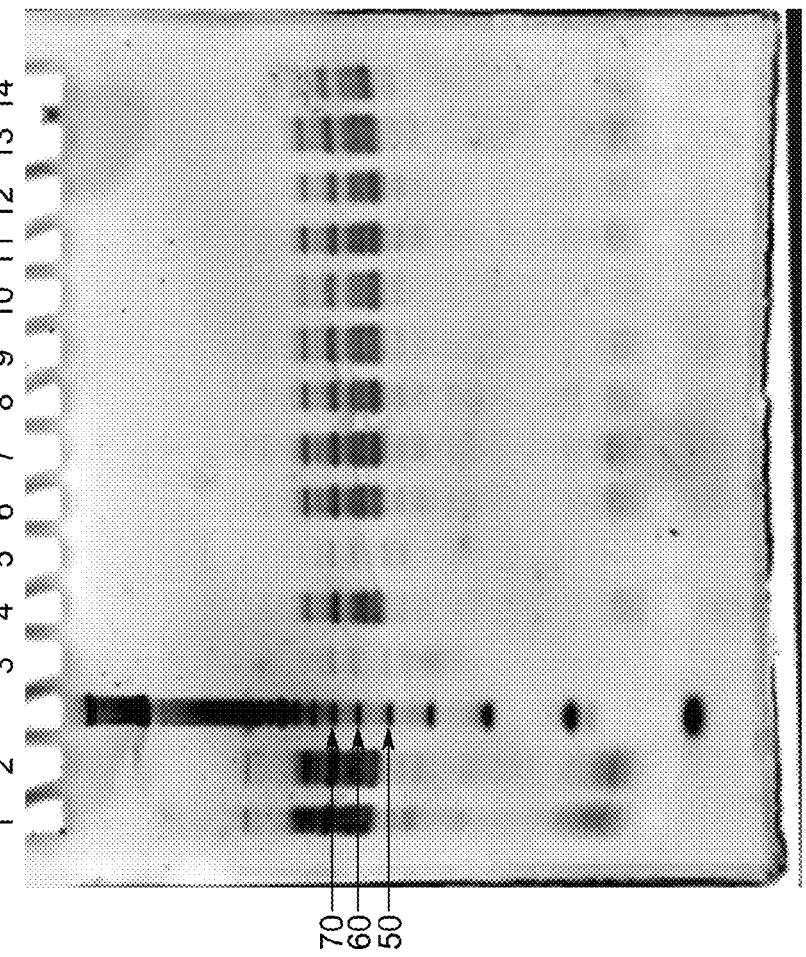
FIG. 6A and FIG. 6B depict in vitro transcription, variations in divalent cations, and variations in single strand binding proteins described in Example 5.
Figure 6A:
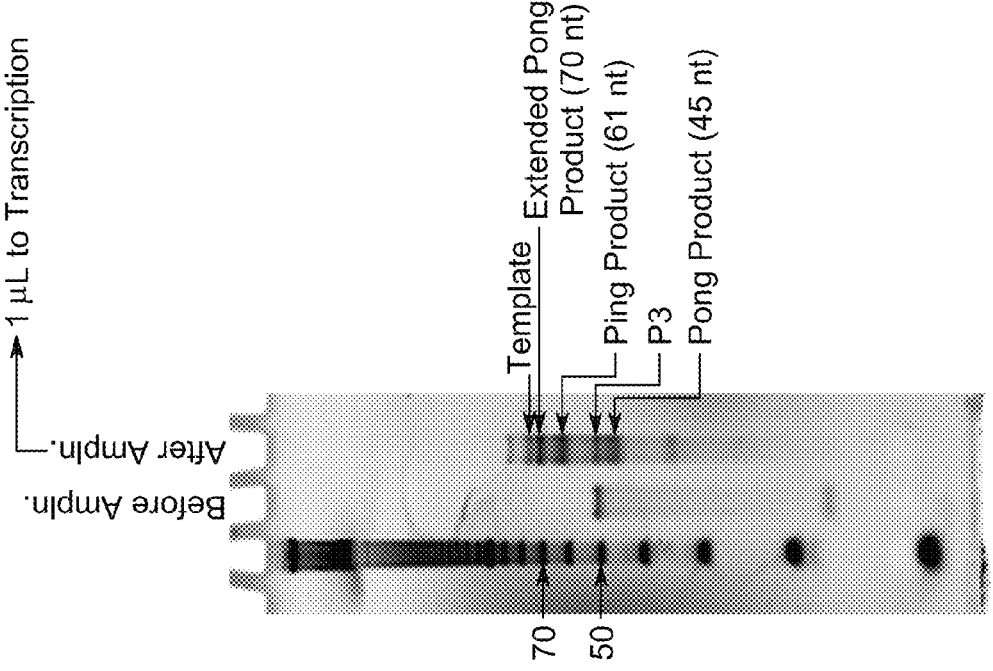

Each reaction, 1-14, was incubated at 37° C. for 2 hours and stopped by the addition of 20 µL GLB II. 3 µL/reaction were loaded into a well of a 15% acrylamide 7M-urea TBE gel (Invitrogen). FIG. 6A shows that ping-pong amplification product is generated. The pong product then binds to primer P3 (the extender primer) and is extended with a promoter sequence. FIG. 6B shows that the amplification product (ping-pong amplification product) is transcribed and corresponding RNA product (49 nucleotide product) is made.

Example 6

Effect of SSB on DNA Amplification: Mixed Oligos; Mg Concentration; and SSB Concentration The following experiment demonstrates that the addition of more than 1 ng of single strand binding protein to a 10 µL volume, increases fidelity and reduces background amplification significantly.

TABLE 30

| Component | ID | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| DNAG5 1:10 | − | − | − | − | − | − | − | − | + | + | + | + | + | + |
| DNAG5 1:100 | − | − | − | − | − | − | − | − | − | − | − | − | − | − |
| 3 mM MgCl2 | + | + | − | − | + | + | − | − | + | + | − | − | + | + |
| 6 mM MgCl2 | − | − | + | + | − | − | + | + | − | − | + | + | − | − |
| 12 Mix | + | + | + | + | − | − | − | − | + | + | + | + | − | − |
| 3 Mix | − | − | − | − | + | + | + | + | − | − | − | − | + | + |
| SSB 1 ng/reaction | + | − | + | − | + | − | + | − | + | − | + | − | + | − |
| SSB 1 µg/reaction | − | + | − | + | − | + | − | + | − | + | − | + | − | + |

| Component | ID | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| DNAG5 1:10 | + | + | − | − | − | − | − | − | − | − | + | + | + | + |
| DNAG5 1:100 | − | − | + | + | + | + | + | + | + | + | − | − | − | − |
| 3 mM MgCl2 | − | − | + | + | − | − | + | + | − | − | − | − | + | + |
| 6 mM MgCl2 | + | + | − | − | + | + | − | − | + | + | + | + | − | − |
| 12 Mix | − | − | + | + | + | + | − | − | − | − | − | − | + | + |
| 6 Mix | + | + | − | − | − | − | + | + | + | + | + | + | − | − |
| SSB 1 ng/reaction | + | − | + | − | + | − | + | − | + | − | − | + | − | + |
| SSB 1 µg/reaction | − | + | − | + | − | + | − | + | − | + | − | − | − | − |

Bulk Denaturation Mixes:

TABLE 31

| Component | A (X6) | B (X6) | C (X6) | D (X6) | E (X8) | F (X8) |
|---|---|---|---|---|---|---|
| 10X HE Buffer | 6 | 6 | 6 | 6 | 8 | 8 |
| DNAG5 1:10 | — | — | 6 | 6 | — | — |
| DNAG5 1:100 | — | — | — | — | 8 | 8 |
| 12 Mix | 3 | — | 3 | — | 4 | — |
| 3 Mix | — | 3 | — | 3 | — | 4 |
| Water | 15 | 15 | 9 | 9 | 12 | 12 |
| Total Volume | 24 | 24 | 24 | 24 | 32 | 32 |

4 µL, "A" were added to each of reactions 1-4; 4 µL, of "B" were added to each of reactions 5-8; 4 µL, of "C" were added to each of reactions 9-12; 4 µL, of "D" were added to each of reactions 13-16; 4 µL, "E" were added to each of reactions 17-20, 25, 26; and 4 µL, of "F" were added to each of reactions 21-24, 27, and 28.

Bulk Enzyme Mixes:

TABLE 32

| Component /ID | W (X9) | X (X9) | Y (X9) | Z (X9) |
|---|---|---|---|---|
| 10X Reaction Buffer, 3 mM Mg$^{+2}$ | 9 | 9 | — | — |
| 10X Reaction Buffer, 6 mM Mg$^{+2}$ | — | — | 9 | 9 |

TABLE 32-continued

| Component /ID | W (X9) | X (X9) | Y (X9) | Z (X9) |
|---|---|---|---|---|
| 100% Ethylene Glycol | 9 | 9 | 9 | 9 |
| E coli SSB, 1 ng/uL | 9 | — | 9 | — |
| E coli SSB, 1 µg/µL | — | 9 | — | 9 |
| ΔTts (20 U/µl) | 9 | 9 | 9 | 9 |
| Endonuclease V (40 pmol/µL) | 0.63 | 0.63 | 0.63 | 0.63 |
| Water | 17.37 | 17.37 | 17.37 | 17.37 |
| Total Vol. | 54 | 54 | 54 | 54 |

6 µL, of "W" were added to each of reactions 1, 5, 9, 13, 17, 21, and 25; 6 µL, of "X" were added to each of reactions 2, 6, 10, 14, 18, 22, and 26; 6 µL, of "Y" were added to each of reactions 3, 7, 11, 15, 19, 23, 27; and 6 µL, of "Z" were added to each of reactions 4, 8, 12, 16, 20, 24, and 28.

Figure 7:
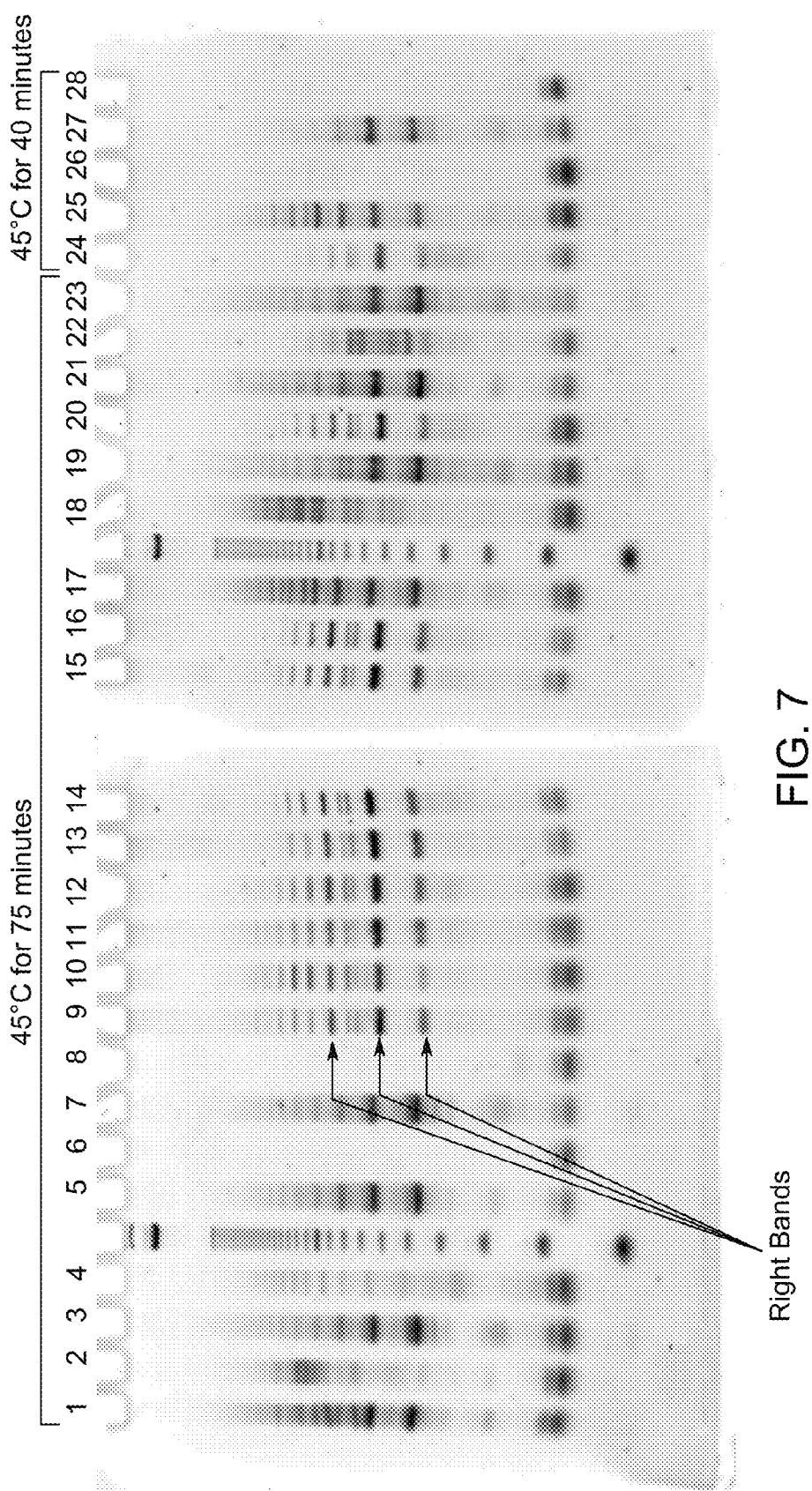
FIG. 7 shows the reaction products using a variety of SSB concentrations as described in Example 6.

Reactions 1-24 were incubated at 45° C. for 75 minutes and reactions 25-28 were incubated 45° C. for 40 minutes. A ¹⁄₁₀th aliquot of each reaction was analyzed on a 10% TB Urea gel (Invitrogen), which is shown in FIG. 7. In this example, the amount of template DNA, the number of primers, the divalent cation, and the amount of added SSB was varied to determine if there was any effect on reaction sensitivity and off-target primer amplification products. The addition of 1 microgram of SSB reduced the artifactual primer amplification products in the absence of added DNA template (lanes 2, 4, 6 and 8). The use of 12 primers, 6 mM MgCl$_2$, and 1 microgram of SSB resulted in the most sensitive detection of template DNA (lane 20), which was a product pattern than the 6-primer, 6 mM MgCl$_2$, and 1 microgram of SSB (lane 24).

Example 7

Amplicon Extension Using Extension Templates: Extender Templates; dd Terminators and Mismatched Primers

TABLE 33

12 Mix
Dye-P-3, 4133-92

TABLE 33-continued cP-3 3' Quencher SEQ ID NO.: 23
P-3 Mismatched SEQ ID NO.: 8
P-3SD Mod (ddC) SEQ ID NO.: 10
P-3 NO ddC SEQ ID NO.: 9
All oligos were diluted in TE + 0.01% Tween 20 to 10 pmol/uL Reaction Scheme:

TABLE 34

| Component | ID | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| DNAG5 1:10 | − | + | + | − | − | − | − | + | + | + | + | + | + | + |
| DNAG5 1:100 | − | − | − | + | + | − | − | − | − | − | − | − | − | − |
| DNAG5 1:1000 | − | − | − | − | − | + | + | − | − | − | − | − | − | − |
| 12 Mix | + | + | + | + | + | + | + | + | + | + | + | + | − | − |
| 12 Mix less SEQ ID NO.: 17 | − | − | − | − | − | − | − | − | − | − | − | − | + | + |
| P-3 SD Mod | − | − | − | − | − | − | − | + | − | − | − | − | − | − |
| P-3 NO ddC | − | − | − | − | − | − | − | − | + | − | − | − | − | − |
| P-3 Mismatched | − | − | − | − | − | − | − | − | − | + | − | − | − | − |
| cP-3 3' Quencher | − | − | − | − | − | − | − | − | − | − | + | − | − | − |
| Dye-P-3 | − | − | − | − | − | − | − | − | − | − | − | + | − | − |
| ROX-11-ddG (3 pmol/) | − | − | + | − | + | − | + | − | − | − | − | − | − | + |

Denaturations:

TABLE 35

| Component | ID | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| 10X HE Buffer | 1 | 1 | 1 | 1 | 1 | 1 | 1 | 1 | 1 | 1 | 1 | 1 | 1 | 1 |
| DNAG1:10 | — | 1 | 1 | — | — | — | — | 1 | 1 | 1 | 1 | 1 | 1 | 1 |
| DNAG1:100 | — | — | — | 1 | 1 | — | — | — | — | — | — | — | — | — |
| DNAG1:1000 | — | — | — | — | — | 1 | 1 | — | — | — | — | — | — | — |
| 12 Mix | 0.5 | 0.5 | 0.5 | 0.5 | 0.5 | 0.5 | 0.5 | 0.5 | 0.5 | 0.5 | 0.5 | 0.5 | — | — |
| 12 Mix Less SEQ ID NO.: 17 | — | — | — | — | — | — | — | — | — | — | — | — | 0.5 | 0.5 |
| P-3SD Mod | — | — | — | — | — | — | — | 1 | — | — | — | — | — | — |
| P-3N OddC | — | — | — | — | — | — | — | — | 1 | — | — | — | — | — |
| P-3 Mismatched | — | — | — | — | — | — | — | — | — | 1 | — | — | — | — |
| cP-33' Quencher | — | — | — | — | — | — | — | — | — | — | 1 | — | — | — |
| Dye-P-3 | — | — | — | — | — | — | — | — | — | — | — | 1 | — | — |
| Water | 2.5 | 1.5 | 1.5 | 1.5 | 1.5 | 1.5 | 1.5 | 0.5 | 0.5 | 0.5 | 0.5 | 0.5 | 1.5 | 1.5 |
| Total Volume | 4 | 4 | 4 | 4 | 4 | 4 | 4 | 4 | 4 | 4 | 4 | 4 | 4 | 4 |

Bulk Enzyme Mix:

TABLE 36

| Component | 1X | A (X12) | B (X6) |
|---|---|---|---|
| 10X Reaction Buffer | 1 | 12 | 6 |
| 100% Ethylene Glycol | 1 | 12 | 6 |
| SYBR Green I (1:2000) | 1 | 12 | 6 |
| ROX-11-ddGTP | 1 | — | 6 |
| ΔTts (20 U/uL) | 1 | 12 | 6 |
| Endonuclease V | 0.075 | 0.9 | 0.45 |
| SSB (1 ng/uL) | 1 | 12 | 6 |
| Water | — | 12 | — |
| Total Vol. (uL) | 6.075 | 72.9 | 36.45 |

Figure 8:
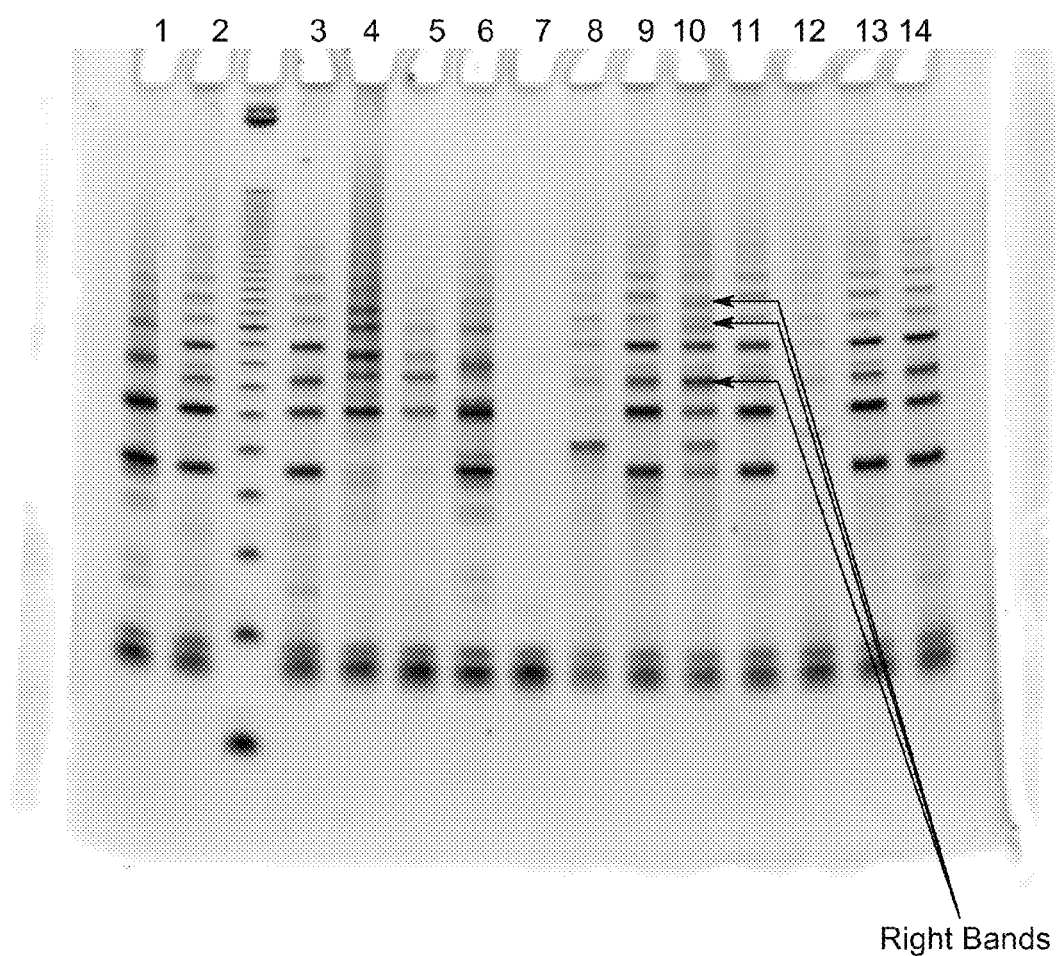
FIG. 8 depicts amplicon extension using an extension template as described in Example 7.

6 µl of "A" were added to reaction mixtures 1, 2, 4, 6, and 8-13; and 6 µl "B" were added to reaction mixtures 3, 5, 7, and 14. The resultant gel is depicted in FIG. 8. The result in lane 10 demonstrates that a primer that can hybridize partially to the single stranded amplification products of the reaction can support additional extension from the ends of those products generating a novel 3' end, or potentially displacing pre-hybridized sequences. In lane 10, the additional primer used was predicted to support the addition of 25 extra nucleotides onto the end of either the 88 nucleotide product, the 72 nucleotide product, or the 45 nucleotide product. The arrows indicate the expected 113 nucleotide, 97 nucleotide and 70 nucleotide extended products.

Example 8

Amplification Using Genomic DNA

Reaction Scheme:

TABLE 37

| Component | ID | | | | | | | | | | |
|---|---|---|---|---|---|---|---|---|---|---|---|
| | 1 | 2 | 3 | 4 | 5 | 6 | 7 | 8 | 9 | 10 | 11 |
| DNAG5 1:10 | − | + | + | + | + | + | − | − | − | − | − |
| B. cereus gDNA (100 ng/uL) | − | − | − | − | − | − | + | + | + | + | + |

TABLE 37-continued

| Component | \multicolumn{11}{c}{ID} |
|---|---|---|---|---|---|---|---|---|---|---|---|
| | 1 | 2 | 3 | 4 | 5 | 6 | 7 | 8 | 9 | 10 | 11 |
| SYBR Green I (1:2000) | + | + | + | + | + | + | + | + | + | + | + |
| SSB (100 ng/uL) | − | − | + | − | − | − | − | + | − | − | − |
| SSB (10 ng/uL) | − | − | − | + | − | − | − | − | + | − | − |
| SSB (1 ng/uL) | − | − | − | − | + | − | − | − | − | + | − |
| SSB (0.1 ng/uL) | − | − | − | − | − | + | − | − | − | − | + |

Denaturations:

TABLE 38

| Component | ID | | | | | | | | | | |
|---|---|---|---|---|---|---|---|---|---|---|---|
| | 1 | 2 | 3 | 4 | 5 | 6 | 7 | 8 | 9 | 10 | 11 |
| 10X HE Buffer | 3 | 3 | 3 | 3 | 3 | 3 | 3 | 3 | 3 | 3 | 3 |
| DNAG5 1:10 | — | 3 | 3 | 3 | 3 | 3 | — | — | — | — | — |
| B. cereus gDNA (100 ng/uL) | — | — | — | — | — | — | 3 | 3 | 3 | 3 | 3 |
| 4133-76OM n (Primer Mixture of Table 34) | 1.5 | 1.5 | 1.5 | 1.5 | 1.5 | 1.5 | 1.5 | 1.5 | 1.5 | 1.5 | 1.5 |
| Water | 10.5 | 7.5 | 7.5 | 7.5 | 7.5 | 7.5 | 7.5 | 7.5 | 7.5 | 7.5 | 7.5 |
| Total Volume (μL) | 15 | 15 | 15 | 15 | 15 | 15 | 15 | 15 | 15 | 15 | 15 |

The reaction mixtures were heated 95° C. for 2 minutes and cooled to room temperature in the thermal cycler. 3 μL of the indicated SSB solution was added to the appropriate tubes Bulk Enzyme Mix:

TABLE 39

| Component | 1X | 13X (X3) |
|---|---|---|
| 10X Rxn Buffer | 1 μL | 39 μL |
| 1:2000 SYBR Gold | 1 μL | 39 μL |
| 100% Ethylene Glycol | 1 μL | 39 μL |
| Exo (−) ΔTts | 1 μL | 39 μL |
| Endo V | 0.05 μL | 1.95 μL |
| Total Volume | 4.05 μL | 157.95 μL |

Figure 9:
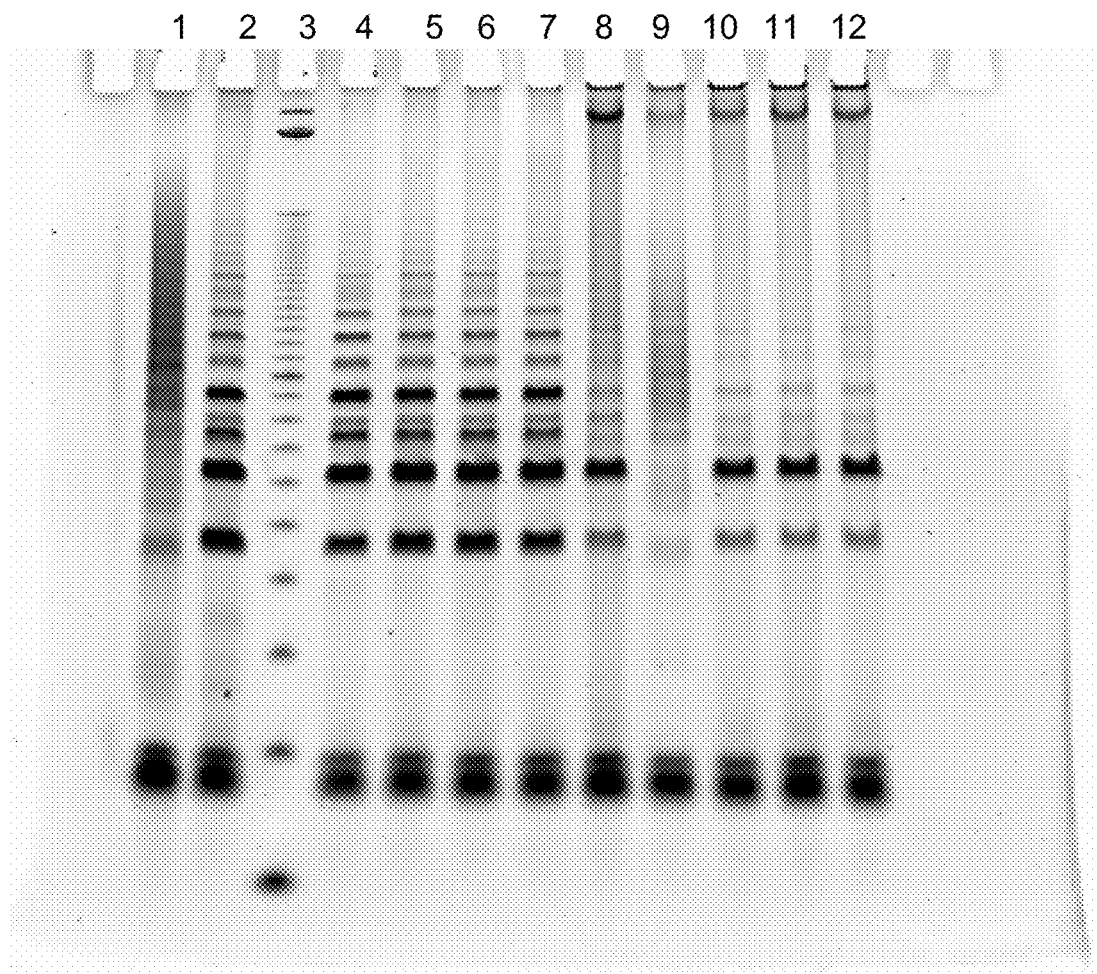
FIG. 9 depicts amplification using genomic DNA template as described in Example 8.

12 μL/reaction was cycled in an Applied Biosystems 7500 PCR System as follows: (1) Stage 1, 10 seconds at 44° C.; and (2) Stage 2, 50 seconds at 45° C. Stages 1 and 2 were repeated seventy five times and data was collected during stage 2. When completed, the reactions were stored at −20° C. overnight and then analyzed on a 10% TBE Urea gel. In this reaction performed on both artificial DNA and genomic DNA, SSB effect was being measured. The results indicate that the addition of SSB had a detrimental effect only on genomic DNA, and only at the highest concentrations used as shown in FIG. 9.

Example 9

Effect of SSB on Amplification in the Presence of Contaminating DNA

The reaction mix contained 10 mM HEPES 7.9, 3 mM MgCl$_2$, 0.25 mM dNTP, 1 mM DTT, 0.01% Tween, 10% ethylene glycol, 10% glycerol, 10 ng/μL E. coli SSB, 0.4 μM E. coli Endo V and 19 U delta Tts. Reaction mixtures containing 0.5 ng of λ DNA, 5 ng λ DNA, 50 ng λ DNA, and the 6 primers shown in Table 40 (each primer at 1 μM concentration), were incubated with and without 100 ng of E. coli genomic DNA, and a titration of E. coli SSB was added as indicated in the chart at FIG. 10.

TABLE 40

| Oligo | 6 primers used in the reactions: | Length | Ref. No.: |
|---|---|---|---|
| 7290R | AGTTCTTCTTTCGTCCCCIT | 20 | SEQ ID NO: 32 |
| 7270R | CAGGCTGACATCACIIT | 17 | SEQ ID NO: 33 |
| 7253R | TCAGTTGTTCACCCAGCIA | 19 | SEQ ID NO: 34 |
| 7062F | ACCACCGGCGATCCIIC | 17 | SEQ ID NO: 38 |
| 7079F | GCGTGAGTTCACCATIA | 17 | SEQ ID NO: 39 |
| 7114F | TGCTGCTGGCTGACCCTIA | 19 | SEQ ID NO: 53 |

Figure 10:
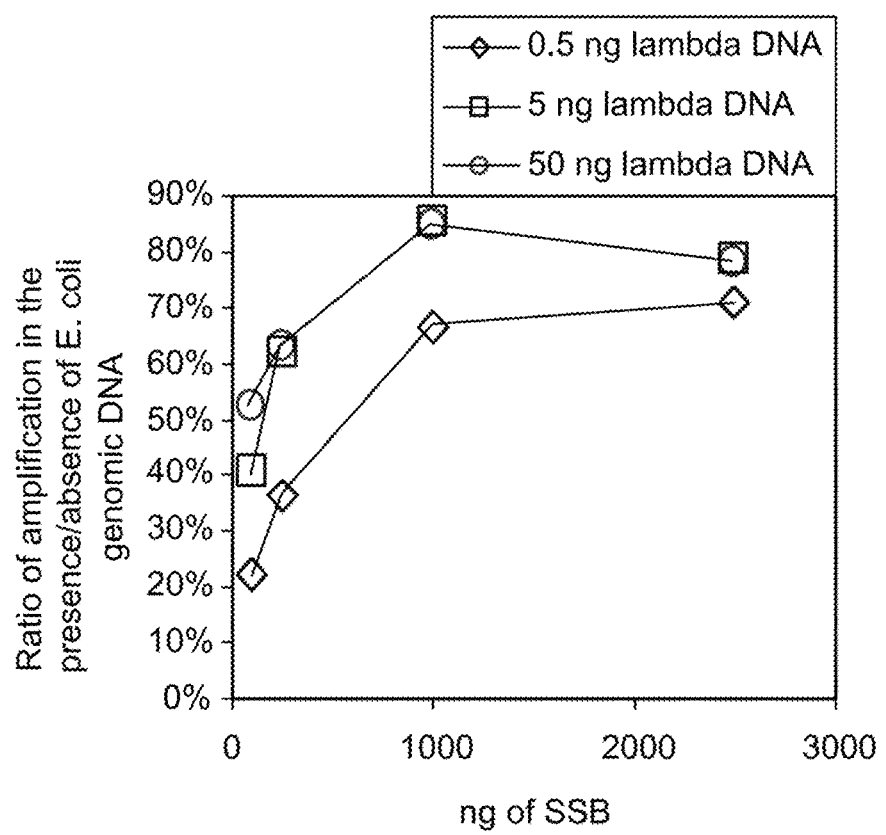
FIG. 10 shows amplicon generation from lambda DNA (102 nucleotide products) and the effects of contaminating DNA as described in Example 9.

Template and primers were pre-annealed by denaturation at 95° C. for 2 min. then placed at room temperature, and then mixed with the rest of reaction components. Reactions were incubated for 80 min. at 45° C. and products were separated on TBE-Urea gel. Gels were stained using SYBR gold and scanned on Typhoon scanner. As shown in FIG. 10, the SSB enhanced amplification of product (102 base pair products) in the presence of contaminating genomic DNA.

Example 10

Generation and Expression of Y75A E. coli Endonuclease V and Y74A Aft Endonuclease V The original plasmid encodes wild type E. coli endo V in pET22b+ as a terminal HIS tagged fusion construct, flanked by an NdeI site at the initiation and a XhoI site at the termination sequence. PCR was performed using primer "endo V us" with "endo V int ds" (SEQ ID NO: 26 and SEQ ID NO: 29) to make a 215 base pair gene fragment. This fragment was restricted using NdeI and NgoI to generate cohesive ends. PCR was performed using primer "endo V ds" with "endo V int us" to make a 457 base pair gene fragment. This fragment was restricted using NgoI and XhoI to generate cohesive ends. The fragments were ligated in a "3-way" reaction containing pET22b+ that had been linearized with NdeI and XhoI. After transformation into host E. coli strain JM109 (DE3), a clone was sequenced to confirm mutagenesis.

Protein was expressed and purified by standard techniques: Transformed E. coli JM109 (DE3) was grown in 2×YT medium and protein expression induced with IPTG. Protein was extracted into lysis buffer consisting of 10 mM HEPES buffer (pH 8), 1 M NaCl, 0.1% TritonX-100, 0.1% Tween-20, 10 mM β-ME, 5% glycerol, 10 mM Imidazole, with Roche "Complete" protease inhibitors. Sonication was used to disrupt the cells, and the extract clarified by centrifugation before application of the Ni-NTA resin. Captured protein was eluted into lysis buffer with 200 mM Imidazole. Batch mode capture, wash, and elution on Ni-NTA resin were preformed according to manufacturer recommendations (Qiagen Corp.). The eluate was dialyzed and stored in a buffer consisting of 10 mM HEPES buffer (pH 8), 150 mM NaCl, 0.1 mM EDTA, 0.01% TritonX-100, and 50% glycerol.

Y74A mutant Afu endonuclease V was prepared the same way as the *E. coli* mutant, and has a sequence of SEQ ID NO: 3.

Example 12

Mutant Endo V Performance Characteristics

Reactions containing (25 mM Tris:borate (pH=8.1), 5 mM MgCl$_2$, 1 mM DTT, 0.01% tween-20) and 1 pmole of FAM-I primer (SEQ ID NO: 24) and 1 pmole HEX-C oligo (SEQ ID NO: 25), pre-annealed, were incubated at 37° C. for 0, 5, 30, 60, 120, and 480 minutes with either 1, 0.3, or 0.1 pmoles of wild type *E. coli* endo V or *E. coli* Y75A mutant endo V. Reactions were resolved by denaturing acrylamide gel electrophoresis and gels visualized by scanning on a Typhoon 9410. The small molecular weight nicked product was quantified and the relative fluorescence was compared and depicted in FIG. 11A and FIG. 11B. Results indicate that the mutant enzyme supports repeated nicking by each enzyme (when there is an Inosine opposite to Cytosine), while the wild type enzyme seems capable of only a single round of nicking. The mutant enzyme supports repeated nicking by each enzyme (as evidenced by the extended kinetics; the ability of enzyme to hop from one DNA to another), while the wild type enzyme seems capable of only a single round of nicking (as evidenced by the short burst kinetics).

Example 13

Inosine Specificity of *E. coli* Mutant Endo V

Reaction mixtures containing (25 mM Tris HCl (pH 8.5), 5 mM MgCl$_2$, 1 mM DTT, 0.01% tween 20, 10% glycerol) were prepared with 200 ng of either HindIII linearized pUC18 DNA or 200 ng of HindIII restricted pUC18 DNA that had been amplified using a modified rolling circle amplification reaction in which the dGTP has been substantially replaced with dITP to generate amplified material containing dIMP in place of dGMP, as indicated.

To the reaction was added either wild type or mutant *E. coli* endo V as indicated (0, 0.01, 0.1, or 1 microgram of protein), and incubated at 37° C. for 90 minutes. Reactions were then visualized by denaturing agarose gel electrophoresis, staining with SYBR gold and scanning on the Typhoon 9410. Results shown in FIG. 12 indicate that both wild type and mutant enzyme have at least 100× increased nicking activity toward inosine-containing DNA as compared to guanine-containing DNA.

Example 14

Amplification Reaction using Mutant or Wild Type *E. coli* Endonuclease

Time course of amplification was studied in reaction mix containing 10 mM Tris (pH 8.3), 2 mM MgCl$_2$, 0.01% Tween-20, 200 μM dNTP's, 10% Ethylene Glycol, 2 mM DTT, 25 ng/μL SSB, 10 nM exo (−) Bst polymerase, Large Fragment, and 10 nM *E. coli* Endo V Y75A mutant. DNA substrate was 10 ng or 15 fmol of approximately 1 kb size PCR products made with I or G (penultimate base to 3' end) containing PCR primers (described in Table 41). Reactions were stopped at 15, 30, 60, 120, 240, 480, and 1260 min, by adding EDTA to 10 mM and samples were run on a 1% alkaline agarose gel to separate amplification products. Gels were then neutralized and stained with SYBR gold and scanned and quantified on Typhoon 9410 and ImageQuant image analysis software, as shown in FIG. 13.

TABLE 41

| Name | Sequence | Length | Ref. No.: |
|---|---|---|---|
| Forward primer 40FGI | GTTTTCCCAGTCACGACGTTGTA AAACGACGICC | 34 | SEQ ID NO:47 |
| Reverse primer: | TCAAAGAAGTATTGCTACAACG G | 23 | SEQ ID NO:48 |
| Forward primer: 40FGG | GTTTTCCCAGTCACGACGTTGTA AAACGACGGCC | 34 | SEQ ID NO:49 |
| Reverse primer: | TCAAAGAAGTATTGCTACAACG G | 23 | SEQ ID NO:50 |

Example 15

Kinetics of Amplification: Comparison of *E. coli* Y75A Mutant Endo V Versus Afu. Y74A Mutant Endo V

TABLE 42

| Name | Sequence | Length | Ref. No.: |
|---|---|---|---|
| Tban-1 DNA Template | CAATAGACTCCATACCACCAA TTGTAATTTCTGTACGTCTCTT ATCATTGAAGCGCTCTTTTACT TCTGTTAATTCTTCACGAATAA TCTCAAGAACCTTTTCTTCATC TGC | 112 | SEQ ID NO: 54 |
| Tban-1 forward primer: | GCAGATGAAGAAAAGGTTCTT GAGATTATTCIT | 33 | SEQ ID NO: 51 |
| Tban-1 reverse primer | CAATAGACTCCATACCACCAA TTGTAATTTCTIT | 34 | SEQ ID NO: 55 |

Amplification reactions were carried out in reaction mix containing 10 mM Tris (pH 8.3), 3 mM MgCl$_2$, 0.01% Tween-20, 250 μM dNTP's, 10% Ethylene Glycol, 1 mM DTT, 50 nM exo (−) Bst polymerase large Fragment, or Tma polymerase (100 ng), and 0.8 μM *E. coli* Endo V, *E. coli* Y75A mutant endo V or 0.4 μM Afu, Endo V, Afu Y75A mutant endo V. Both forward and reverse primers (described in Table 42) were maintained at 0.25 μM and template at 0.1 μM.

Reactions were incubated for 80 min. at 45° C. and products were separated on TBE-Urea gel. Gels were stained using SYBR gold and scanned on Typhoon scanner as shown on FIG. 14. In both cases the correct amplification products of 45 nucleotides and 79 nucleotides were observed.

Example 16

Thermal Stability of Mutant Endo V

E. coli Y75A mutant Endo V at a concentration of 1.6 µM was incubated at following temperatures: on ice, 37° C., 40° C., 43° C., 46° C., 49° C., 52° C., 55° C., and 58° C. for different amount of times such as 15, 30, 45, 60, and 75 min., in buffer containing 10 mM HEPES (pH 7.9), 3 mM $MgCl_2$, 0.25 mM dNTP, 1 mM DTT, 0.01% Tween, 10% ethylene glycol, and 0.5 µL ThermoFidelase (Fidelity Systems).

At time points indicated above samples were removed from the incubator and put on ice until all incubations were completed. To these pre-incubated samples following reaction components were added (10 mM HEPES (pH 7.9), 0.25 mM dNTP, 1 mM DTT, 0.01% Tween, 10% ethylene glycol) and P1/P2-1/P3 primer mix (to 0.2/1/1.8 µM each), 0.5 nM template, 10 ng/µL of T4 g32 protein, 5U exo(−) Klenow polymerase.

All reactions were then incubated at 45° C. for 80 min. Products were separated on TBE-Urea gel that was stained using SYBR gold and scanned on Typhoon scanner. The results are shown in FIG. 15. The endonuclease V mutant maintains stability up to 46° C. for 75 minutes, and was inactivated at 49° C.

Example 17

Real Time Analysis of Amplicon Generation

A dilution series of lambda DNA was prepared in HETB buffer (10 mM HEPES (pH 7.9), 0.1 mM EDTA, 0.01% tween-20, 0.5 mg/ml BSA) and 10 pmoles each of the following primers: (7062F, 7079F, 7096F, 7111F, 7127F, 7144F, 7290R, 7270R, 7253R, 7234R, 7215R, 7194R, shown below in Table 43) and heat denatured for 2 minutes at 95° C. and then chilled on ice.

TABLE 43

| Oligo | Length |
| --- | --- |
| 7290R | 20 |
| 7270R | 17 |
| 7253R | 19 |
| 7234R | 19 |
| 7215R | 17 |
| 7194R | 19 |
| 7062F | 17 |
| 7079F | 17 |
| 7096F | 18 |
| 7111F | 16 |
| 7127F | 17 |
| 7144F | 15 |
| T7-7158F-misA: | 50 |
| Quencher-oligo | 24 |
| Dye-oligo | 24 |

A mix containing the following components was then added to a final concentration of: 35 units delta Tts, 8 pmoles E. coli Y75A endo V mutant, 0.002 mg SSB, 3 mM $MgCl_2$, 0.1 mM MnSO4, 3 pmole ROX std dye (internal control), 1× buffer (20 mM HEPES (pH 7.9), 0.25 mM dNTP, 1 mM DTT, 0.01% Tween, 10% glycerol, and 10% ethylene glycol. Then 3 pmoles T7-7158F-misA, 4 pmoles quencher-oligo, 2.5 pmoles dye-oligo were mixed in HET buffer, heated to 95° C. for 45 seconds and slow cooled to ice over 5 minutes and added to the amplification reaction.

The reactions were cycled an ABI 7500 75 times (46° C., 50 seconds; 45° C., 10 second), taking readings during the 46° C. step. This 1° C. cycle was employed because the ABI machine does not hold reactions at a single temperature. A 75-minute incubation was performed and data was exported to excel. The time at which each reaction produced a signal above a threshold level was plotted on a semi log scale. A linear curve was generated (shown in FIG. 16, amplification time v. initial DNA concentration), indicating that the reaction gave reliable quantification over at least 5 orders of magnitude.

Example 18

Nicking Efficiency of Y80A Mutant Tma Endonuclease V (SEQ ID NO: 58) on Double Stranded DNA and Single Stranded DNA The indicated amount of either wild type Tma endoV or Y80A mutant Tma endoV was incubated with 3 pmoles of fluorescent primer 1 (SEQ ID NO: 24) alone or annealed to fluorescent primer 2 (SEQ ID NO: 25), in 1× reaction buffer at 60 degrees for 30 minutes. Reactions were separated on denaturing polyacrylamide and visualized by scanning for fluorescein fluorescence. The amount of nicked product was quantified and reported in the graph. Nicking efficiency of Y80A mutant Tma endonuclease V (SEQ ID NO: 58) on double stranded DNA and single stranded DNA is shown FIG. 17. It was observed that the mutant Tma endonuclease V nicks a single stranded DNA faster than a double stranded DNA.

Example 19

Nicking of Double Stranded DNA and Single Stranded DNA by Tma Endonuclease V at 45 C and 60 C The indicated amount of either wild type Tma endo V or Y80A mutant Tma endo V was incubated with 3 pmoles of fluorescent primer 1 (SEQ ID NO: 24, referred in FIG. 18 as "F") alone or annealed to fluorescent primer 2 (SEQ ID NO: 25, referred in FIG. 18 as "H"), in 1× reaction buffer at either 45 or 60 degrees, as indicated, for 30 minutes. Reactions were separated on denaturing polyacrylamide and visualized by scanning for fluorescein fluorescence.

FIG. 18 shows that the Y80A mutant Tma endo V is more active at 60 degrees than at 45 degrees, and this may indicate that this higher temperature is required for the enzyme to dissociate from a nicked product effectively.

Example 20

Nicking of Double Stranded DNA Y80A Tma Endonuclease V at 60 C in the Presence of Various Additives 4 ng of Y80A mutant Tma endo V was incubated 15 minutes at 60 degrees in reaction buffer (25 mM HEPES (pH=8), 3 mM $MgCl_2$, 0.1 mM $MnSO_4$, 250 µM each dNTP (all 4), 1 mM TCEP, 0.1 mM EDTA, 0.02% Tween 20, 5 mM $(NH4)_2SO_4$), containing 3 pmoles of fluorescent primer 1 (SEQ ID NO: 24, referred in FIG. 19 as "FAM") annealed to fluorescent primer 2 (SEQ ID NO: 25, referred in FIG. 19 as "HEX") and the resulting denaturing polyacrylamide gel scanned for fluorescein (FAM) and for hexachloro-fluorescein (HEX).

FIG. 19 shows that the strand containing inosine is the only that gets nicked under any condition. Also, that the addition of 1 ug of E. coli SSB inhibits Y80A mutant Tma endo V nicking, and that this inhibition is only slightly relieved by the addition of 20% ethylene glycol and 10% glycerol. This is quite different from what is observed with Y75A E. coli endo V in which the addition of SSB is not inhibitory at all. If SSB is required for effective strand displacement synthesis in a DNA amplification such as one described herein, the Y75A *E. coli* endo V may be preferred over the Y80A Tma endo V.

Example 21

Nicking Efficiency of Various Mutant Endonuclease V Enzymes on Double Stranded DNA and Single Stranded DNA Nicking efficiency of either Y75A mutant *E. coli* endonuclease V (SEQ ID NO: 2) or Y80A mutant Tma endonuclease V were tested on 3 pmoles of fluorescent primer 1 (SEQ ID NO: 24) alone or annealed to 3 pmoles of fluorescent primer 2 (SEQ ID NO: 25), as indicated.

The nicking reaction is performed under the following conditions: 25 mM HEPES (pH=8), 3 mM $MgCl_2$, 0.1 mM $MnSO_4$, 250 µM each dNTP (all 4), 1 mM TCEP, 0.1 mM EDTA, 0.02% Tween 20, 5 mM $(NH_4)_2SO_4$. Reactions were incubated either at 45 degrees or 60 degrees as indicated and resolved on denaturing polyacrylamide and visualized by scanning for fluorescein.

FIG. 20 demonstrate that the Y75A mutant *E. coli* endonuclease V (SEQ ID NO: 2) is more effective in nicking a double stranded DNA than a single stranded DNA as compared to Y80A mutant Tma endonuclease V (SEQ ID NO: 58, wherein a Tyrosine residue at the 80$^{th}$ position of a WT Tma endo V (SEQ ID No: 57) is replaced with an Alanine residue), which is more effective at nicking single stranded DNA than double stranded DNA at 45° C., but about equally active towards both substrates at 60° C. This suggests that if amplification of DNA by the methods described herein are to be attempted, the Y80A mutant Tma endo V may require incubation at 60° C. or higher, while the Y75A *E. coli* endo V can be used at 45° C.

Example 22

Nicking Efficiency of Y75A Mutant *E. Coli* Endonuclease V (SEQ ID NO: 2) on Single Stranded DNA and Double Stranded DNA in Various Buffers The nicking experiments were performed on 3 pmoles of fluorescent primer 1 (SEQ ID NO:24) annealed to fluorescent primer 2 (SEQ ID NO: 25) in the following buffers. Buffer (1): 10 mM HEPES (pH=8.0), 3 mM $MgCl_2$, 0.01% Tween 20 and 1 mM TCEP; Buffer (2): Buffer (1)+0.1 mM $MnSO_4$; Buffer (3): Buffer (1)+250 µM dATP; Buffer (4): Buffer (1)+250 µM dCTP; Buffer (5): Buffer (1)+250 µM dGTP; Buffer (6): Buffer (1)+250 µM dTTP; Buffer (7): Buffer (2)+250 µM each of dNTP (all 4); Buffer (8): 10 mM TRIS (pH=8.0)+2 mM $MgCl_2$, 0.01% Tween 20 and 1 mM TCEP.

FIG. 21 demonstrates that Y75A mutant *E. coli* endonuclease V nicks single stranded DNA at a slower rate than the double stranded DNA. Addition of $Mn^{2+}$ increases activity on single stranded DNA as compared to that of double stranded DNA. However, addition of any dNTP to the single stranded DNA nicking reaction with the presence of $Mn^{2+}$ the endo activity on single stranded DNA to the rate seen with single stranded DNA without $Mn^{2+}$.

The invention may be embodied in other specific forms without departing from the spirit or essential characteristics thereof. The foregoing embodiments are selected embodiments or examples from a manifold of all possible embodiments or examples. The foregoing embodiments are therefore to be considered in all respects as illustrative rather than limiting on the invention described herein. While only certain features of the invention have been illustrated and described herein, it is to be understood that one skilled in the art, given the benefit of this disclosure, will be able to identify, select, optimize or modify suitable conditions/parameters for using the methods in accordance with the principles of the present invention, suitable for these and other types of applications. The precise use, choice of reagents, choice of variables such as concentration, volume, incubation time, incubation temperature, and the like may depend in large part on the particular application for which it is intended. It is, therefore, to be understood that the appended claims are intended to cover all modifications and changes that fall within the true spirit of the present invention. Further, all changes that come within the meaning and range of equivalency of the claims are intended to be embraced therein.

---

The invention claimed is:

1. A mutant endonuclease V comprising amino acid sequence of SEQ ID NO: 1, wherein its Tyrosine 75 residue is replaced with Alanine.

2. The mutant endonuclease of claim 1, wherein the mutant endonuclease is a thermo labile endonuclease.

3. The mutant endonuclease of claim 1, wherein the mutant endonuclease nicks an inosine-containing strand of a double stranded DNA that contains an inosine residue base-paired with a cytosine residue at a position 3' to the inosine residue.

4. The mutant endonuclease of claim 3, wherein the mutant endonuclease has a higher nicking efficiency than a wild type endonuclease V of SEQ ID NO: 1.

5. A mutant *Escherichia coli* endonuclease V comprising amino acid sequence of SEQ ID NO: 2.

6. The mutant endonuclease of claim 5, wherein the mutant endonuclease preferentially nicks an inosine-containing strand of a double stranded DNA that contains an inosine residue base-paired with a cytosine residue at a position 3' to the inosine residue.

7. The mutant endonuclease of claim 5, wherein the mutant endonuclease nicks a double stranded DNA at the location of a base pair mismatch or at one or more bases 3' to the base pair mismatch.

8. A mutant *Archaeoglobus fulgidus* endonuclease V comprising amino acid sequence of SEQ ID NO: 3.

* * * * *